United States Patent
Hestness et al.

(10) Patent No.: US 10,010,266 B2
(45) Date of Patent: Jul. 3, 2018

(54) MEDICAL BREATHING APPARATUS

(71) Applicant: AIRWAY CONTROL TECHNOLOGIES, LLC, Bloomington, MN (US)

(72) Inventors: Timothy Hestness, Shakopee, MN (US); Robert Moore, Bloomington, MN (US)

(73) Assignee: AIRWAY CONTROL TECHNOLOGIES, LLC, Bloomington, MN (US)

( * ) Notice: Subject to any disclaimer, the term of this patent is extended or adjusted under 35 U.S.C. 154(b) by 974 days.

(21) Appl. No.: 14/213,797

(22) Filed: Mar. 14, 2014

(65) Prior Publication Data

US 2014/0276171 A1 Sep. 18, 2014

Related U.S. Application Data

(60) Provisional application No. 61/798,543, filed on Mar. 15, 2013.

(51) Int. Cl.
*A61M 16/00* (2006.01)
*A61B 5/097* (2006.01)
(Continued)

(52) U.S. Cl.
CPC .............. *A61B 5/097* (2013.01); *A61B 1/24* (2013.01); *A61B 5/01* (2013.01); *A61B 5/0833* (2013.01);
(Continued)

(58) Field of Classification Search
CPC ........ A61M 16/06; A61B 5/682; A61B 5/097; A61B 5/4818
See application file for complete search history.

(56) References Cited

U.S. PATENT DOCUMENTS

| | | | |
|---|---|---|---|
| 4,495,945 A | | 1/1985 | Liegner |
| 4,966,141 A | * | 10/1990 | Bacaner ............... A61B 5/0205 128/207.14 |

(Continued)

FOREIGN PATENT DOCUMENTS

| | | |
|---|---|---|
| DE | 3502766 A1 | 7/1986 |
| WO | 9003199 A1 | 4/1990 |

OTHER PUBLICATIONS

Kodali, B.S., "Capnography Outside the Operating Rooms", Anesthesiology, vol. 118, No. 1, Jan. 2013, pp. 192-201, the American Society of Anesthesiologists, Inc. Lippincott Williams & Wilkins.

*Primary Examiner* — Patricia Mallari
*Assistant Examiner* — Karen Toth
(74) *Attorney, Agent, or Firm* — Seager, Tufte & Wickhem, LLP

(57) ABSTRACT

A medical mouthpiece may include a U-shaped first member having a tubular portion, the first member forming at least one lateral interocclusal passageway extending through the first member, and a second member received within the tubular portion. A medical breathing apparatus may include a U-shaped first member forming left and right lateral interocclusal passageways extending through the first member, a second member attached to the first member, and an adapter receivable within a tubular portion of the first member, wherein the adapter includes a respiratory orifice configured to deliver respiratory gas to the left and right lateral interocclusal passageways. A method for delivering positive pressure and/or a respiratory gas to a patient may include inserting a mouthpiece into a mouth of the patient, and delivering the positive pressure and/or the respiratory gas through the mouthpiece to a space adjacent a posterior oropharynx of the patient.

16 Claims, 37 Drawing Sheets

(51) Int. Cl.
    *A61B 17/02*     (2006.01)
    *A61B 17/34*     (2006.01)
    *A61B 5/083*     (2006.01)
    *A61M 16/04*     (2006.01)
    *A61B 5/01*     (2006.01)
    *A61B 1/24*     (2006.01)
    *A61B 90/30*     (2016.01)
    *A61C 5/90*     (2017.01)
    *A61F 5/56*     (2006.01)
    *A61M 16/08*     (2006.01)

(52) U.S. Cl.
    CPC ........ *A61B 5/0836* (2013.01); *A61B 17/0218* (2013.01); *A61B 17/3423* (2013.01); *A61B 90/30* (2016.02); *A61C 5/90* (2017.02); *A61M 16/0493* (2014.02); *A61F 5/566* (2013.01); *A61M 16/085* (2014.02); *A61M 2202/0208* (2013.01); *A61M 2202/0283* (2013.01); *A61M 2205/7536* (2013.01); *A61M 2230/432* (2013.01); *Y02C 20/10* (2013.01)

(56) References Cited

U.S. PATENT DOCUMENTS

| | | |
|---|---|---|
| 5,089,637 A | 2/1992 | Urban |
| 5,413,095 A | 5/1995 | Weaver |
| 5,513,634 A | 5/1996 | Jackson |
| 5,624,257 A | 4/1997 | Farrell |
| 5,626,128 A | 5/1997 | Bradley et al. |
| 5,752,510 A | 5/1998 | Goldstein |
| 5,950,624 A | 9/1999 | Hart |
| 5,957,133 A | 9/1999 | Hart |
| 6,209,542 B1 | 4/2001 | Thornton |
| 6,334,064 B1 * | 12/2001 | Fiddian-Green ... A61B 5/14539 600/311 |
| 6,379,312 B2 | 4/2002 | O'Toole |
| 6,386,199 B1 | 5/2002 | Alfery |
| 6,422,240 B1 | 7/2002 | Levitsky et al. |
| 6,533,582 B2 | 3/2003 | Lindquist |
| 6,571,798 B1 | 6/2003 | Thornton |
| 6,729,325 B2 | 5/2004 | Alfery |
| 6,830,445 B2 | 12/2004 | Curti |
| 6,983,744 B2 | 1/2006 | Alfery |
| 6,997,186 B2 | 2/2006 | Robertson et al. |
| 7,007,694 B2 | 3/2006 | Aylsworth et al. |
| 7,118,377 B2 | 10/2006 | Inoue et al. |
| 7,171,962 B1 | 2/2007 | Bloem |
| 7,311,103 B2 | 12/2007 | Jeppesen |
| 7,337,780 B2 | 3/2008 | Curti et al. |
| 7,364,682 B2 | 4/2008 | Curti et al. |
| 7,383,839 B2 | 6/2008 | Porat et al. |
| 7,451,766 B2 | 11/2008 | Miller |
| 7,624,736 B2 | 12/2009 | Borody |
| 7,743,770 B2 | 6/2010 | Curti et al. |
| 7,832,400 B2 | 11/2010 | Curti et al. |
| 7,935,065 B2 | 5/2011 | Martin et al. |
| 7,946,288 B2 | 5/2011 | Flynn et al. |
| 8,020,276 B2 | 9/2011 | Thornton |
| 8,091,554 B2 | 1/2012 | Jiang |
| 8,122,889 B2 | 2/2012 | Vaska et al. |
| 2003/0089371 A1 | 5/2003 | Robertson et al. |
| 2003/0236452 A1 * | 12/2003 | Melker ................ A61B 5/0873 600/323 |
| 2004/0211430 A1 * | 10/2004 | Pivovarov ............... A61F 5/566 128/848 |
| 2006/0112962 A1 * | 6/2006 | Tebbutt ............. A61M 16/0488 128/206.29 |
| 2008/0308108 A1 | 12/2008 | Diorio |
| 2010/0316973 A1 | 12/2010 | Remmers et al. |
| 2011/0005531 A1 | 1/2011 | Manzo |
| 2011/0180076 A1 | 7/2011 | Hegde et al. |
| 2012/0172678 A1 | 7/2012 | Logan et al. |
| 2012/0172679 A1 | 7/2012 | Logan et al. |

* cited by examiner

MEDICAL BREATHING APPARATUS

REFERENCE TO RELATED APPLICATIONS

This application claims priority under 35 U.S.C. § 119(e) to U.S. Provisional Application No. 61/798,543, filed Mar. 15, 2013, the entire disclosure of which is herein incorporated by reference.

FIELD OF THE INVENTION

The present invention pertains to medical devices and methods for using medical devices. More particularly, the present invention pertains to medical devices for respiratory support.

BACKGROUND

A wide variety of devices have been developed for medical use, for example, use in the mouth or respiratory system. Some of these devices include oral appliances, oral or nasal cannulas, breathing or ventilation tubes, and the like. These devices may be used according to any one of a variety of methods. Of the known medical devices and methods, each has certain advantages and disadvantages. There is an ongoing need to provide alternative medical devices as well as alternative methods for using medical devices.

BRIEF SUMMARY

A medical mouthpiece may include a generally U-shaped member forming an upper surface configured to contact an upper dentition of a patient spaced apart from a lower surface configured to contact a lower dentition of the patient, wherein the U-shaped member forms a lateral interocclusal passageway extending from an anterior aperture to a posterior aperture between the upper surface and the lower surface, the lateral interocclusal passageway configured to provide a conduit for respiratory gas exchange.

A medical mouthpiece may include a generally U-shaped member forming an upper surface configured to contact an upper dentition of a patient spaced apart from a lower surface configured to contact a lower dentition of the patient, a sampling port formed within a posterior portion of the generally U-shaped member, the sampling port having a sampling orifice recessed within the posterior portion which in some, but not all, embodiments may be facing in a posterior direction, and a sampling conduit for fluid communication between the sampling port and an analyzing apparatus configured to analyze exhaled respiratory gases.

A medical mouthpiece may include a generally U-shaped member forming an upper surface configured to contact an upper dentition of a patient spaced apart from a lower surface configured to contact a lower dentition of the patient, and a supplemental gas conduit for fluid communication between a source of supplemental gas and a supply orifice formed in the generally U-shaped member.

A medical mouthpiece may include a generally U-shaped member forming an upper surface configured to contact an upper dentition of a patient spaced apart from a lower surface configured to contact a lower dentition of the patient, wherein the U-shaped member forms a lateral interocclusal passageway extending from an anterior aperture to a posterior aperture between the upper surface and the lower surface, the lateral interocclusal passageway configured to provide a conduit for respiratory gas exchange, a sampling port formed within a posterior portion of the lateral interocclusal passageway and may have a sampling orifice that may be facing in a posterior direction, the sampling port configured to be positioned in a posterior portion of a lateral interocclusal space of the patient, a sampling conduit for fluid communication between the sampling port and an analyzing apparatus configured to analyze exhaled respiratory gases, and a supplemental gas conduit for fluid communication between a source of supplemental gas and a supply orifice within the lateral interocclusal passageway.

A medical mouthpiece may include a generally U-shaped member forming an upper surface configured to contact an upper dentition of a patient spaced apart from a lower surface configured to contact a lower dentition of the patient, wherein the U-shaped member forms a lateral interocclusal passageway extending from an anterior aperture to a posterior aperture along an axis defined by a line between the upper dentition and the lower dentition, the lateral interocclusal passageway configured to provide a conduit for respiratory gas exchange, a sampling port formed within a posterior portion of the lateral interocclusal passageway and may have a sampling orifice that may be facing in a posterior direction, a sampling conduit fluidly connecting the sampling port and an analyzing apparatus configured to analyze exhaled respiratory gases collected adjacent the oropharynx of the patient, and a supplemental gas conduit fluidly connecting a source of supplemental gas and a supply orifice within the lateral interocclusal passageway.

A medical mouthpiece may include a generally U-shaped first member forming an upper channel spaced apart from a lower channel with left and right lateral interocclusal passageways formed therebetween, the left and right lateral interocclusal passageways extending from an anterior portion of the first member through a posterior portion of the first member, and a first central orifice extending through the anterior portion, wherein the first member is shaped and configured to receive an upper dentition of a patient in the upper channel or a lower dentition of a patient in the lower channel, and a second member attached to the anterior portion, the second member including a second central orifice extending through the second member and in communication with the first central orifice to form a central passageway extending through the mouthpiece, wherein the second member includes a first port and a second port formed therein, the first port being fluidly connected to a left lateral interocclusal sampling port and a right lateral interocclusal sampling port for sampling expiration gases, the left and right lateral interocclusal sampling ports being disposed within the left and right inter-occlusal passageways, respectively, proximate the posterior portion, the second port being fluidly connected to the left and right lateral interocclusal passageways for delivery of a supplemental gas into the left and right lateral interocclusal passageways.

A method for delivering a gas to a patient may include inserting a mouthpiece into a mouth of a patient, the mouthpiece having a generally U-shaped member forming a lateral interocclusal passageway extending posteriorly between an upper dentition and a lower dentition of the patient, and delivering a gas to the patient through the lateral interocclusal passageway such that the gas is delivered through a posterior aperture to a space adjacent the patient's posterior oropharynx.

A medical mouthpiece may include a generally U-shaped first member having a tubular portion extending anteriorly therefrom, the first member including an upper surface configured to contact an upper dentition of a patient spaced apart from a lower surface configured to contact a lower dentition of the patient, wherein the first member includes a posterior central orifice extending anteriorly to posteriorly through the first member along a medial line, wherein the first member forms at least one lateral interocclusal passageway extending anteriorly to posteriorly through the first member between the upper surface and the lower surface; and a second member slidably received within the tubular portion, the second member including a perimeter ring defining an outwardly-facing surface configured to be in facing engagement with an inner surface of the tubular portion, wherein the second member includes an anterior central orifice extending anteriorly to posteriorly through the second member along the medial line, the anterior central orifice cooperating with the posterior central orifice to form a central passageway extending through the mouthpiece, wherein the second member includes one or more anterior apertures and at least one lateral interocclusal passageway passing through the perimeter ring anteriorly to posteriorly from the one or more anterior apertures.

A medical breathing apparatus may include a generally U-shaped first member forming an upper surface spaced apart from a lower surface with left and right lateral interocclusal passageways formed therebetween, the left and right lateral interocclusal passageways extending from an anterior portion of the first member through a posterior portion of the first member, and a posterior central orifice extending through the anterior portion from a first cavity defined by a tubular portion extending anteriorly from the anterior portion of the first member, wherein the first member is shaped and configured to contact an upper dentition of a patient with the upper surface or a lower dentition of a patient with the lower surface; a second member attached to the anterior portion, the second member including an anterior central orifice extending through the second member and in communication with the posterior central orifice to form a central passageway extending through the first member and the second member, wherein the second member includes one or more anterior apertures in fluid communication with the left and right lateral interocclusal passageways; and an adapter slidably receivable within the first cavity of the tubular portion of the first member, wherein the adapter includes a central orifice configured to engage the second member as an extension of the central passageway, and a respiratory orifice configured to deliver respiratory gas to the left and right lateral interocclusal passageways.

A method for delivering a respiratory gas to a patient may include inserting a mouthpiece, as described above, into a mouth of the patient; and delivering the respiratory gas to the patient through the at least one lateral interocclusal passageway of the first member such that the respiratory gas is delivered through a posterior aperture to a space adjacent a posterior oropharynx of the patient.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
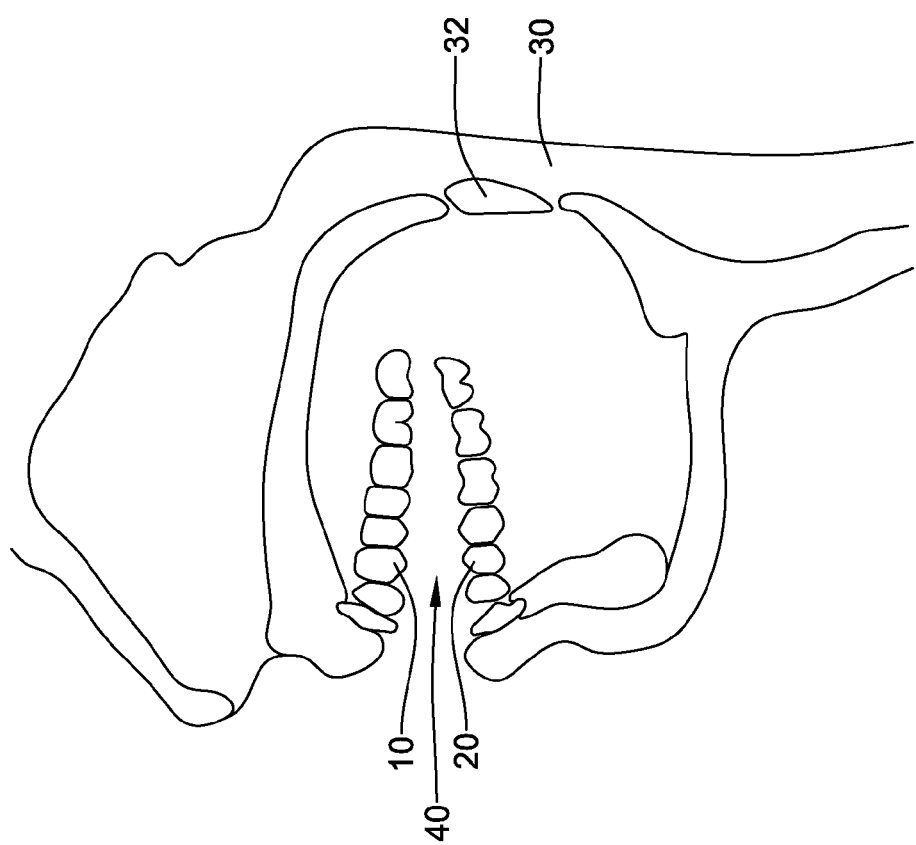
FIG. 1 is a partial side view of mouth anatomy.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

The "oral cavity" may be defined as the cavity of the mouth, particularly the part of the mouth behind the gums and teeth that is bounded above by the hard and soft palates and below by the tongue and by the mucous membrane connecting it with the inner part of the mandible.

A "dentition" refers to a character of a set of teeth, particularly with respect to number, kind, and/or arrangement. For example, the teeth of the upper jaw or maxilla may be referred to as the "upper dentition" and the teeth of the lower jaw or mandible may be referred to as the "lower dentition".

The term "interocclusal" refers to the space situated between the occlusal surfaces of opposing teeth in the two dental arches. In other words, the interocclusal space may be considered to encompass the vertical (i.e., superior-inferior) space between the upper dentition or teeth and the lower dentition or teeth. The interocclusal space may be further separated into an anterior interocclusal space generally situated between the upper and lower incisors or front teeth of the two dental arches, and a lateral interocclusal space (or spaces) generally situated outside or on either side of the upper and lower incisors and/or between the upper and lower molars of the two dental arches. In some embodiments, the lateral interocclusal space may lie generally along a line or axis following or aligned with the molars.

The "buccal cavity" may be considered to represent the area of the mouth located between the teeth and cheeks.

The terms "anterior", "posterior", "superior", "inferior", and/or "medial" (and other forms thereof) may be considered to define the orientation of a device or feature as the device or feature is received or positioned in a human mouth.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. While certain features may be discussed herein in the singular, it is to be understood that the details may apply to one, more than one, or all of the attendant features.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

Figure 2:
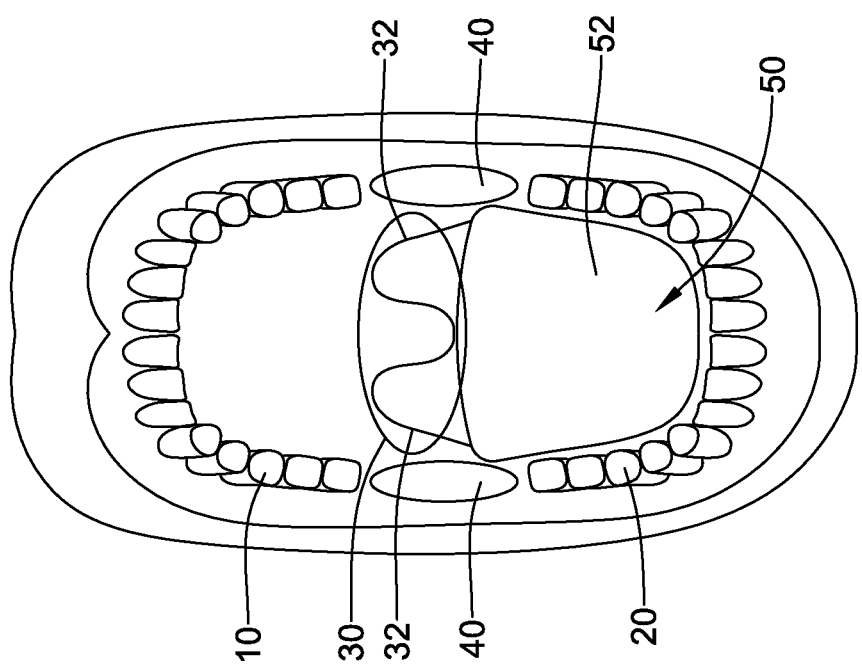
FIG. 2 is a partial front view of mouth anatomy.
Figure 3:
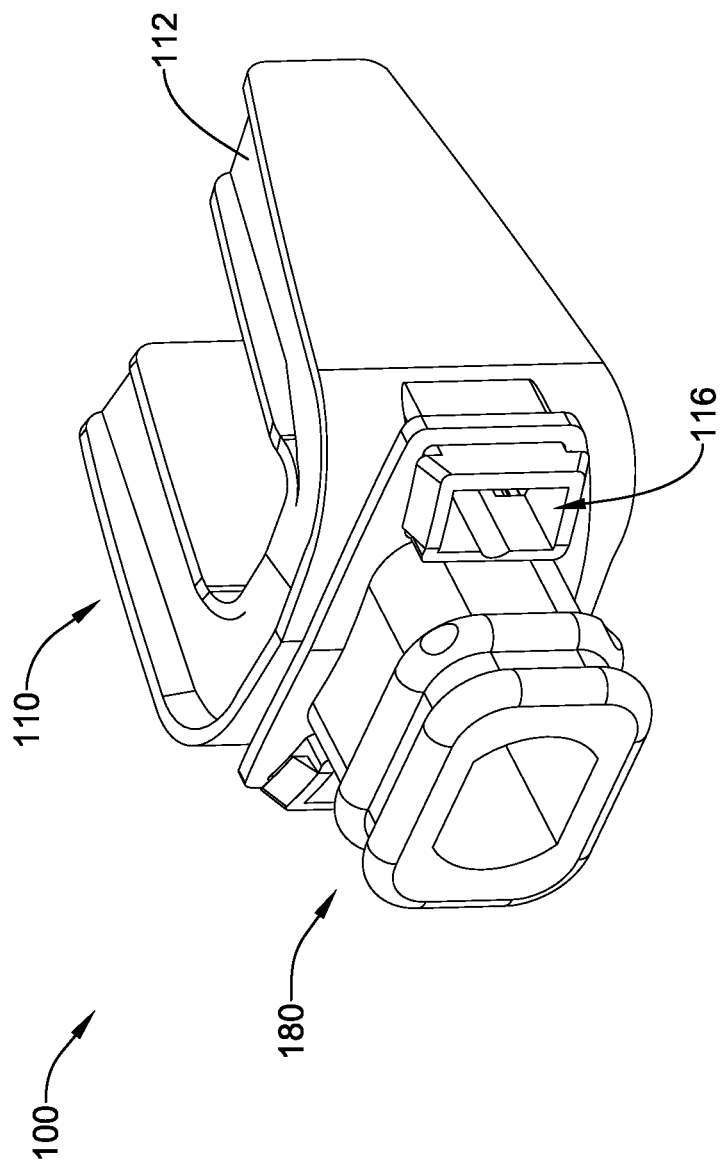
FIG. 3 is a front perspective view of an example mouthpiece.
Figure 4:
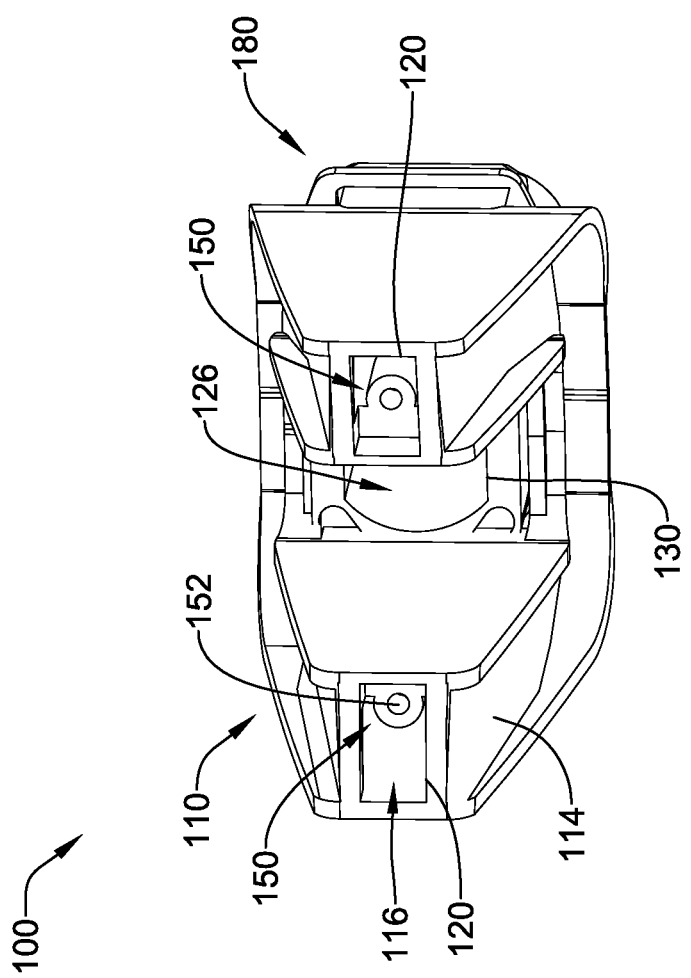
FIG. 4 is a rear perspective view of an example mouthpiece.
Figure 5:
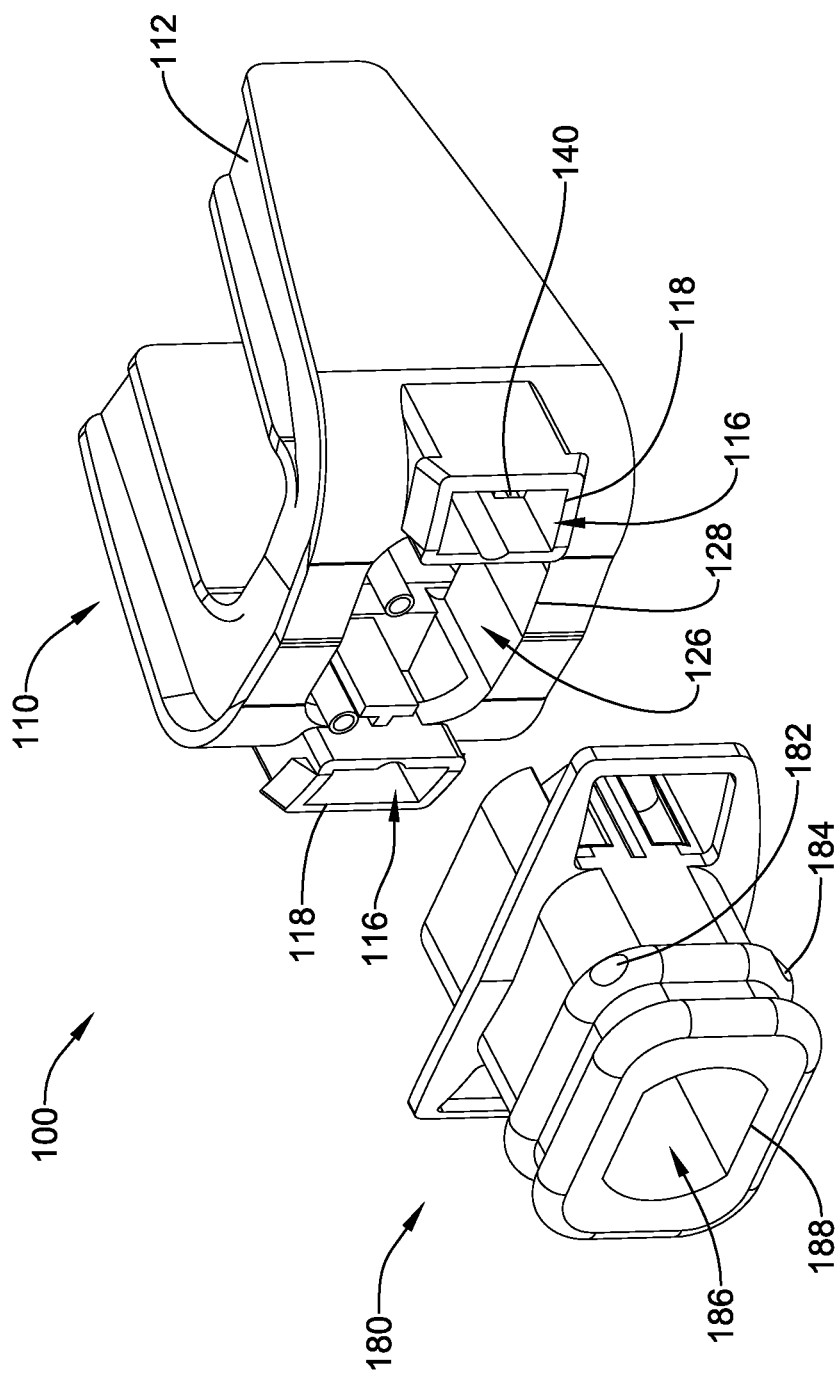
FIG. 5 is a partially exploded perspective view of an example mouthpiece.
Figure 6:
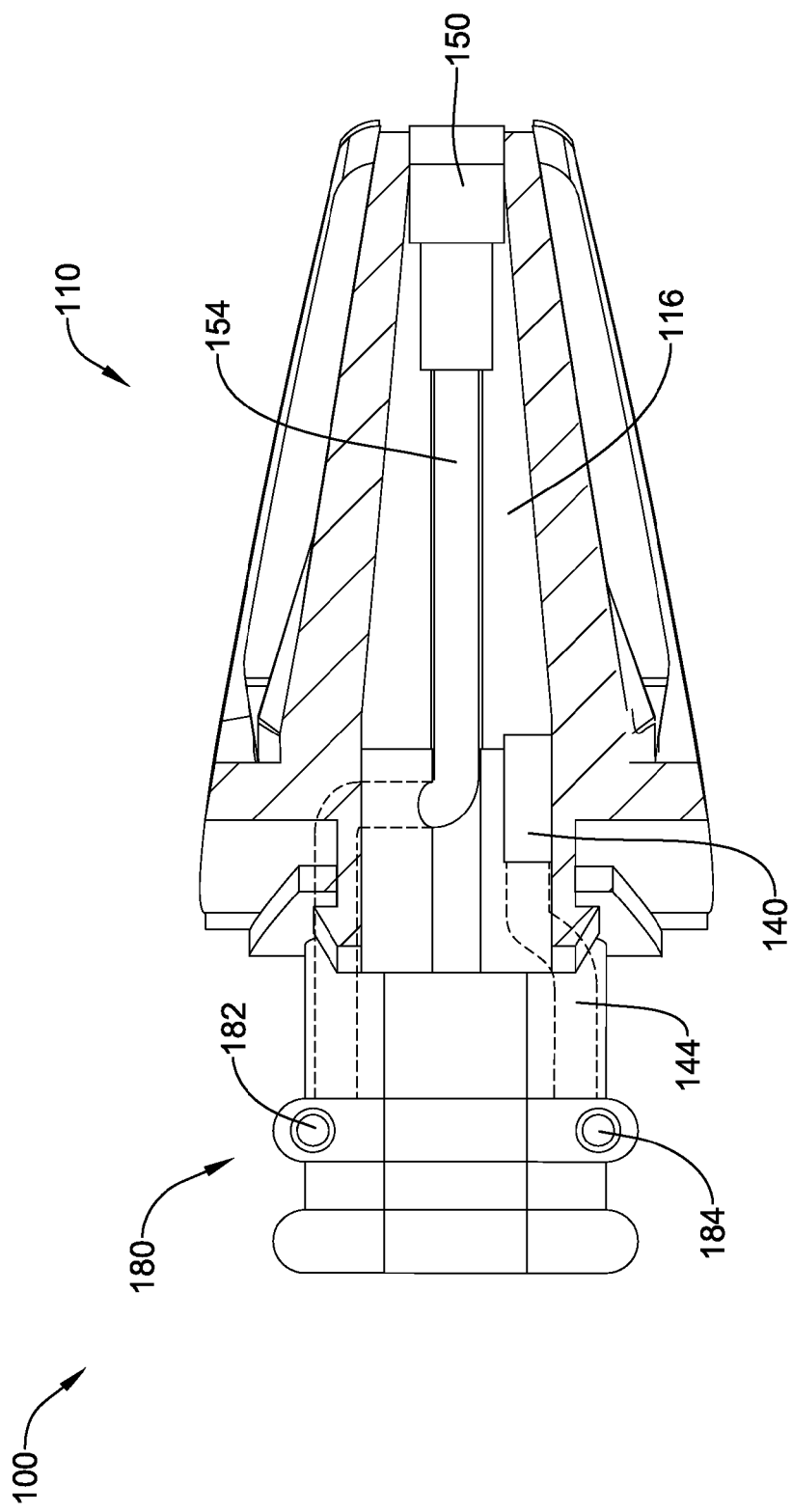
FIG. 6 is a partial cross-sectional side view of an example mouthpiece.
Figure 7:
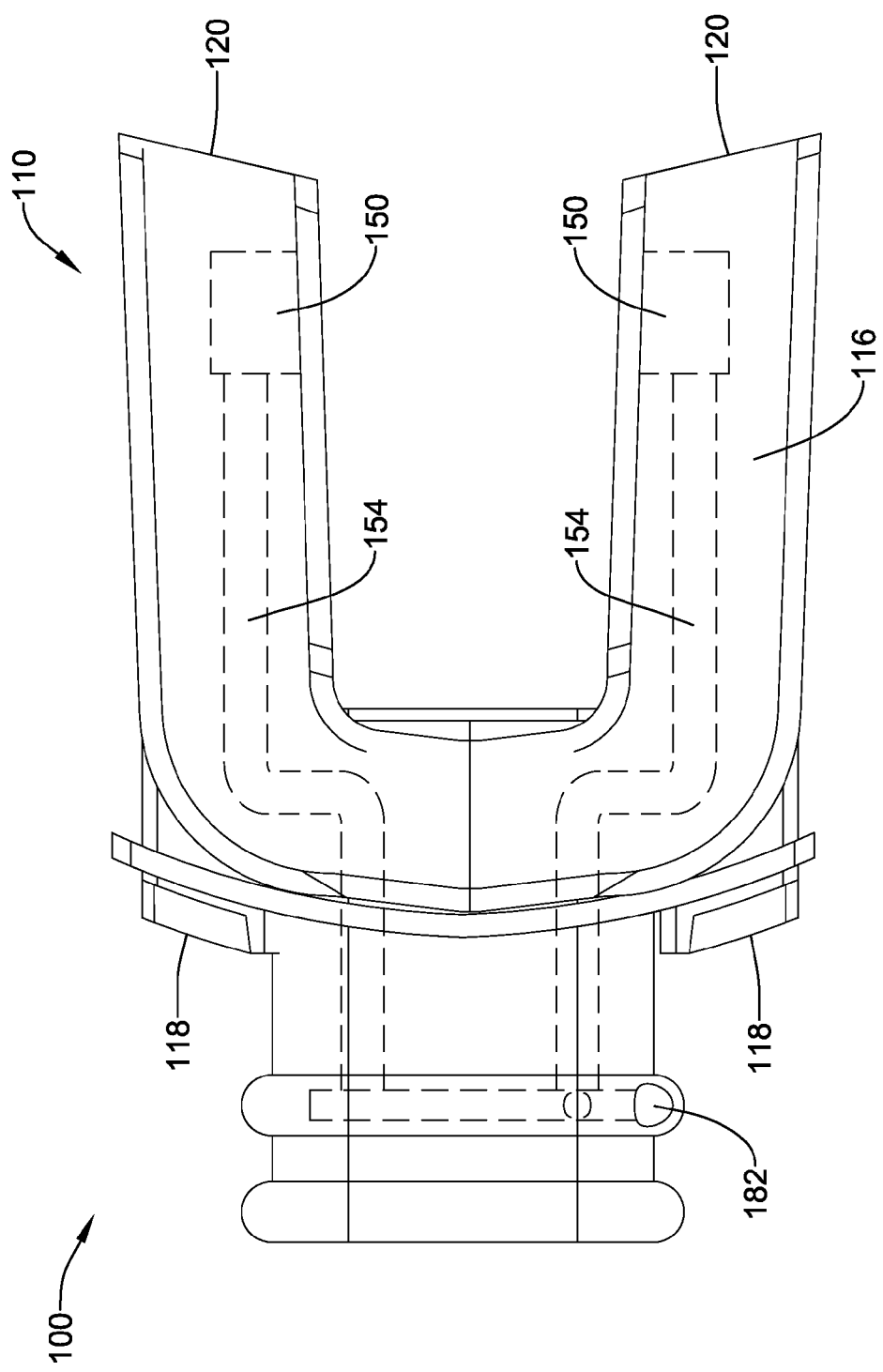
FIG. 7 is a top view of an example mouthpiece.
Figure 8:
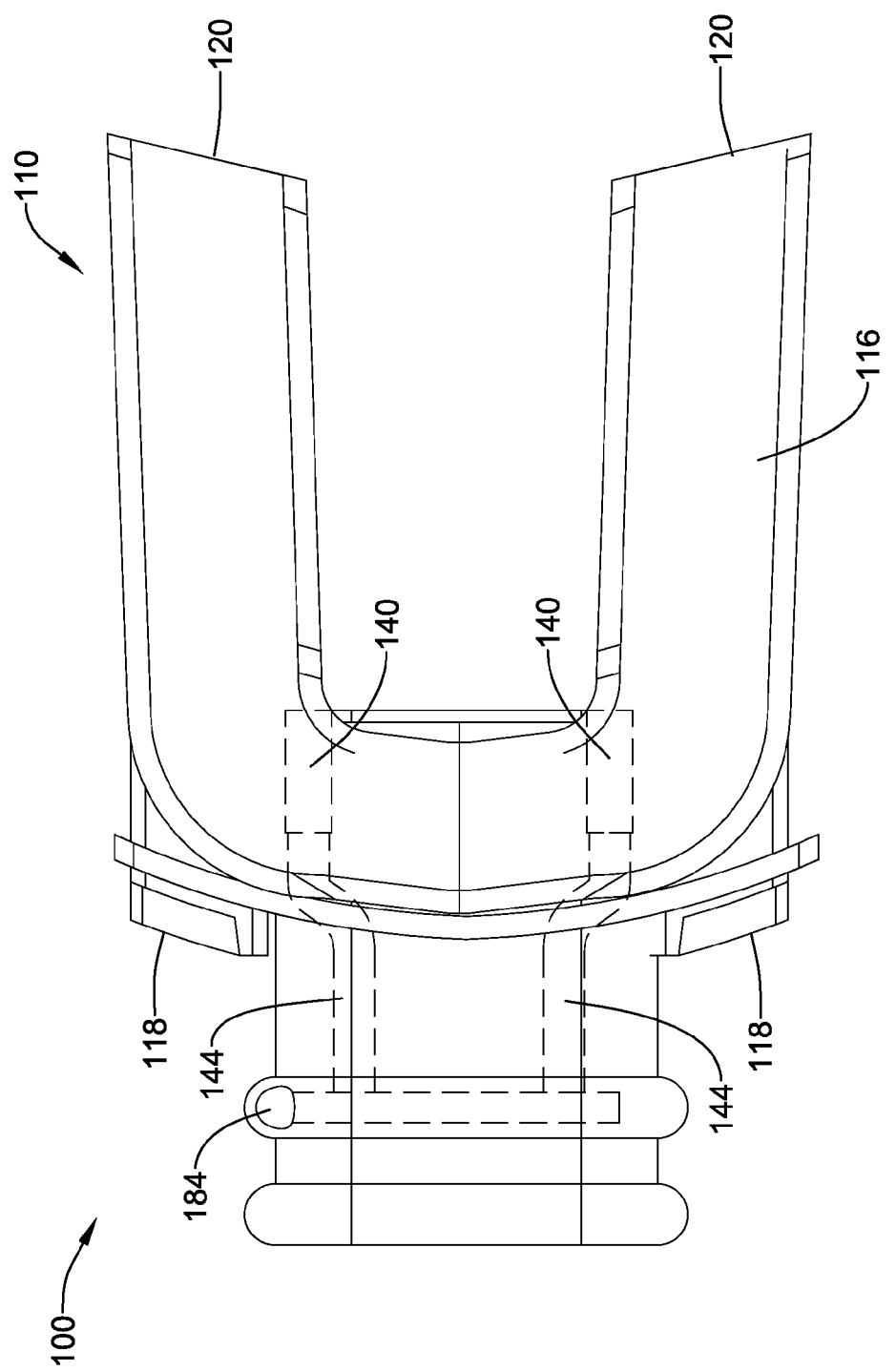
FIG. 8 is a bottom view of an example mouthpiece.

Turning now to the Figures, a partial side view of an example of portions of the anatomy of a patient's mouth may be seen in FIG. 1. The upper and lower jaws may include an upper dentition 10 and a lower dentition 20, respectively. In a normal human mouth, for example, each of the upper dentition 10 and the lower dentition 20 may include four incisors located at the front or anterior portion of the dentition and up to three molars located at a rear or posterior portion of the dentition. The third or most posterior molar may be called the wisdom tooth, and is sometimes removed for various reasons. The dentition may include two canines or cuspids, with one canine located on each side (outside or laterally) of the four incisors. Two premolars or bicuspids may be disposed between the canines and the molars along the dentition. Each dentition forms a generally U-shaped arrangement. The space between the upper dentition 10 and the lower dentition 20 may be referred to as the interocclusal space 40. More specifically, the interocclusal space located between the incisors of the upper dentition 10 and lower dentition 20 may be called the anterior interocclusal space, while the interocclusal space located laterally of the incisors and extending generally anteriorly to posteriorly between the premolars and/or the molars of the upper dentition 10 and the lower dentition 20 may be called the lateral interocclusal space. Generally speaking, the lateral interocclusal space may be bilateral and may accordingly include a left lateral interocclusal space and a right lateral interocclusal space each corresponding to an appropriate side of the patient's anatomy. Located at the rear of the mouth, and disposed on either side of the opening into the throat are the left and right anterior tonsillar pillars 32. The entrance to the throat from the mouth, and the space in the throat at the upper portion of the pharynx may generally be referred to as the oropharynx 30. The rear or posterior wall of the oropharynx is the portion of the throat which may be visibly seen at the back of the throat (behind the uvula) when viewing into a patient's mouth. FIG. 2 illustrates a frontal view of an example of portions of the anatomy of a patient's mouth. In addition to certain features described above with respect to FIG. 1, the oral cavity 50 may be seen in FIG. 2 as the central space between the molars and posterior of the incisors of the lower dentition 20. The oral cavity 50 may extend superiorly from the tongue 52 to the palate or roof of the mouth, and so occupies the central space between the molars and posterior of the incisors of the upper dentition 10 also. As seen in FIG. 2, the interocclusal space 40 includes the vertical (superior-inferior) space formed between the upper dentition 10 and the lower dentition 20 when the jaw is opened.

FIGS. 3-8 illustrate an example medical mouthpiece 100. In some embodiments, the mouthpiece 100 may be generally sized and/or shaped to fit within the anatomy of a patient's mouth. In some embodiments, the mouthpiece 100 may be a single, monolithic, or unitary structure, or may be made of multiple parts and/or components. For example the mouthpiece 100 may include a generally U-shaped first member or portion 110 and a second member or portion 180 attached to the first member 110. The first and second portions may be separate components and/or pieces, as illustrated, but in some embodiments, the first portion or member 110 and the second portion or member 180 may be integrally formed as a single member or piece. In some embodiments, the first member 110 and the second member 180 may be formed as separate pieces and later assembled together to form the mouthpiece 100. The first member 110 may be attached, connected, or otherwise coupled to the second member 180 using any appropriate means including, but not limited to, adhesive bonding, mechanical fastener(s), welding, snap fit, interference fit, friction fit, or other suitable means. In some embodiments, the first member 110 may be detachable from the second member 180.

In some embodiments, the second member 180 may include a first port 182 and a second port 184. The use, function, and structural connectivity of the first port 182 and the second port 184 will become apparent in the discussion below. In some embodiments, the second member 180 may include a central orifice 188 extending therethrough to form a portion 186 of the central passageway extending anteriorly to posteriorly through the mouthpiece 100. In some embodiments, the first member 110 may include an anterior central orifice 128 and a posterior central orifice 130. A portion 126 of the central passageway extends through the anterior portion of the first member 110 from the anterior central orifice 128 to the posterior central orifice 130. When the second member 180 is attached to the first member 110, the portion 186 of the central passageway of the second member 180 cooperates with the portion 126 of the central passageway of the first member 110 to form the complete central passageway extending through the mouthpiece 100. As will be apparent to the skilled artisan, in embodiments where the second member 180 is not present, the central passageway may be formed within the first member 110 alone. The central passageway may be configured to permit access to the oral cavity 50 when the mouthpiece 100 is positioned in the mouth of the patient. With the mouthpiece 100 positioned in the mouth of the patient, the central orifice 188 and/or the anterior central orifice 128 may be positioned exterior to the mouth of the patient, as seen for example in FIG. 9. As such, a medical instrument such as a suction device, an endoscope, an endotracheal tube, etc., for example, may be introduced into the oral cavity 50 through the central passageway as needed or desired.

In some embodiments, the first member or portion 110 may be generally U-shaped and may form or include an upper surface configured to contact the upper dentition 10 of a patient and/or a lower surface configured to contact the lower dentition 20 of a patient. In some embodiments, the upper surface may be spaced apart from the lower surface. In some embodiments, the upper surface forms an upper channel 112 configured to receive the upper dentition 10. In some embodiments, the lower surface forms a lower channel 114 configured to receive the lower dentition 20. An anterior portion of the first member 110 may include a portion of the upper and lower surfaces or channels 112/114 extending transversely (left and/or right from the medial line) between the lateral interocclusal passageways 116 (described in more detail below) to form or act as a bite block configured to be positioned between the incisors of the upper dentition 10 and the lower dentition 20. In some embodiments, the central passageway may terminate at the posterior central orifice 130 proximate a posterior portion of the upper and lower channels 112/114 extending transversely between the left and right lateral interocclusal passageways 116. In some embodiments, the upper surface (or an inferior surface of the upper channel 112) and the lower surface (or a superior surface of the lower channel 114) may angle toward each other in a posterior direction. In other words, the upper surface and the lower surface may be closer together at a posterior portion of the first member 110 than at an anterior portion of the first member 110.

In some embodiments, the first member 110 forms a lateral interocclusal passageway 116 extending from an anterior aperture 118 to a posterior aperture 120. In some embodiments, the upper surface and the lower surface may be spaced apart by the lateral interocclusal passageway 116. In some embodiments, the first member 110 may form two (i.e., left and right) lateral interocclusal passageways 116 configured to be positioned within the lateral interocclusal space(s) 40 and/or disposed on opposing sides of the oral cavity 50. In some embodiments, the lateral interocclusal passageway(s) 116 may be configured to provide a conduit for respiratory gas exchange (i.e., breathing). In at least some such embodiments, the cross-sectional area (i.e., size and/or shape) of the lateral interocclusal passageway(s) 116 may be generally sufficient to allow adequate ventilation to the patient. For example, the interocclusal passageway(s) 116, either each individually and/or collectively, may be dimensioned to have a minimum cross sectional open pathway area in the range of about 15 to about 170 mm$^2$, for example in the range of about 50 to about 150 mm$^2$, for example in the range of about 80 to about 140 mm$^2$. These ranges are believed to provide an adequate fluid pathway or conduit for respiratory gas exchange exclusively through the lateral interocclusal passageway(s) 116 within the device for most patients, but other sizes and/or ranges are contemplated for specific applications, for example, individual patient needs.

Figure 9:
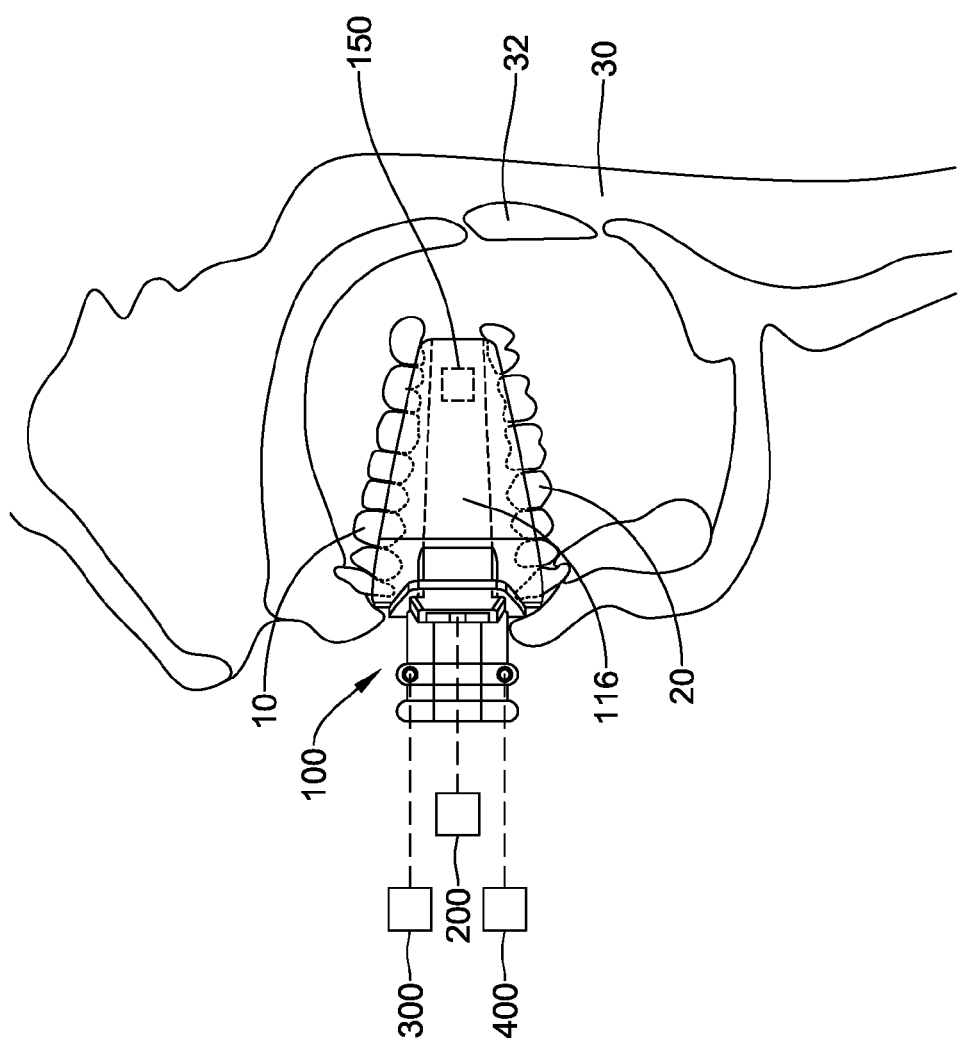
FIG. 9 is a partial side view of an example mouthpiece disposed within mouth anatomy.
Figure 10:
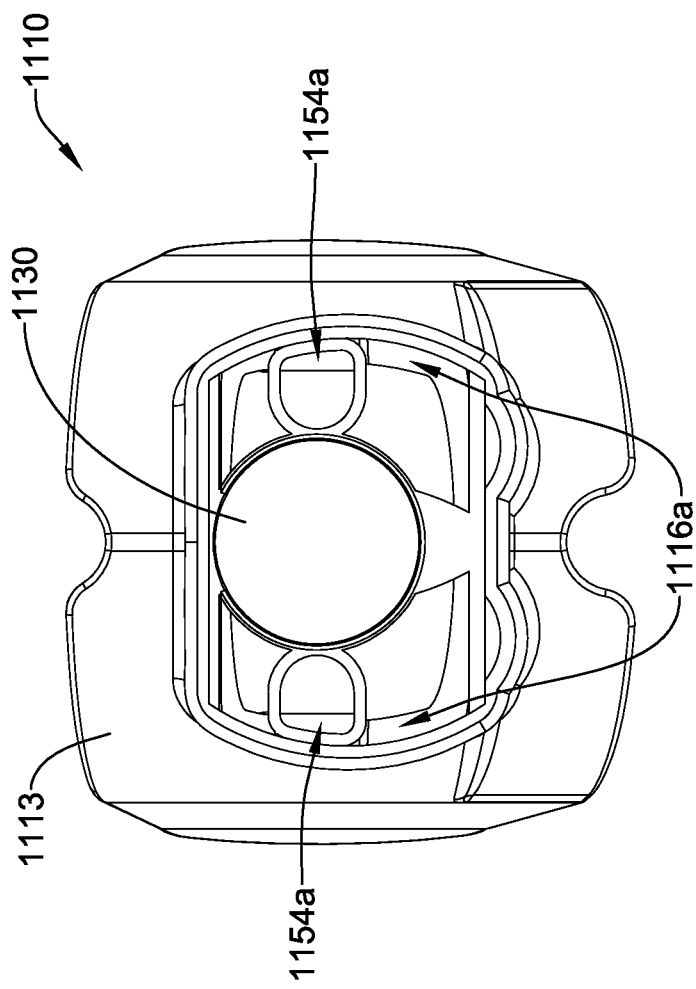
FIG. 10 is a front view of an example U-shaped member.
Figure 11:
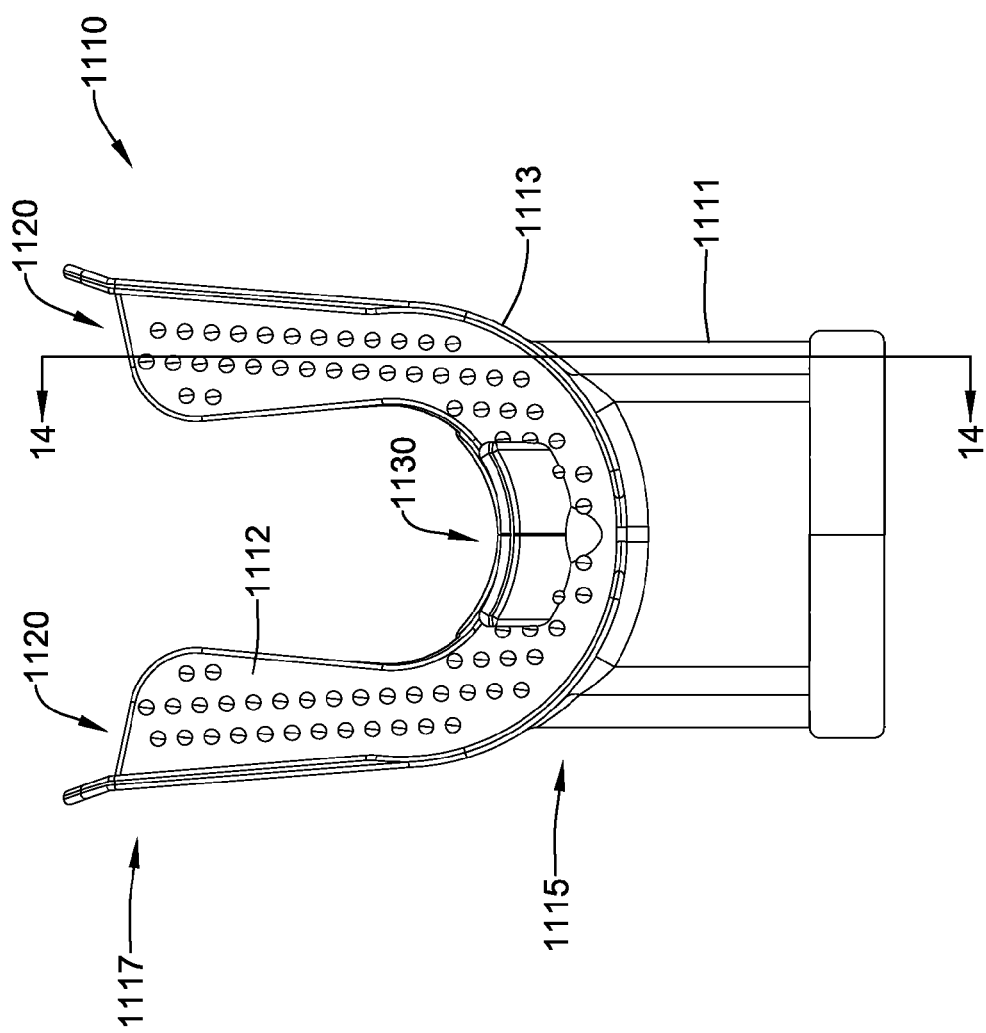
FIG. 11 is a top view of the example U-shaped member of FIG. 10.
Figure 12:
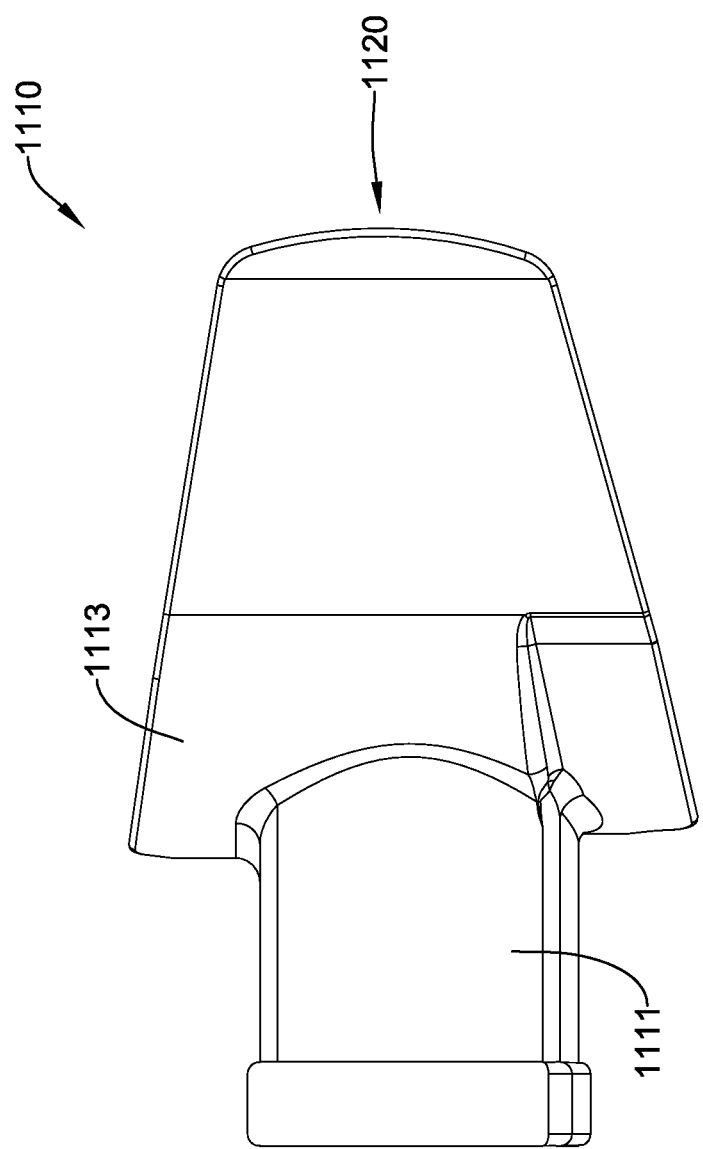
FIG. 12 is a side view of the example U-shaped member of FIG. 10.

In some embodiments, the anterior aperture 118 and/or the lateral interocclusal passageway(s) 116 may be fluidly and/or operatively connected to a ventilator or pressure device 200, for example as seen in FIG. 9, configured to deliver continuous or intermittent positive pressure to the posterior aperture 120, thereby delivering a respiratory gas (e.g., air) to a space adjacent the oropharynx 30 for inspiration by the patient. In some embodiments, when the mouthpiece 100 is positioned in the mouth of the patient, the anterior aperture 118 may be positioned exterior to the mouth of the patient. In some embodiments, the anterior aperture 118 may be configured to connect to known or existing airway connectors and/or devices, such as ventilator equipment, CPAP machines, nebulizers, and the like. In some embodiments having left and right lateral interocclusal passageways 116, the left and right lateral interocclusal passageways 116 may be configured or formed to combine into a single passageway for connection to an external airway connector or device. Similarly, an adapter is contemplated that may connect to both anterior apertures 118 of the left and right lateral interocclusal passageways 116 that may combine or reduce the passageways to a single external conduit with a single external opening or connector.

In some embodiments, the posterior aperture 120 is configured to avoid delivering a gas directly onto the tongue 52 of the patient. In some embodiments, the posterior aperture 120 is configured to avoid delivering a gas directly onto a cheek or directly into the buccal cavity of the patient. In some embodiments, the posterior aperture 120 is configured to deliver a gas through the lateral interocclusal space 40 of the patient. In some embodiments, the posterior aperture 120 is configured to deliver a gas to the posterior oropharynx 30 of the patient without eliciting a gag reflex. In some embodiments, the posterior aperture 120 is configured to deliver a gas to the posterior oropharynx 30 of the patient without stimulating salivation.

In some embodiments, the first member 110 may include a sampling port 150 formed within a posterior portion of the lateral interocclusal passageway(s) 116. In embodiments having more than one lateral interocclusal passageway 116, each lateral interocclusal passageway 116 may include a sampling port 150 and orifice 152 (i.e., a left lateral interocclusal sampling port and a right lateral interocclusal sampling port) formed therein. The sampling port 150 may include a sampling orifice 152 facing in a posterior direction toward the posterior aperture 120. In other embodiments, the port 150 may be facing in other directions, such as angled or facing laterally, medially, superiorly, inferiorly, or the like, or any combination thereof or angle desired. In some embodiments, the sampling port 150 and orifice 152 may be recessed from the posterior aperture 120 within the lateral interocclusal passageway 116. In some embodiments, the sampling port 150 may be generally flush with or otherwise positioned at or within the posterior aperture 120. In some embodiments, the sampling port 150 and/or the sampling orifice 152 may include a covering or valve disposed thereon. The covering or valve may be gas permeable to permit respiratory gases, for example inhaled or exhaled respiratory gases, to pass therethrough, while being liquid impermeable to prevent liquids such as saliva or other oral secretions from entering the sampling port 150 and/or the sampling orifice 152. In some embodiments, the first member 110 may be configured to position the posterior aperture 120 and/or the sampling port 150 between a posterior edge of the second molar and the anterior tonsillar pillar 32, as may be seen in FIG. 9 for example.

In some embodiments, the sampling port 150 may be in fluid communication with and/or fluidly connected to a first port 182 and/or an analyzing apparatus 300 by a sampling conduit 154. In other words, the analyzing apparatus 300 may be operatively connected to the first port 182 and/or the sampling port 150, as seen for example in FIG. 9. In some embodiments, the sampling conduit 154 may include a discrete tubular member embedded or molded within the first member 110, a passageway or lumen integrally formed or molded within the first member 110, and/or a combination thereof. In some embodiments, the sampling conduit 154 may extend externally of the mouthpiece 100, either as an integral element or as a separate tubing or conduit element fluidly connected to the first port 182, to the analyzing apparatus 300. The analyzing apparatus 300 may be any suitable apparatus known in the art for analyzing and/or monitoring respiratory gases, for example inhaled or exhaled respiratory gases, for, but not limited to, partial pressure and/or concentration of respiratory gases such as carbon dioxide (CO2), oxygen (O2), nitrous oxide (N2O), and/or anesthetic gases (e.g., sevoflurane, desflurane, isoflurane, etc.), including but not limited to, carbon dioxide (CO2) partial pressure and/or end tidal carbon dioxide (ETCO2) concentration, for example. In some embodiments, the analyzing apparatus 300 may compare, plot, chart, or otherwise record data such as, for example, carbon dioxide (CO2) partial pressure and/or carbon dioxide (CO2) concentration as a function of time and/or volume.

In some embodiments, the first port 182 may be formed in the second member 180. While not expressly shown, in some embodiments, the first port 182 may be formed in the first member 110. In some embodiments, there may be no first port 182, and the sampling conduit 154 may extend directly from the sampling port 150 to the analyzing apparatus 300. In some embodiments, the first port 182 may act or function as a connector between a portion of the sampling conduit 154 disposed internal to the mouthpiece 100 and a separate, external portion of the sampling conduit 154, for example a section of tubular hose connecting the analyzing apparatus 300 to the first port 182.

In some embodiments, the first member 110 may include a supply orifice 140 formed within the lateral interocclusal passageway 116 and a supplemental gas conduit 144 in fluid communication with and/or fluidly connected to a second port 184 and/or a source of supplemental gas 400, for example, oxygen, nitrous oxide, an aerosolized pharmaceutical, or other suitable gas. In other words, the source of supplemental gas 400 may be operatively connected to the second port 184 and/or the supply orifice 140, as seen for example in FIG. 9. In embodiments having more than one lateral interocclusal passageway 116, each lateral interocclusal passageway 116 may include a supply orifice 140 (i.e., a left lateral interocclusal supply orifice and a right lateral interocclusal supply orifice) formed therein. In some embodiments, the supply orifice 140 may be configured to deliver a supplemental gas into the lateral interocclusal passageway 116. As the supplemental gas is delivered to the supply orifice 140, the supplemental gas mixes with the air or gas being delivered through the lateral interocclusal passageway(s) 116 to a space adjacent the patient's oropharynx. In some embodiments, the supplemental gas may be delivered at a flow rate of about 0.1 liters per minute to about 15 liters per minute.

In some embodiments, the first member 110 may include both a supply orifice 140 and a sampling port 150, along with any additional structure associated with each (i.e., the supplemental gas conduit 144, the sampling conduit 154, etc.). In these embodiments, the supply orifice 140 is disposed or located anteriorly of the sampling port 150. Using this arrangement or configuration, supplemental gas can be delivered to the lateral interocclusal passageway for inspiration by the patient without diluting exhaled respiratory gases being collected at the sampling port 150. As the patient exhales, exhaled respiratory gases are expelled through the lateral interocclusal passageway 116 in a posterior to anterior direction, and any supplemental gas flowing through the supply orifice 140 is expelled away from the sampling port with the exhaled respiratory gases. As such, exhaled respiratory gases may be collected at the sampling port 150 which are not diluted by the supplemental gas.

In some embodiments, certain features of the above described embodiment(s) may be defined, described, or characterized according to one or more of the following aspects:

1. A medical mouthpiece, comprising:

a generally U-shaped member forming an upper surface configured to contact an upper dentition of a patient spaced apart from a lower surface configured to contact a lower dentition of the patient;

wherein the U-shaped member forms a lateral interocclusal space extending from an anterior aperture to a posterior aperture between the upper surface and the lower surface.

2. The medical mouthpiece of aspect 1, further comprising:

a sampling port formed within a posterior portion of the lateral interocclusal space the sampling port configured to be positioned in a posterior portion of the lateral interocclusal space of the patient; and a sampling conduit for fluid communication between the sampling port and an analyzing apparatus configured to analyze inhaled or exhaled respiratory gases.

3. The medical mouthpiece of aspect 1 or 2, further comprising: a supplemental gas conduit for fluid communication between a source of supplemental gas and a supply orifice within the lateral interocclusal space.

4. A medical mouthpiece, comprising:

a generally U-shaped member forming an upper surface configured to contact an upper dentition of a patient spaced apart from a lower surface configured to contact a lower dentition of the patient;

a sampling port formed within a posterior portion of the generally U-shaped member, the sampling port having a sampling orifice recessed within the posterior portion; and a sampling conduit for fluid communication between the sampling port and an analyzing apparatus configured to analyze inhaled or exhaled respiratory gases.

5. The medical mouthpiece of aspect 4, wherein the sampling port is configured to be positioned in a posterior portion of a lateral interocclusal space of the patient.

6. A medical mouthpiece, comprising:

a generally U-shaped member forming an upper surface configured to contact an upper dentition of a patient spaced apart from a lower surface configured to contact a lower dentition of the patient; and a supplemental gas conduit for fluid communication between a source of supplemental gas and a supply orifice formed in the generally U-shaped member.

7. The medical mouthpiece of aspect 6, wherein the supply orifice is configured to be positioned in an anterior portion of the lateral interocclusal space of the patient.

8. A medical mouthpiece, comprising:

a generally U-shaped member forming an upper surface configured to contact an upper dentition of a patient spaced apart from a lower surface configured to contact a lower dentition of the patient;

wherein the U-shaped member forms a lateral interocclusal passageway extending from an anterior aperture to a posterior aperture between the upper surface and the lower surface, the lateral interocclusal passageway configured to provide a conduit for respiratory gas exchange;

a sampling port formed within a posterior portion of the lateral interocclusal passageway, the sampling port configured to be positioned in a posterior lateral interocclusal space of the patient;

a sampling conduit for fluid communication between the sampling port and an analyzing apparatus configured to analyze inhaled or exhaled respiratory gases; and a supplemental gas conduit for fluid communication between a source of supplemental gas and a supply orifice within the lateral interocclusal passageway.

9. The medical mouthpiece of any of aspects 1-8, wherein the U-shaped member forms a central passageway extending from a central anterior orifice to a central posterior orifice;

wherein when the medical mouthpiece is positioned in a mouth of the patient, the central passageway permits access to an oral cavity of the patient for the introduction of a medical instrument therein.

10. The medical mouthpiece of any of aspects 1-3 or 8, wherein the U-shaped member forms two lateral interocclusal passageways therein, the two lateral interocclusal passageways configured to be disposed on opposing sides of an oral cavity of the patient.

11. The medical mouthpiece of aspect 8, wherein the supply orifice is disposed anteriorly of the sampling port.

12. The medical mouthpiece of any of aspects 1-3, 8, or 10 wherein the U-shaped member is configured to position the posterior aperture of the lateral interocclusal passageway between a posterior edge of a second molar and an anterior tonsillar pillar of the patient.

13. The medical mouthpiece of aspect 12, wherein the posterior aperture of the interocclusal passageway is configured to avoid delivering a gas directly onto a tongue of the patient.

14. The medical mouthpiece of aspect 12, wherein the posterior aperture of the inter-occlusal passageway is configured to avoid delivering a gas directly onto a cheek of the patient.

15. The medical mouthpiece of aspect 12, wherein the posterior aperture is configured to deliver a gas to an oropharynx of the patient without eliciting a gag reflex.

16. The medical mouthpiece of aspect 12, wherein the posterior aperture is configured to deliver a gas to an oropharynx of the patient without stimulating salivation.

17. The medical mouthpiece of any of aspects 1-3, 8, 10, or 12 wherein when the medical mouthpiece is positioned in a mouth of the patient, the anterior aperture is positioned exterior to the mouth of the patient.

18. The medical mouthpiece of any of aspects 1-3, 8, 10, 12, or 17 wherein the anterior aperture is configured to connect to respiratory equipment.

19. The medical mouthpiece of any of aspects 1-18, wherein the upper surface forms an upper channel configured to receive the upper dentition of the patient.

20. The medical mouthpiece of any of aspects 1-19, wherein the lower surface forms a lower channel configured to receive the lower dentition of the patient.

21. A medical mouthpiece, comprising:

a generally U-shaped member forming an upper surface configured to contact an upper dentition of a patient spaced apart from a lower surface configured to contact a lower dentition of the patient;

wherein the U-shaped member forms a lateral interocclusal passageway extending from an anterior aperture to a posterior aperture along an axis defined by a line between the upper dentition and the lower dentition, the lateral interocclusal passageway configured to provide a conduit for respiratory gas exchange;

a sampling port formed within a posterior portion of the lateral interocclusal passageway;

a sampling conduit fluidly connecting the sampling port and an analyzing apparatus configured to analyze inhaled or exhaled respiratory gases collected adjacent an oropharynx of the patient; and a supplemental gas conduit fluidly connecting a source of supplemental gas and a supply orifice within the lateral interocclusal passageway.

22. The medical mouthpiece of aspect 21, wherein the upper surface forms an upper channel configured to receive the upper dentition of the patient.

23. The medical mouthpiece of aspect 21, wherein the lower surface forms a lower channel configured to receive the lower dentition of the patient.

24. The medical mouthpiece of aspect 21, wherein the supply orifice is configured to deliver supplemental gas into the lateral interocclusal passageway for inspiration.

25. The medical mouthpiece of aspect 24, wherein the supplemental gas is delivered at a flow rate of about 0.1 liters per minute to about 15 liters per minute.

26. The medical mouthpiece of aspect 21, wherein the supply orifice is disposed anteriorly of the sampling port.

27. The medical mouthpiece of aspect 21, wherein the lateral interocclusal passageway is fluidly connected to a ventilator or pressure device configured to deliver continuous or intermittent positive pressure to the posterior aperture.

28. The medical mouthpiece of aspect 21, wherein the lateral interocclusal passageway is sized and configured to allow adequate ventilation to the patient.

29. The medical mouthpiece of aspect 21, wherein the analyzing apparatus is configured to monitor respiratory gas partial pressure or end tidal carbon dioxide (ETCO2) concentration in the exhaled respiratory gases.

30. A medical mouthpiece, comprising:

a generally U-shaped first member forming an upper channel spaced apart from a lower channel with left and right lateral interocclusal passageways formed therebetween, the left and right lateral interocclusal passageways extending from an anterior portion of the first member through a posterior portion of the first member, and a first central orifice extending through the anterior portion;

wherein the first member is shaped and configured to receive an upper dentition of a patient in the upper channel or a lower dentition of a patient in the lower channel; and a second member attached to the anterior portion, the second member including a second central orifice extending through the second member and in communication with the first central orifice to form a central passageway extending through the mouthpiece;

wherein the second member includes a first port and a second port formed therein;

the first port being fluidly connected to a left lateral interocclusal sampling port and a right lateral interocclusal sampling port for sampling expiration gases, the left and right lateral interocclusal sampling ports being disposed within the left and right inter-occlusal passageways, respectively, proximate the posterior portion;

the second port being fluidly connected to the left and right lateral interocclusal passageways for delivery of a supplemental gas into the left and right lateral interocclusal passageways.

31. The medical mouthpiece of aspect 30, wherein the first port is fluidly connected to the left and right lateral interocclusal sampling ports by a left sampling conduit and a right sampling conduit, respectively.

32. The medical mouthpiece of aspect 31, wherein the first port is fluidly connected to a respiratory gas sampling apparatus configured to collect and analyze inhaled or exhaled respiratory gas.

33. The medical mouthpiece of aspect 30, wherein the second port is fluidly connected to the left and right lateral interocclusal passageways by a left supplemental gas conduit and a right supplemental gas conduit, respectively.

34. The medical mouthpiece of aspect 33, wherein the second port is fluidly connected to a source of supplemental gas for inspiration.

35. The medical mouthpiece of aspect 30, wherein a posterior opening of the central passageway terminates proximate a posterior portion of the upper and lower channels extending transversely between the left and right lateral interocclusal passageways.

36. The medical mouthpiece of aspect 30, wherein an inferior surface of the upper channel and a superior surface of the lower channel angle toward each other in a posterior direction.

37. A method for delivering a gas to a patient, the method comprising:

inserting a mouthpiece into a mouth of a patient, the mouthpiece having a generally U-shaped member forming a lateral interocclusal passageway extending posteriorly between an upper dentition and a lower dentition of the patient; and delivering a gas to the patient through the lateral interocclusal passageway such that the gas is delivered through a posterior aperture to a space adjacent the patient's oropharynx.

38. The method of aspect 37, wherein the mouthpiece includes a supplemental gas conduit in fluid communication with the lateral interocclusal passageway, and the method further includes: delivering a supplemental gas through the supplemental gas conduit and into the lateral interocclusal passageway, the supplemental gas mixing with the gas and being delivered to the patient's posterior oropharynx.

39. The method of aspect 37 or 38, wherein the mouthpiece includes a sampling port disposed within a posterior portion of the lateral interocclusal passageway, and a sampling conduit fluidly connecting the sampling port to an analyzing apparatus, and the method further includes:

collecting a sample of inhaled or exhaled respiratory gases at the sampling port; and analyzing the sample for respiratory gas partial pressure or carbon dioxide (CO2) concentration.

40. The method of aspect 39, further including: plotting the respiratory gas partial pressure or carbon dioxide (CO2) concentration as a function of time or volume.

41. The medical mouthpiece of any of aspects 2, 4, 8, or 21, wherein the sampling port includes a covering disposed thereon, the covering being impermeable to liquid and permeable to gas.

42. The medical mouthpiece of aspect 30, wherein the left and right lateral interocclusal sampling ports each include a covering disposed thereon, the covering being impermeable to liquid and permeable to gas.

43. The medical mouthpiece of any of aspects 1-5, wherein the lateral interocclusal space is configured to provide a conduit for respiratory gas exchange.

44. The medical mouthpiece of any of aspects 1-5 or 43, wherein the lateral interocclusal space is configured to provide a conduit for supplemental gas delivery.

45. The medical mouthpiece of any of aspects 1-5 or 43-44, wherein the lateral interocclusal space is configured to provide a conduit for delivery of continuous pressure.

46. The medical mouthpiece of any of aspects 1-5 or 43-45, wherein the lateral interocclusal space is configured to provide a conduit for delivery of intermittent pressure.

47. The medical mouthpiece of any of aspects 1-5 or 43-46, wherein the lateral interocclusal space is configured to provide a fluid passageway extending from the anterior aperture to the posterior aperture.

48. The medical mouthpiece of any of aspects 2, 8, or 21, wherein the sampling port has a sampling orifice.

49. The medical mouthpiece of aspect 4 or 48, wherein the sampling orifice is facing in a posterior direction.

50. The medical mouthpiece of aspect 4 or 48, wherein the sampling orifice is facing in a direction that is other than a posterior direction.

51. The medical mouthpiece of aspect 18, wherein the respiratory equipment is selected from a ventilator, an anesthesia circuit, a CPAP device, a BiPAP device, a rescue bag valve device, or combinations thereof.

52. A method for sampling inhaled or exhaled respiratory gases of a patient, the method comprising:
  inserting a mouthpiece into a mouth of a patient, the mouthpiece having a generally U-shaped member forming a lateral interocclusal passageway extending posteriorly between an upper dentition and a lower dentition of the patient;
  collecting a sample of inhaled or exhaled respiratory gases through at least a portion of the interocclusal passageway; and
  analyzing the sample.

53. The method of aspect 52, wherein the analyzing step includes analyzing for respiratory gas partial pressure or end tidal carbon dioxide (ETCO2) concentration.

54. The method of aspect 52 or 53, wherein the mouthpiece includes a supplemental gas conduit in fluid communication with the lateral interocclusal passageway, and the method further includes: delivering a supplemental gas through the supplemental gas conduit and into the lateral interocclusal passageway.

55. The method of any of aspects 52-54, wherein the mouthpiece includes a sampling port disposed within a posterior portion of the lateral interocclusal passageway, and a sampling conduit fluidly connecting the sampling port to an analyzing apparatus, and the method further includes: collecting a sample of inhaled or exhaled respiratory gases at the sampling port.

Figure 25:
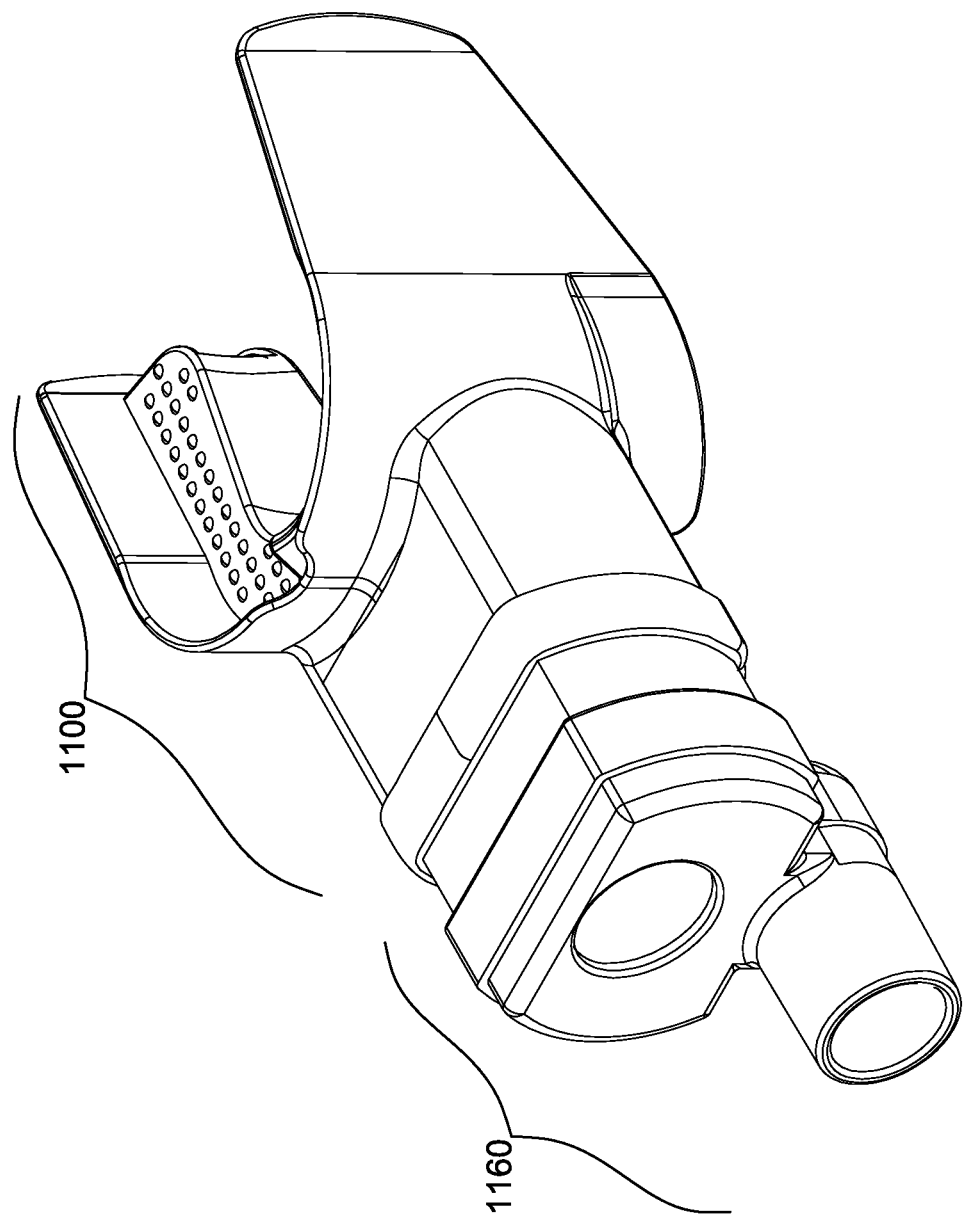
FIG. 25 is a perspective view of an example mouthpiece assembly.
Figure 26:
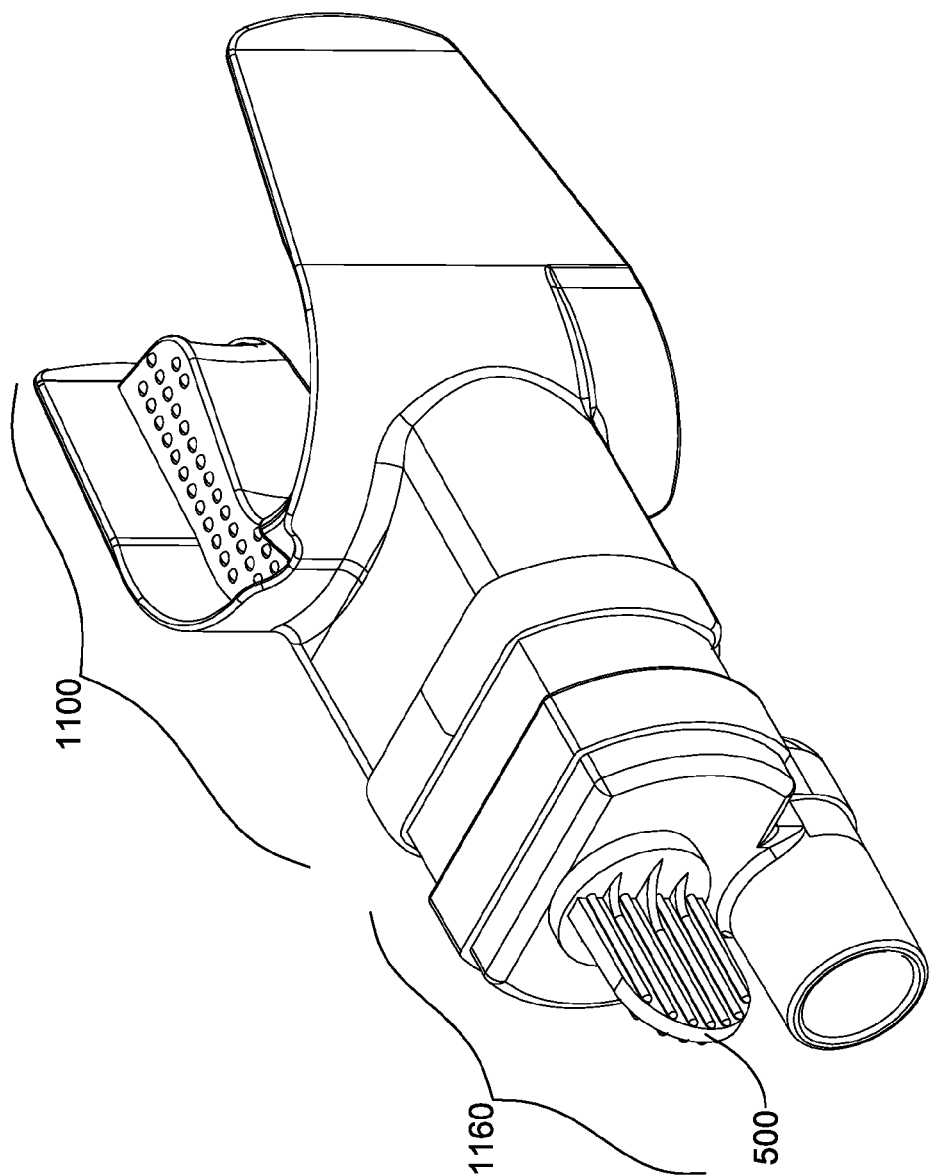
FIG. 26 is a perspective view of an example mouthpiece assembly.
Figure 27:
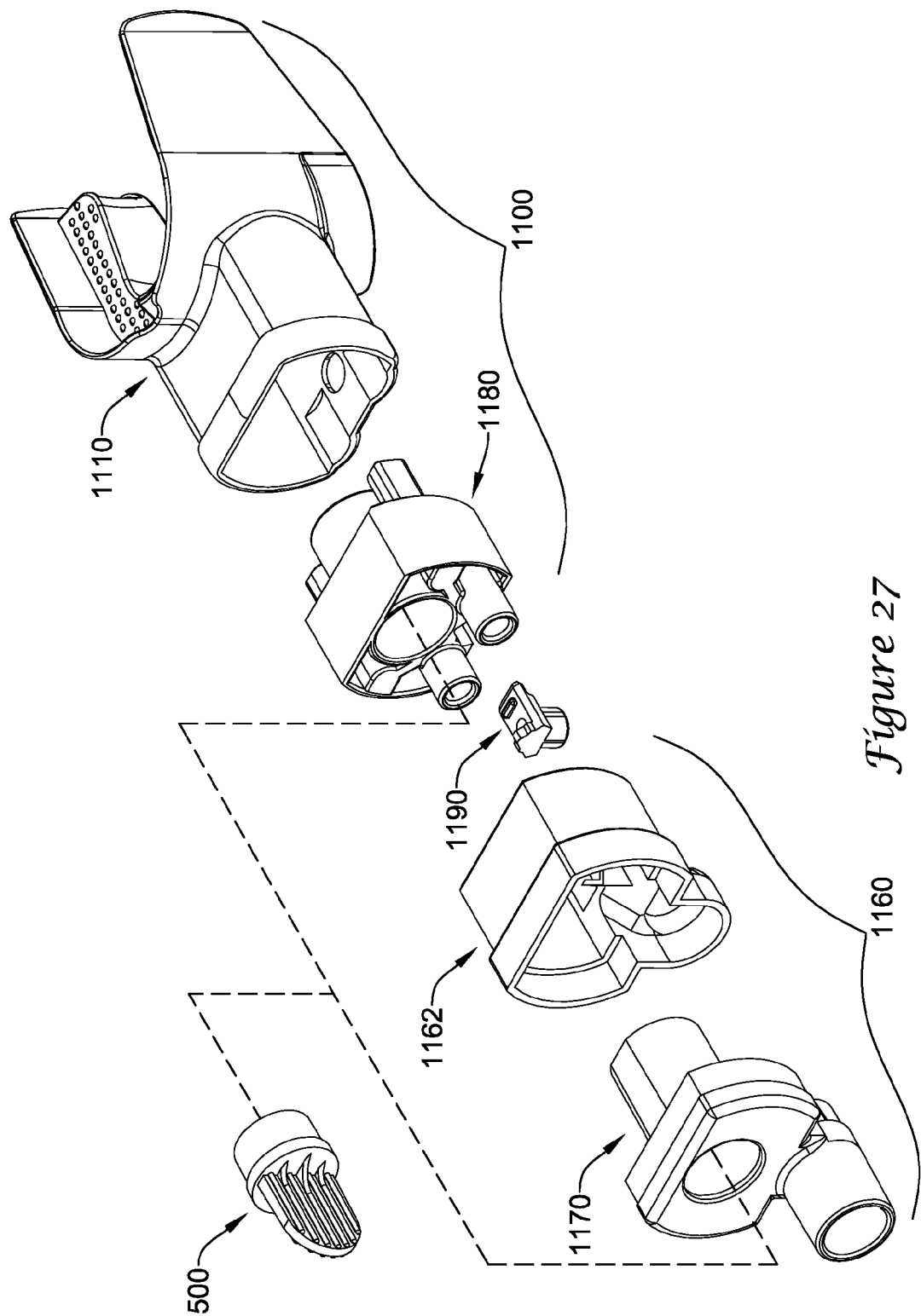
FIG. 27 is a partially exploded perspective view of an example mouthpiece assembly.

In some embodiments, a medical mouthpiece 1100 may include a generally U-shaped first member 1110 having a tubular portion 1111 extending anteriorly therefrom and defining a first cavity, and a second member 1180, as seen in FIGS. 25-27, for example. In some embodiments, the U-shaped first member 1110 may include a curved base and a pair of spaced-apart arms extending away from the curved base. In some embodiments, the tubular portion 1111 may extend anteriorly from the curved base. In some embodiments, the pair of spaced-apart arms may extend posteriorly from the curved base. In some embodiments, the first member 1110 (shown illustratively in FIGS. 10-14) may include an upper surface 1112 shaped and configured to receive and/or contact an upper dentition 10 of a patient. In some embodiments, the first member 1110 may include a lower surface 1114 shaped and configured to receive and/or contact a lower dentition 20 of a patient.

In some embodiments, the first member 1110 may include a flange 1113 extending superiorly from the upper surface 1112 and/or inferiorly from the lower surface 1114 at an outer perimeter or edge of the upper surface 1112 and/or the lower surface 1114. In use, the flange 1113 may be positioned with the upper dentition 10 and lower dentition 20 on a posterior side of the flange 1113 and the lips of the patient on an anterior side of the flange 1113. Accordingly, in some embodiments, the first member 1110 and/or the flange 1113 may be made from a generally soft, flexible material such as those disclosed herein, so as to avoid injury to the lips and/or gums of the patient and/or to improve comfort. In some embodiments, the upper surface 1112 and/or the lower surface 1114 may be made from a material that is less flexible and more rigid than the flange 1113. In some embodiments, the upper surface 1112 and/or the lower surface 1114 may be made from a material that is more flexible and less rigid than the flange 1113. In some embodiments, the upper surface 1112 and/or the lower surface 1114 may be made from the same material as the flange 1113, with substantially similar flexibility characteristics.

In some embodiments, an anterior portion 1115 of the generally U-shaped first member 1110 may include a portion of the upper surface 1112 and a portion of the lower surface 1114 extending transversely (left and/or right from the medial line) between the pair of arms to form or act as a bite block configured to be positioned between the incisors of the upper dentition 10 and the lower dentition 20. In some embodiments, the anterior portion 1115 may form or include the curved base of the first member 1110. The bite block, which may be further supported by the second member 1180 as described below, may prevent a patient from biting down (intentionally or unintentionally/involuntarily) and partially or fully closing off any of the passageways of the mouthpiece 1100 described herein. In some embodiments, the portion of the upper surface 1112 at the anterior portion 1115 of the U-shaped first member 1110 may include an angled ramp element along a posterior edge of the upper surface 1112, the ramp element extending superiorly from the upper surface 1112 in a posterior direction. In use, the ramp element may be positioned behind the upper dentition 10 to aid in retaining the mouthpiece 1100 in the patient's mouth. Similarly, in some embodiments, the portion of the lower surface 1114 at the anterior portion 1115 of the U-shaped first member 1110 may include a raised ridge element along a posterior edge of the lower surface 1114, the raised ridge extending inferiorly from the lower surface 1114. In use, the raised ridge may be positioned behind the lower dentition 20 to aid in retaining the mouthpiece 1100 in the patient's mouth.

Figure 13:
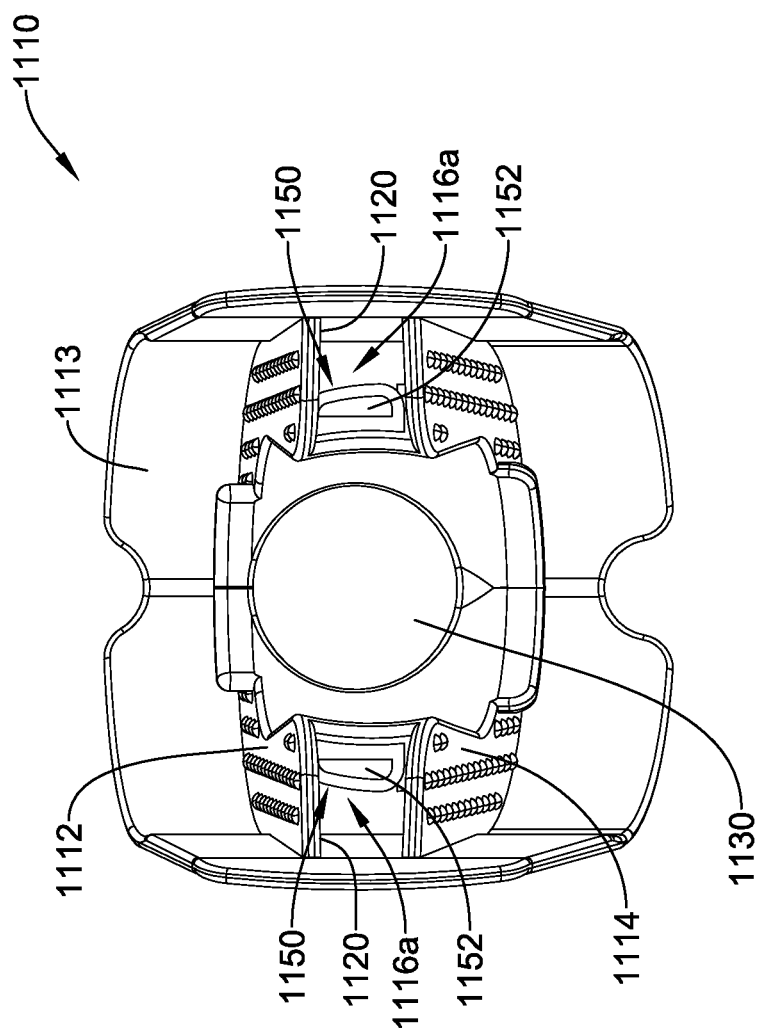
FIG. 13 is a back view of the example U-shaped member of FIG. 10.
Figure 14:
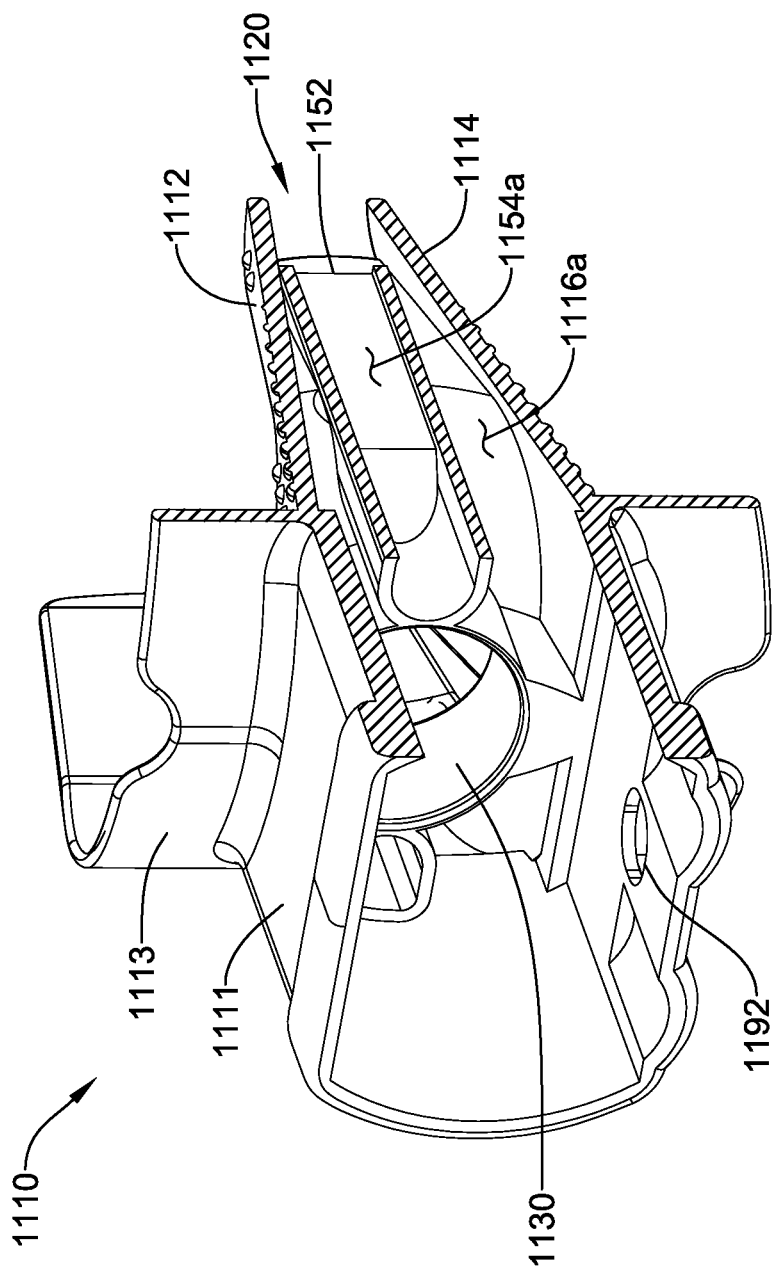
FIG. 14 is a partial cross-sectional perspective view of the example U-shaped member of FIG. 10.
Figure 15:
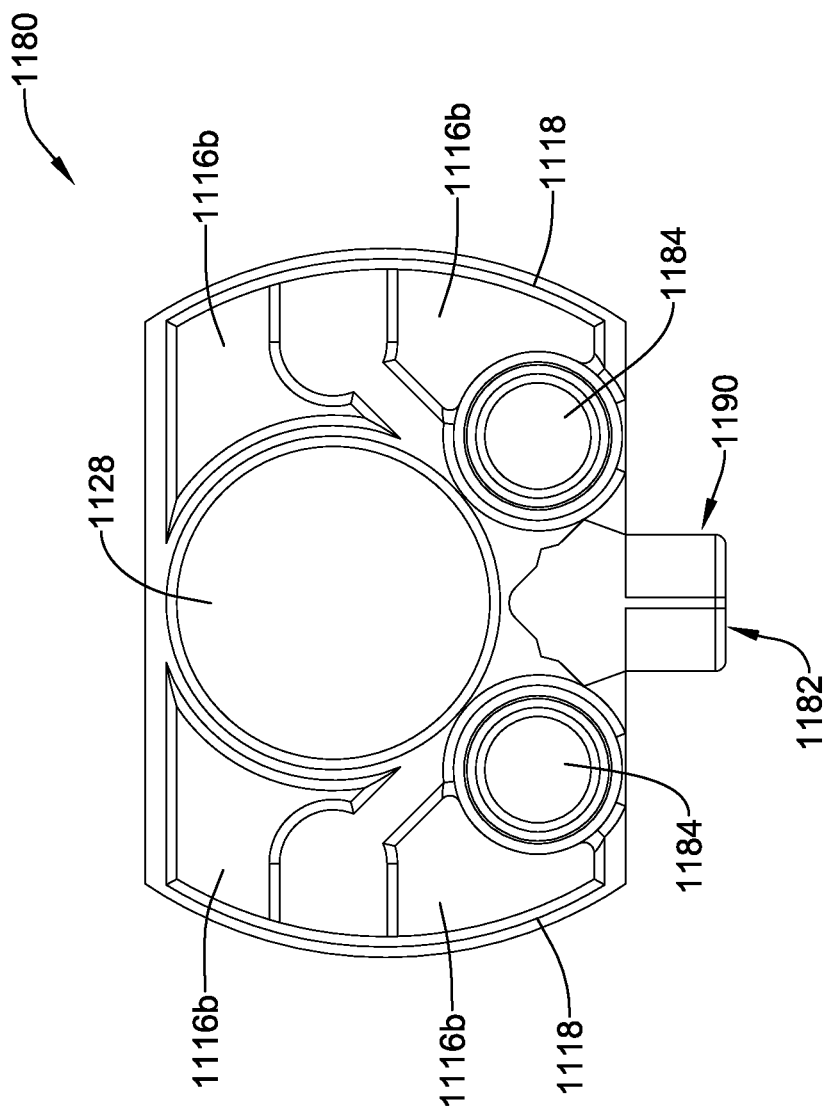
FIG. 15 is a front view of an example insert member.

In some embodiments, the upper surface 1112 may be spaced apart from the lower surface 1114, for example, by the lateral interocclusal passageway(s) 1116A disposed therebetween. In some embodiments, a posterior central orifice 1130 may be disposed along a medial line through the first member 1110, and may extend through the anterior portion 1115 of the first member 1110 to provide access to the oral cavity 50 and/or the oropharynx 30. In some embodiments, the upper surface 1112 and the lower surface 1114 may be angled toward each other in a posterior direction. In other words, the upper surface 1112 and the lower surface 1114 may be closer together at a posterior portion 1117 of the first member 1110 than at the anterior portion 1115 of the first member 1110, as illustrated in FIGS. 13-14, for example.

Figure 37:
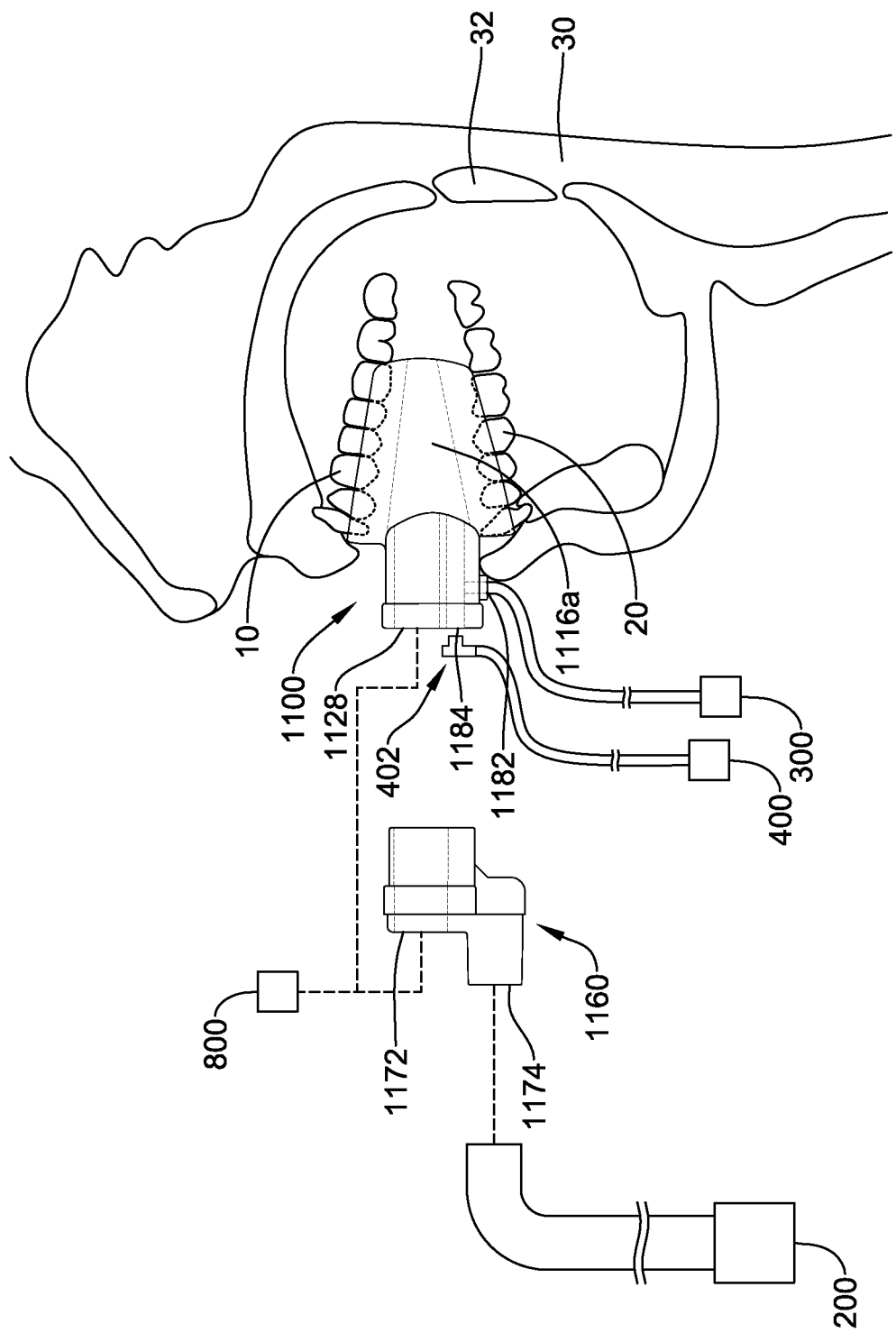
FIG. 37 is a partial side view of an example mouthpiece assembly disposed within mouth anatomy.

In some embodiments, the first member 1110 forms at least one lateral interocclusal passageway 1116A extending from the anterior portion 1115 to a posterior aperture 1120 at the posterior portion 1117. In some embodiments, at the anterior portion 1115, the at least one lateral interocclusal passageway 1116A may open into the first cavity of the tubular portion 1111. In some embodiments, the upper surface 1112 and the lower surface 1114 may be spaced apart by the at least one lateral interocclusal passageway 1116A. In some embodiments, the at least one lateral interocclusal passageway 1116A may include a left lateral interocclusal passageway 1116A and a right lateral interocclusal passageway 1116A. In other words, in some embodiments, the first member 1110 may form two (i.e., left and right) lateral interocclusal passageways 1116A configured to be positioned within the lateral interocclusal space(s) 40 and/or disposed on opposing sides of the oral cavity 50 extending in an anterior-posterior direction or orientation (as seen in FIG. 37, for example). In some embodiments, the left and right lateral interocclusal passageways 1116A may be substantially mirrored about a vertical plane through a central axis extending anteriorly to posteriorly through the first member 1110 (i.e., a superior-inferior plane through the medial line). In some embodiments, the at least one lateral interocclusal passageway 1116A may be configured to provide a conduit for respiratory gas exchange (i.e., breathing). In at least some such embodiments, the cross-sectional area (i.e., size and/or shape) of the at least one lateral interocclusal passageway 1116A may be generally sufficient to allow adequate ventilation to the patient. For example, the at least one lateral interocclusal passageway 1116A, either each individually and/or collectively, may be dimensioned to have a minimum cross-sectional open pathway area in the range of about 15 mm$^2$ to about 170 mm$^2$, for example in the range of about 50 mm$^2$ to about 150 mm$^2$, or for example in the range of about 80 mm$^2$ to about 140 mm$^2$. These ranges are believed to provide an adequate fluid pathway or conduit for respiratory gas exchange exclusively through the at least one lateral interocclusal passageway(s) 1116A within the first member 1110 for most patients, but other sizes and/or ranges are contemplated for specific applications, for example, individual patient needs.

In some embodiments, the first member 1110 may include a sampling port 1150 defining a sampling orifice 1152 formed and/or disposed within a posterior portion of the at least one lateral interocclusal passageway 1116A. In at least some embodiments having more than one lateral interocclusal passageway 1116A, each lateral interocclusal passageway 1116A may include a sampling port 1150 and a sampling orifice 1152 (i.e., a left lateral interocclusal sampling port and a right lateral interocclusal sampling port) formed therein. In some embodiments, the sampling orifice 1152 may face in a posterior direction toward the posterior aperture 1120. In some embodiments, the sampling orifice 1152 may face in other directions, such as, but not limited to, angled, laterally, medially, superiorly, inferiorly, anteriorly, combinations thereof, or other desired angles or orientations. In some embodiments, the sampling port 1150 and/or the sampling orifice 1152 may be recessed (i.e., disposed anteriorly) from the posterior aperture 1120 within the at least one lateral interocclusal passageway 1116A. In some embodiments, the sampling port 1150 and/or the sampling orifice 1152 may be generally flush with, or otherwise positioned at or within, the posterior aperture 1120. In some embodiments, the sampling port 1150 and/or the sampling orifice 1152 may include a covering disposed thereon and/or a valve disposed therein. In some embodiments, the covering and/or valve may be gas permeable to permit respiratory gases to pass therethrough, while being liquid impermeable to prevent liquids such as saliva, oral secretions, or other liquids from entering the sampling port 1150 and/or the sampling orifice 1152. In some embodiments, the first member 1110 may be configured to position the posterior aperture 1120 and/or the sampling port 1150 between an anterior edge of the second molar and the anterior tonsillar pillar 32, as may be seen in FIG. 37 for example.

In some embodiments, the sampling port 1150 and/or the sampling orifice 1152 may be in fluid communication with and/or fluidly connected to an analyzing apparatus 300. In at least some embodiments, the first member 1110 may include a sampling conduit 1154A extending anteriorly from the sampling port 1150 and/or the sampling orifice 1152 within the at least one lateral interocclusal passageway 1116A to the anterior portion 1115 and opening into the first cavity of the tubular portion 1111, as seen in FIG. 14, for example. In some embodiments, the sampling conduit 1154A may include a discrete tubular member embedded or molded within the first member 1110, a passageway or lumen integrally formed or molded within the first member 1110, and/or a combination thereof.

In some embodiments, the second member 1180 (shown illustratively in FIGS. 15-18) may be slidably received within the first cavity of the tubular portion 1111 of the first member 1110. In some embodiments, one or more posterior surfaces of the second member 1180 may be configured to engage and/or abut one or more anterior surfaces of the first member 1110 within the first cavity of the tubular portion 1111. In some embodiments, the second member 1180 may include a perimeter ring 1181 defining an outwardly-facing surface configured to be in facing engagement with an inner surface of the tubular portion 1111. In some embodiments, the second member 1180 may be attached, connected, and/or coupled to the first member 1110 using any appropriate means including, but not limited to, adhesive bonding, mechanical fastener(s), welding, snap fit, interference fit, friction fit, or other suitable means. In some embodiments, the second member 1180 may be detachable from the first member 1110. In some embodiments, the second member 1180 and the first member 1110 may form an air and/or fluid tight fit between them. In some embodiments, a gasket or other sealing element may be disposed between the second member 1180 and the first member 1110. It is contemplated that in some embodiments, the first member 1110 and the second member 1180 may be integrally formed as a single piece.

Figure 16:
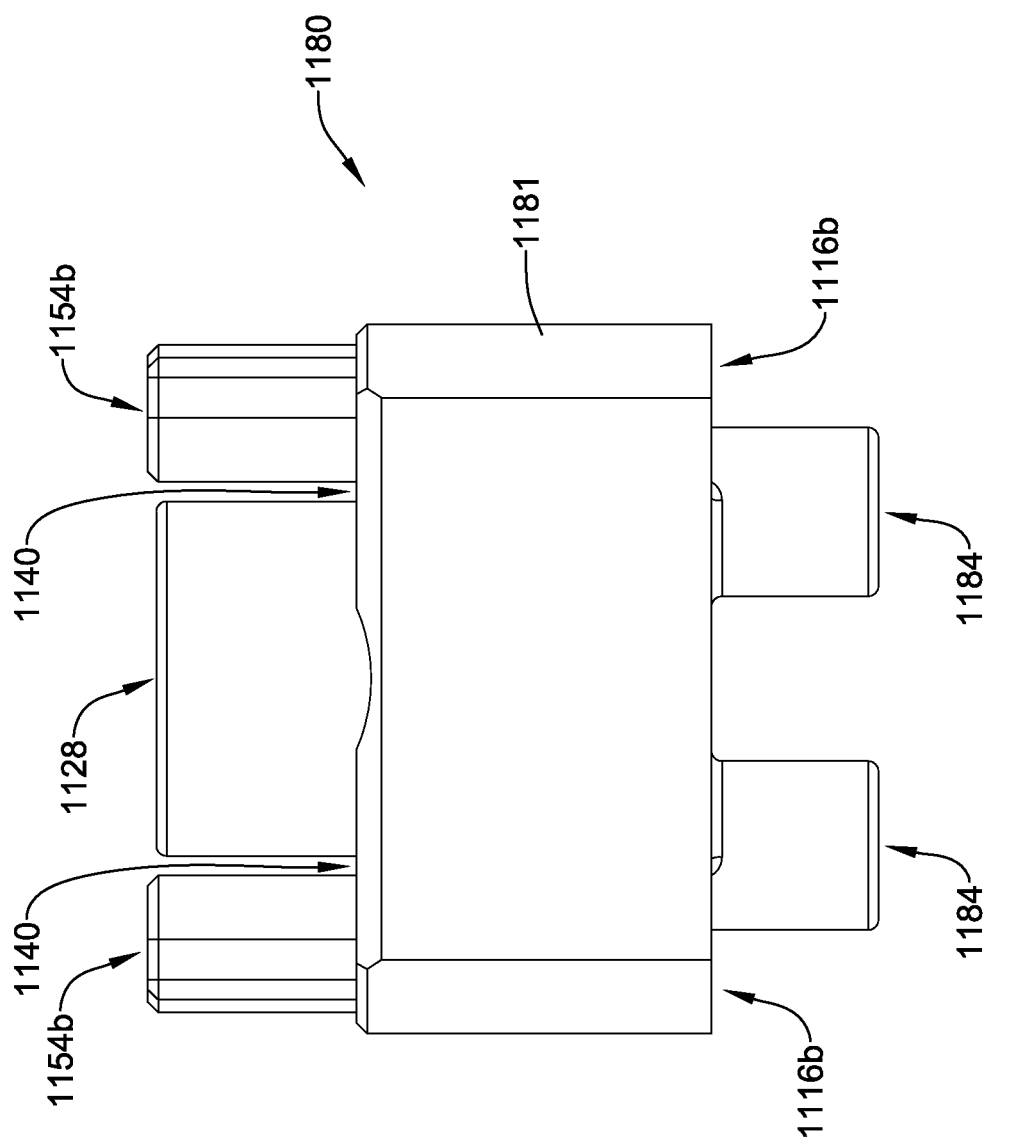
FIG. 16 is a top view of the example insert member of FIG. 15.
Figure 17:
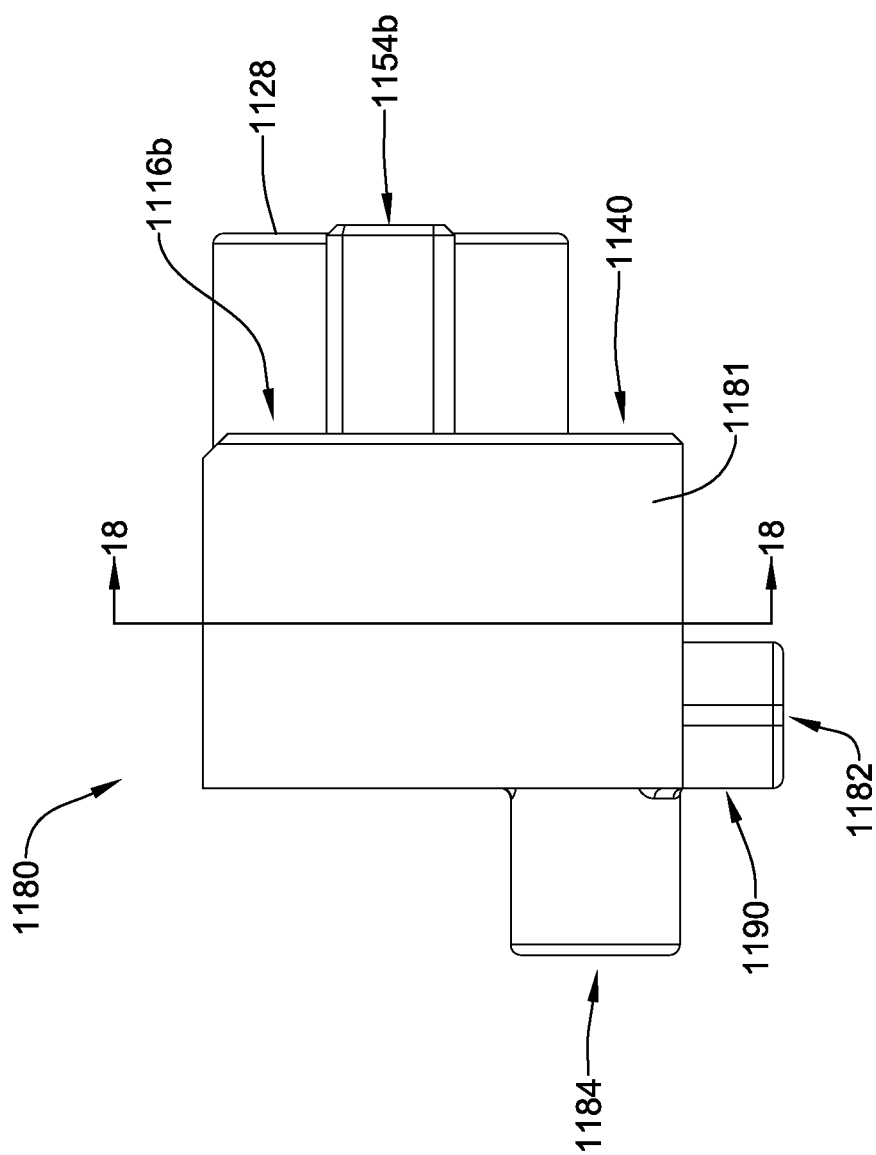
FIG. 17 is a side view of the example insert member of FIG. 15.
Figure 18:
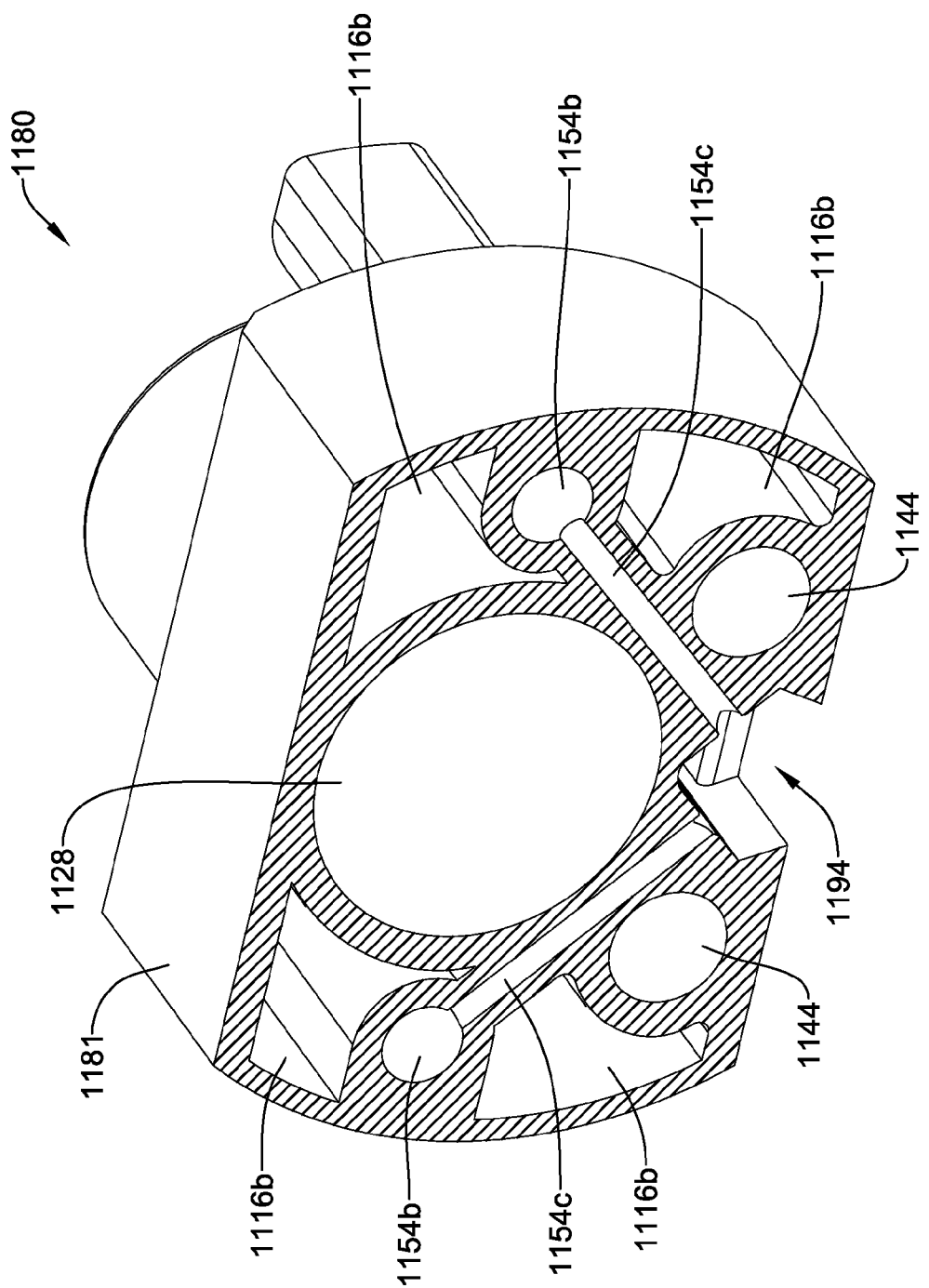
FIG. 18 is a partial cross-sectional perspective view of the example insert member of FIG. 15.

In some embodiments, the second member 1180 may include an anterior central orifice 1128 disposed along a medial line through the second member 1180. In some embodiments, the anterior central orifice 1128 may extend through the perimeter ring 1181 of the second member 1180 anteriorly to posteriorly, and in some embodiments, a wall of the anterior central orifice 1128 may further extend posteriorly from the perimeter ring 1181, as seen in FIGS. 16-18. In some embodiments, the wall of the anterior central orifice 1128 extending posteriorly from the perimeter ring 1181 may engage with and/or cooperate with the posterior central orifice 1130 of the first member 1110, thereby forming a central passageway through the mouthpiece 1100 to provide access to the oral cavity 50 and/or the oropharynx 30. In some embodiments, the wall of the anterior central orifice 1128 may be slidably received within the posterior central orifice 1130. In some embodiments, the wall of the anterior central orifice 1128 may abut an anterior edge of the posterior central orifice 1130. In some embodiments, at least a portion of the central passageway may be disposed within the first cavity of the tubular portion 1111. However, the central passageway is isolated from the first cavity of the tubular portion 1111. In other words, within the mouthpiece, the central passageway is not in fluid communication with any part of the first cavity, the lateral interocclusal passageway(s), the sampling conduit(s), and/or the supplemental gas conduit(s).

In at least some embodiments, with the mouthpiece 1100 positioned within the mouth of a patient, the anterior central orifice 1128 may extend or be positioned exterior to the mouth of the patient. As such, a medical instrument 800, such as a suction device, an endoscope, an endotracheal tube, etc., for example, may be introduced into the oral cavity 50 through the central passageway as needed or desired.

In at least some embodiments, the second member 1180 may be formed from and/or may include a relatively rigid and/or hard material, such as those listed herein, selected to resist compression, collapse, and/or crushing under pressure. This may permit the second member 1180 and/or the mouthpiece 1100 to resist the compression exerted by a human jaw/bite, which may be useful when a medical instrument 800 is disposed within the posterior central orifice 1130, the anterior central orifice 1128, and/or the central passageway.

In some embodiments, the second member 1180 may include one or more anterior apertures 1118. In some embodiments, at least a portion of each of the one or more anterior apertures may be formed by the perimeter ring 1181. In some embodiments, the second member 1180 may include one or more lateral interocclusal passageways 1116B disposed inside of and passing through the perimeter ring 1181 anteriorly to posteriorly from the one or more anterior apertures 1118. When the second member 1180 is positioned within the first cavity of the tubular portion 1111 such that the one or more posterior surfaces of the second member 1180 are in engagement with and/or abutting the one or more anterior surfaces of the first member 1110, the one or more lateral interocclusal passageways 1116B of the second member 1180 may be in fluid communication with the at least one lateral interocclusal passageway 1116A of the first member 1110, with a continuous path formed from the anterior apertures 1118 to the posterior aperture(s) 1120.

In some embodiments, the second member 1180 may include a manifold 1190 disposed within a manifold recess 1194 formed in an anterior region of an inferior surface of the perimeter ring 1181. In some embodiments, the manifold 1190 may be slidably received within the manifold recess 1194. In some embodiments, a protrusion on the manifold 1190 may cooperate with a dimple in the manifold recess 1194 to retain the manifold 1190 in place. In some embodiments, the manifold 1190 may be held in place using a friction or interference fit with the second member 1180. Other arrangements are also contemplated. In some embodiments, the manifold 1190 may include a first port 1182. When the manifold 1190 is disposed within the manifold recess 1194, the first port 1182 may be in fluid communication with a sampling conduit 1154C extending from the manifold recess 1194 transversely at an angle relative to the anterior central orifice 1128 to (and in further fluid communication with) a sampling conduit 1154B extending anteriorly to posteriorly generally parallel to the anterior central orifice 1128. In at least some embodiments, the second member 1180 may include at least one sampling conduit 1154B, 1154C for each sampling conduit 1154A included in the first member 1110. In some embodiments, a wall of the sampling conduit 1154B of the second member 1180 extending posteriorly of the perimeter ring 1181 may engage with and/or cooperate with the sampling conduit 1154A of the first member 1110, thereby forming a fluidtight sampling conduit or passageway extending from the sampling port 1150 and/or the sampling orifice 1152 to the first port 1182 at the manifold 1190. In some embodiments, the wall of the sampling conduit 1154B of the second member 1180 may be slidably received within the sampling conduit 1154A of the first member 1110. In some embodiments, the wall of the sampling conduit 1154B of the second member 1180 may abut an anterior edge or surface of the sampling conduit 1154A of the first member 1110.

In at least some embodiments, an analyzing apparatus 300 may be fluidly connected to the first port 1182, for example, by a section of tubular hose or other suitable means. The analyzing apparatus 300 may be any suitable apparatus known in the art for analyzing and/or monitoring respiratory gases for, but not limited to, partial pressure of carbon dioxide ($CO_2$), oxygen ($O_2$), nitrous oxide ($N_2O$), and/or potent anesthetic gases (e.g., sevoflurane, desflurane, isoflurane, etc.), for example. In some embodiments, the analyzing apparatus 300 may compare, plot, chart, or otherwise record data such as, for example, carbon dioxide ($CO_2$) partial pressure as a function of time and/or volume.

In at least some embodiments, the first member 1110 may include a manifold aperture 1192 extending from the first cavity within the tubular portion 1111 through a wall of the tubular portion 1111. In some embodiments, the manifold aperture 1192 may extend through an inferior wall of the tubular portion 1111. In some embodiments, the manifold 1190 may be disposed in and/or may extend through the manifold aperture 1192 when the second member 1180 is disposed within the first cavity of the tubular portion 1111.

In some embodiments, the second member 1180 may include one or more second ports 1184 extending anteriorly of the perimeter ring 1181. Each second port 1184 may be fluidly connected to a supplemental gas conduit 1144 extending anteriorly to posteriorly through the second member 1180 inside of the perimeter ring 1181. Each supplemental gas conduit 1144 terminates posteriorly at a supply orifice 1140. In some embodiments, the supply orifice 1140 may be configured to be in fluid communication with the at least one lateral interocclusal passageway 1116A of the first member 1110 when the second member 1180 is disposed within the first cavity of the tubular portion 1111. In embodiments having more than one lateral interocclusal passageway 1116A, there may be a distinct supply orifice 1140 in fluid communication with each lateral interocclusal passageway 1116A (i.e., a left lateral interocclusal supply orifice and a right lateral interocclusal supply orifice). In some embodiments, the one or more second ports 1184, the supplemental gas conduit 1144, and the supply orifice 1140 may be in fluid communication with a source of supplemental gas 400, for example, oxygen, nitrous oxide, an aerosolized pharmaceutical, or other suitable gas. In some embodiments, the one or more second ports 1184 may be configured to receive, accept, connect to, or otherwise coupled with a means for supplying a supplemental gas from the source of supplemental gas 400 to the mouthpiece 1100, such as a nasal cannula 402 or a section of tubular hose, for example. In some embodiments, the second member 1180 may include two second ports 1184, wherein the two second ports 1184 are each configured to receive one of two prongs of a nasal cannula 402. In other words, the source of supplemental gas 400 may be operatively connected to the one or more second ports 1184 and/or to the supply orifice 1140, as shown in FIG. 37. In some embodiments, the supply orifice 1140 may be configured to deliver a supplemental gas into the at least one lateral interocclusal passageway 1116A. As the supplemental gas is delivered to the supply orifice 1140, the supplemental gas mixes with the air or gas being delivered through the at least one lateral interocclusal passageway 1116A to a space adjacent the patient's oropharynx 30. In some embodiments, the supplemental gas may be delivered at a flow rate of about 0.1 liter per minute to about 15 liters per minute.

In at least some embodiments, the mouthpiece 1100 may include both a supply orifice 1140 and a sampling port 1150, along with any additional structure associated with each (i.e., supplemental gas conduit 1144, sampling conduit 1154, first port 1182, second port(s) 1184, etc.). In these embodiments, the supply orifice 1140 may be disposed or located anteriorly of the sampling port 1150 within the lateral interocclusal passageway. Using this arrangement or configuration, supplemental gas can be delivered to the at least one lateral interocclusal passageway 1116A for inspiration by the patient without diluting exhaled respiratory gases being collected at the sampling port 1150. As the patient exhales, exhaled respiratory gases are expelled through the at least one lateral interocclusal passageway 1116A in a posterior to anterior direction, and any supplemental gas flowing through the supply orifice 1140 is expelled away from the sampling port 1150 with the exhaled respiratory gases. As such, exhaled respiratory gases may be collected at the sampling port 1150 which are not diluted by the supplemental gas.

Figure 19:
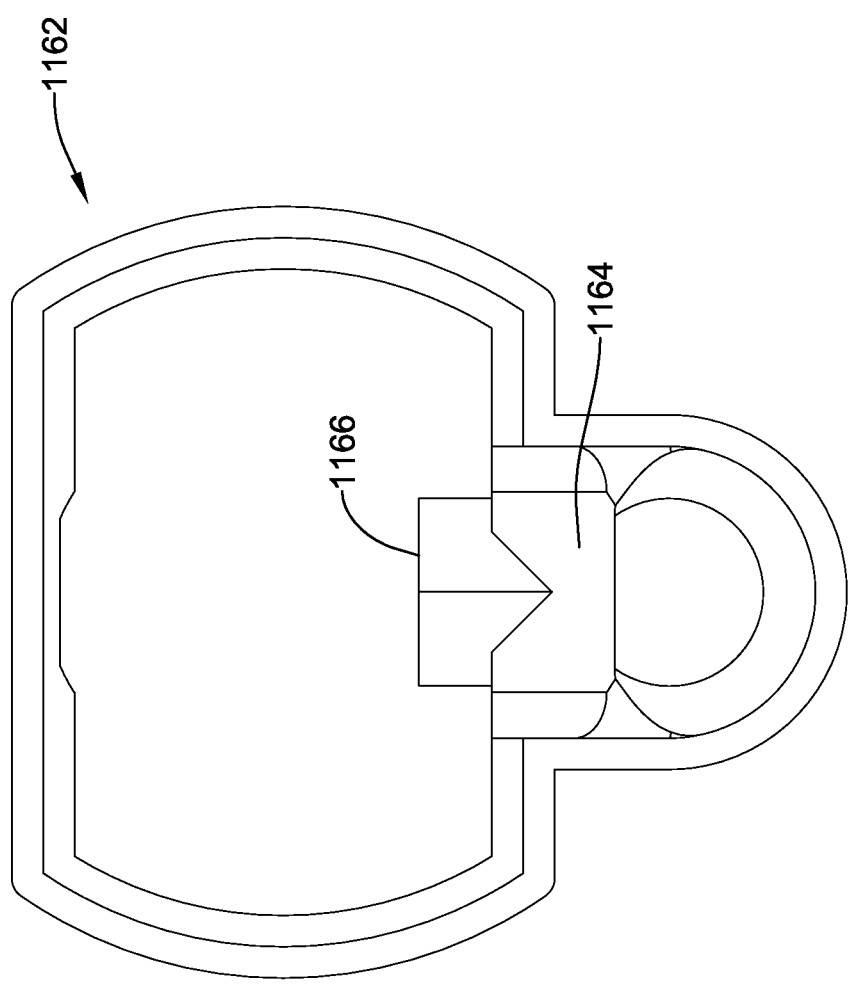
FIG. 19 is a front view of an example sleeve member.
Figure 20:
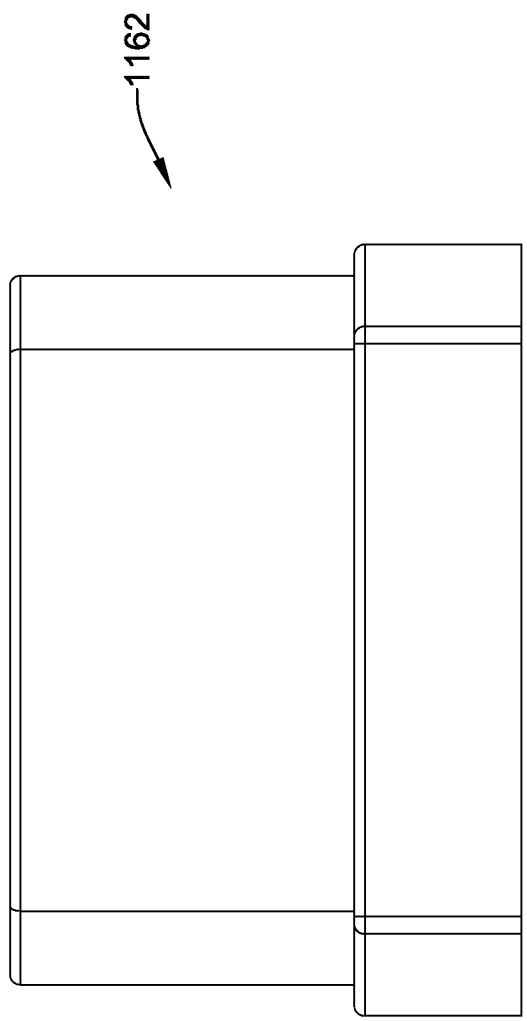
FIG. 20 is a top view of the example sleeve member of FIG. 19.
Figure 21:
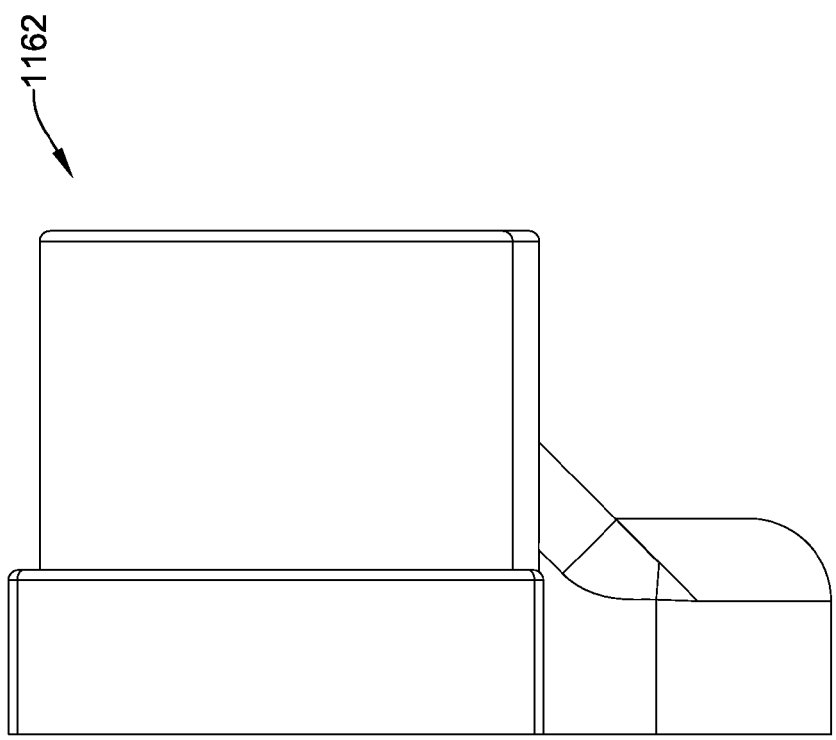
FIG. 21 is a side view of the example sleeve member of FIG. 19.
Figure 22:
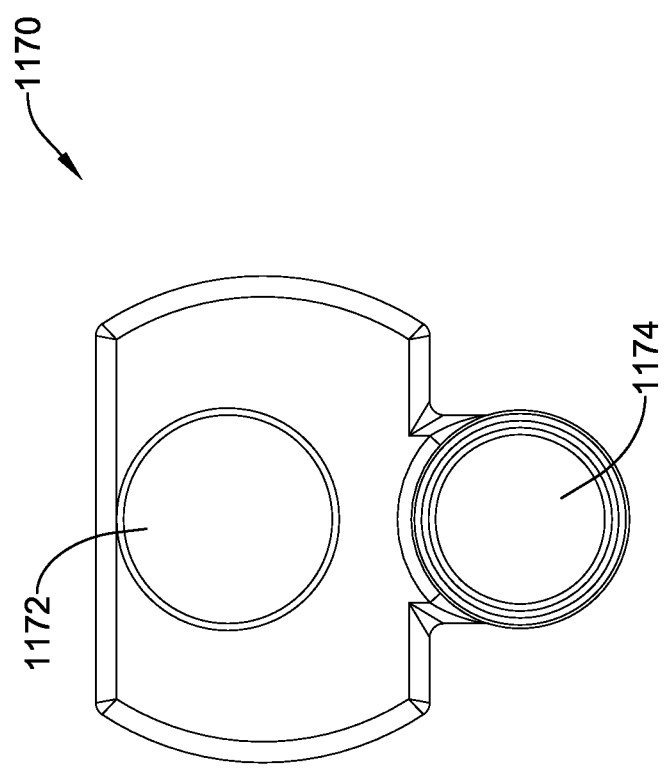
FIG. 22 is a front view of the example adapter member.
Figure 23:
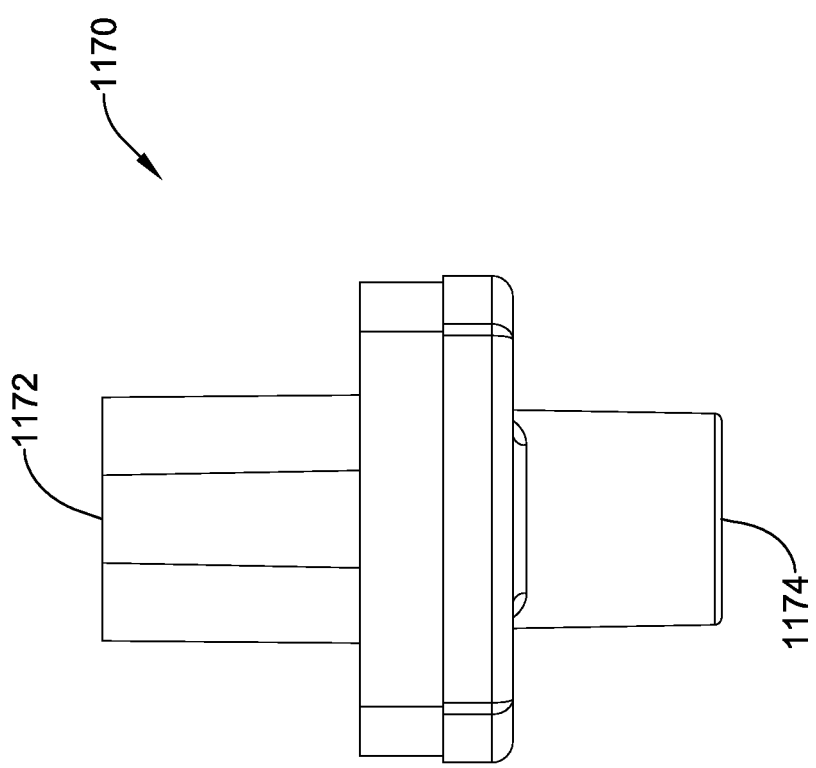
FIG. 23 is a top view of the example adapter member of FIG. 22.
Figure 24:
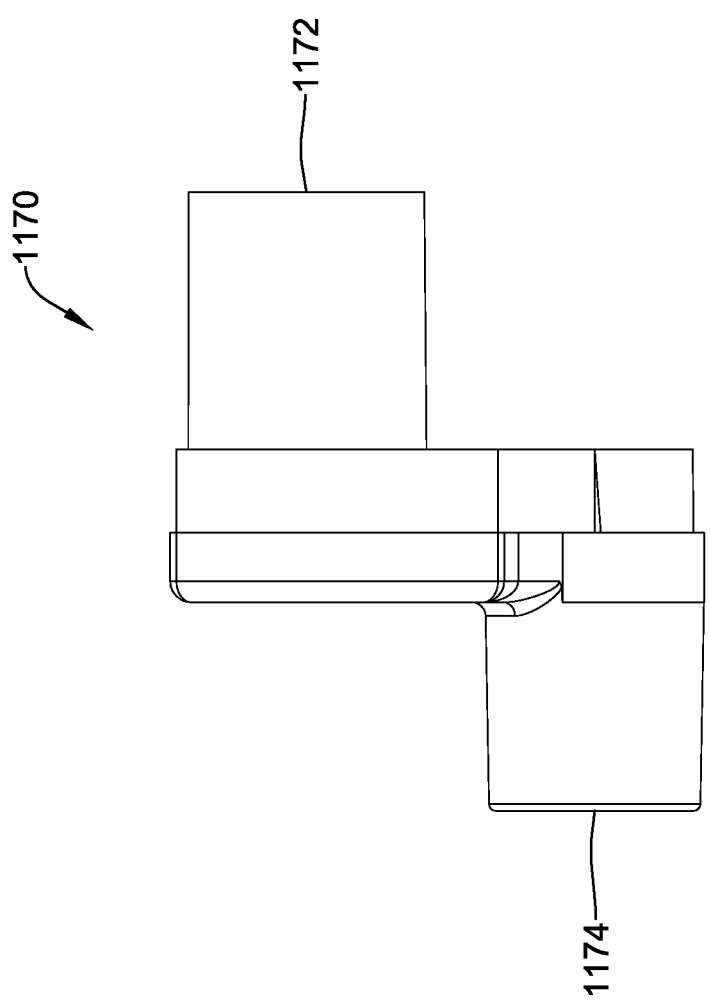
FIG. 24 is a side view of the example adapter member of FIG. 22.

In some embodiments, a medical breathing apparatus may include a mouthpiece 1100, as described hereinabove, and an adapter 1160 configured to couple with the mouthpiece 1100, as shown in FIGS. 25-27, for example. In some embodiments, an adapter 1160 may include a sleeve 1162 (shown illustratively in FIGS. 19-21) and a connector 1170 (shown illustratively in FIGS. 22-24).

In some embodiments, a posterior portion of the sleeve 1162 may be sized and configured to be slidably received within the first cavity of the tubular portion 1111 of the first member 1110. In some embodiments, when the sleeve 1162 is received within the first cavity of the tubular portion 1111, a posterior surface of the sleeve 1162 may engage and/or abut an anterior surface of the perimeter ring 1181. In some embodiments, when the sleeve 1162 is received within the first cavity of the tubular portion 1111, a posterior surface of the sleeve 1162 may be spaced apart from an anterior surface of the perimeter ring 1181. In some embodiments, the sleeve 1162 may define an outwardly-facing surface configured to be in facing engagement with the inner surface of the tubular portion 1111, when the sleeve 1162 is received within the first cavity of the tubular portion 1111. In some embodiments, the sleeve 1162 may be attached, connected, and/or coupled to the first member 1110 using any appropriate means including, but not limited to, adhesive bonding, mechanical fastener(s), welding, snap fit, interference fit, friction fit, or other suitable means. In some embodiments, the sleeve 1162 may be detachable from the first member 1110. In some embodiments, the sleeve 1162 and the first member 1110 may form an air and/or fluid tight fit between them. In some embodiments, a gasket or other sealing element may be disposed between the sleeve 1162 and the first member 1110.

In some embodiments, an anterior portion of the sleeve 1162 may include a collar offset radially outwardly from the outer surface of the sleeve 1162. In some embodiments, the sleeve 1162 may include a protrusion extending inferiorly from the anterior portion of the sleeve 1162. At a posterior region of the protrusion, the sleeve 1162 may include a ramp 1164 angled superiorly toward the posterior portion of the sleeve 1162. At the top of the ramp 1164, the sleeve 1162 may include an internally-extending divider 1166, for reasons that will become apparent.

In some embodiments, a superior-inferior oriented front wall of the connector 1170 may include a central orifice 1172 and a respiratory orifice 1174 offset inferiorly from the central orifice 1172. In some embodiments, the central orifice 1172 may extend anteriorly to posteriorly through the front wall of the connector 1170. In some embodiments, the respiratory orifice 1174 may extend anteriorly to posteriorly through the front wall of the connector 1170. In at least some embodiments, a wall of the central orifice 1172 may extend posteriorly from the front wall of the connector 1170. In some embodiments, the wall of the central orifice 1172 may be configured to engage with and/or abut the second member 1180. For example, the central orifice 1172 may form an extension of the central passageway formed by the anterior central orifice 1128 and the posterior central orifice 1130, thereby permitting a medical instrument 800, such as a suction device, an endoscope, an endotracheal tube, etc., for example, to be introduced into the oral cavity 50 through the central passageway as needed or desired with the adapter 1160 engaged with the mouthpiece 1100.

In some embodiments, a wall of the respiratory orifice 1174 may extend posteriorly to anteriorly from the front wall of the connector 1170. In other words, the wall of the central orifice 1172 and the wall of the respiratory orifice 1174 may extend in substantially opposite directions from the front wall of the connector 1170. In at least some embodiments, the respiratory orifice 1174 may be fluidly and/or operatively connected to a ventilator or pressure device 200, for example as seen in FIG. 37, configured to deliver continuous or intermittent positive pressure to the respiratory orifice 1174 and/or to the mouthpiece 1100, thereby delivering a respiratory gas (e.g., air) to a space adjacent the oropharynx 30 for inspiration by the patient.

In some embodiments, the respiratory orifice 1174 may be configured to connect to known or existing airway connectors and/or devices, such as ventilator equipment, CPAP machines, nebulizers, an anesthesia circuit, and the like. Some benefits of connecting an anesthesia circuit to the mouthpiece 1100 via the adapter 1160 may include, but are not limited to: 1) the anesthesia circuit may be used to add pressure to the system to attempt to break or prevent airway obstruction; 2) anesthetic gases may be delivered to the patient in addition to supplemental gas (e.g., oxygen); 3) mixed air and oxygen may be delivered to the patient to reduce the risk of fire in the presence of cautery or other sources of electrical discharge (i.e., spark) that may occur during some procedures; and/or 4) an anesthesia circuit connected to the mouthpiece 1100 via the adapter 1160 is a relatively closed system of delivering oxygen that may reduce the risk of oxygen delivery under drapes or near the face that could result in fire. The adapter 1160 may be useful when sedation and/or a procedure is occurring in an operating room or somewhere with the appropriate and/or necessary airway equipment. In some facilities, the appropriate airway equipment may not be available in endoscopy suites, emergency rooms, small procedure rooms, etc. where only a wall oxygen source for connecting tubing such as a nasal cannula is provided.

In some embodiments, the collar of the sleeve 1162 may be sized and configured to receive a flange portion extending posteriorly from the front wall of the connector 1170 therein. In some embodiments, connector 1170 may be fixedly attached to the sleeve 1162 using various suitable means including, but not limited to, adhesive bonding, welding, mechanical fastener(s), interference fit, friction fit, snap fit, and the like.

With the connector 1170 engaged with the sleeve 1162, the respiratory orifice 1174 may be generally aligned with the protrusion extending inferiorly from the anterior portion of the sleeve 1162. Accordingly, respiratory gas (i.e., supplemental gas, air, etc. as described above) passing posteriorly through the respiratory orifice 1174 (for example, under pressure) may be directed superiorly up the ramp 1164 toward the divider 1166. In at least some embodiments, when the adapter 1160 is engaged with and/or connected to the mouthpiece 1100, one second port 1184 may be disposed laterally on either side of the divider 1166. Accordingly, respiratory gas flowing through the respiratory orifice 1174 and up the ramp 1164 may be directed toward the second ports 1184 and/or the anterior apertures 1118 by the divider 1166. Continuous or intermittent positive pressure may convey the gaseous fluid(s) into the lateral interocclusal passageways to thereby deliver the respiratory gas (e.g., air, oxygen, etc.) through the posterior apertures 1120 to a space adjacent the oropharynx 30 for inspiration by the patient.

In some embodiments, the medical breathing apparatus may include a plug 500 configured to be removably inserted into the central orifice 1172 of the connector 1170, or the anterior central orifice 1128 of the second member 1180, if the adapter 1160 is not present or in use. An example plug 500 may be seen illustratively in FIGS. 26-27. The plug 500 may be configured to close the central orifice 1172 or the anterior central orifice 1128 whenever a medical instrument 800 is absent from the central passageway, thereby preventing foreign objects or debris from entering the oral cavity 50 and directing patient respiration through the lateral interocclusal channels of the mouthpiece 1100.

In some embodiments, the mouthpiece 1100 and/or the posterior aperture(s) 1120 may be configured to avoid delivering a respiratory gas directly onto the tongue 52 of the patient. In some embodiments, the mouthpiece 1100 and/or the posterior aperture(s) 1120 may be configured to avoid delivering a respiratory gas directly onto a check or directly into the buccal cavity of the patient. In some embodiments, the mouthpiece 1100 and/or the posterior aperture(s) 1120 may be configured to deliver a respiratory gas through and/or using the lateral interocclusal space 40 of the patient. In some embodiments, the mouthpiece 1100 and/or the posterior aperture(s) 1120 may be configured to deliver a respiratory gas to the posterior oropharynx 30 of the patient while reducing the chance of eliciting a gag reflex and/or without eliciting a gag reflex. In some embodiments, the mouthpiece 1100 and/or the posterior aperture(s) 1120 may be configured to deliver a respiratory gas to the posterior oropharynx 30 of the patient while reducing the chance of stimulating salivation and/or without stimulating salivation.

In at least some embodiments, the mouthpiece 1100 may be used in spontaneously breathing (and in some cases, sedated) patients, where positive pressure respiration/ventilation is not needed, without the adapter 1160. A plug 500 may be inserted into the anterior central orifice 1128 when access to the oral cavity 50 is not needed and to force respiration to occur through the lateral interocclusal passageways.

Figure 29:
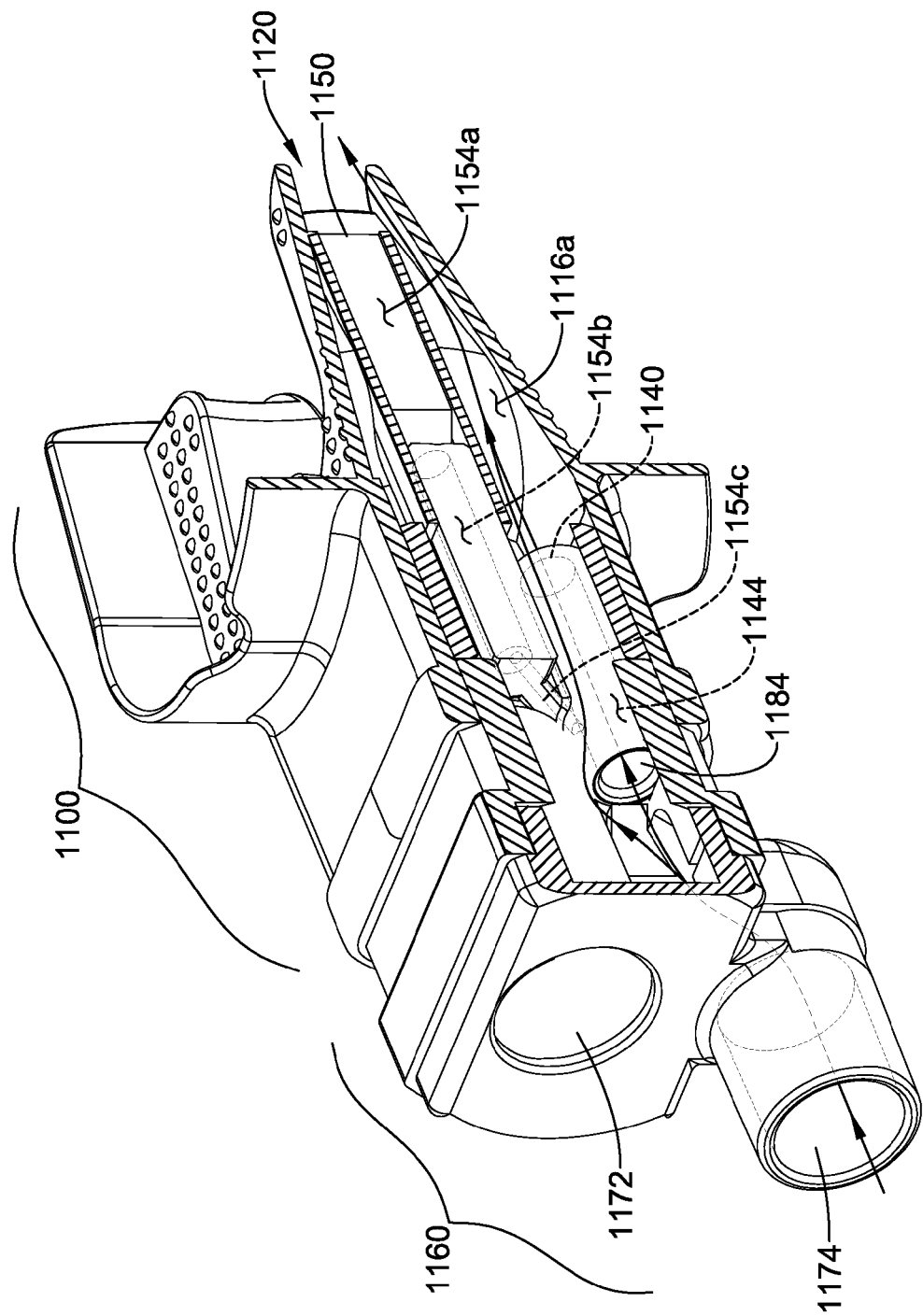
FIG. 29 is a partial cross-sectional perspective view of an example mouthpiece assembly.

FIG. 29, shown in partial cross-section, illustrates a flow path of a respiratory gas through a medical breathing apparatus including a mouthpiece 1100 and an adapter 1160. As shown in the Figure, during inspiration, respiratory gas may enter through the respiratory orifice 1174, be directed up the ramp 1164, and split to the left and right by the divider 1166. Respiratory gas then enters the second ports 1184 and passes through the supplemental gas conduit 1144 before exiting the supply orifice 1140 into the at least one lateral interocclusal passageway 1116A. At the same time, respiratory gas enters the anterior apertures 1118 and passes through the lateral interocclusal passageways 1116B (going around or bypassing the supplemental gas conduit 1144) before entering into the at least one lateral interocclusal passageway 1116A. Respiratory gas in transported posteriorly through the at least one lateral interocclusal passageway 1116A and delivered through the posterior aperture(s) 1120.

During exhalation, exhaled respiratory gas enters the mouthpiece 1100 through the posterior aperture(s) 1120 into the at least one lateral interocclusal passageway 1116A. Once in the at least one lateral interocclusal passageway 1116A, two things happen. Fresh respiratory gas and/or supplemental gas coming from the respiratory orifice 1174 is pushed anteriorly back up the at least one lateral interocclusal passageway 1116A past the sampling port(s) 1150. As such, the sampling port(s) 1150 is subjected only to exhaled respiratory gas, which enters the sampling port(s) 1150 through the sampling orifice 1152. Exhaled respiratory gas travels anteriorly through the sampling conduits 1154A, 1154B, 1154C to the manifold 1190, where the exhaled respiratory gas passes through the first port 1182 en route to an analyzing apparatus 300.

Figure 31:
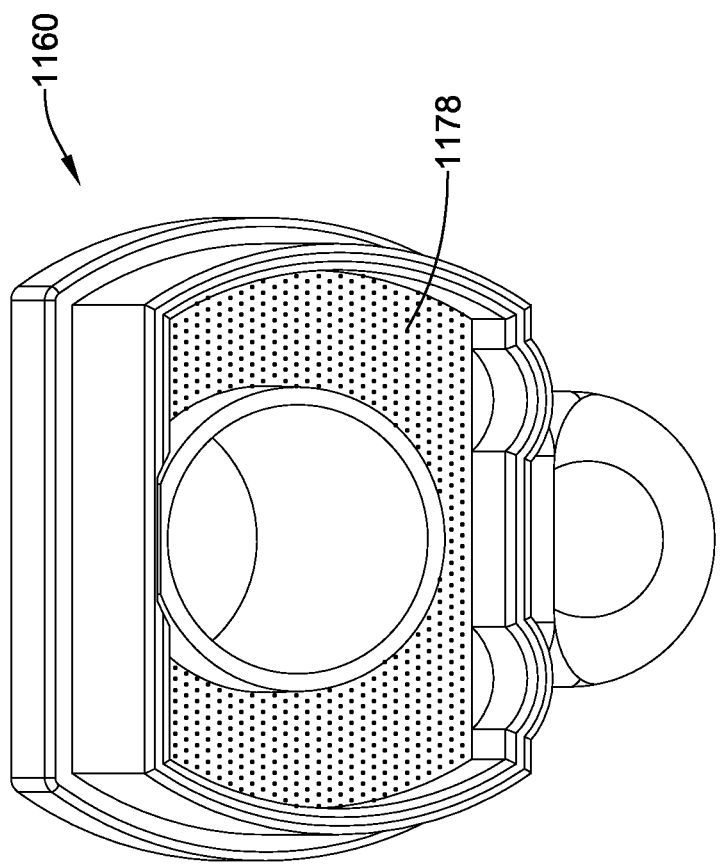
FIG. 31 is a back view of an example adapter assembly.

In some embodiments, the adapter 1160 may include a heat and moisture exchange (HME) filter 1178 placed in the path of respiratory gas exchange, as seen in FIG. 31. In some embodiments, the heat and moisture exchange filter 1178 may be disposed within the sleeve 1162, posteriorly of the front wall of the connector 1170. In some embodiments, the heat and moisture exchange filter 1178 may substantially surround the wall of the central orifice 1172 extending posteriorly from the front wall of the connector 1170. In some embodiments, the heat and moisture exchange filter 1178 may substantially cover the ramp 1164, the divider 1166, and/or the protrusion extending inferiorly from the anterior portion of the sleeve 1162, such that respiratory gas must pass through the heat and moisture exchange filter 1178 during respiration/ventilation. In some embodiments, the heat and moisture exchange filter 1178 may be a sponge-like material configured to trap moisture from exhaled/expired respiratory gases. During exhalation, moisture and heat from exhaled respiratory gas may condense on the heat and moisture exchange filter 1178, and when fresh, dry respiratory gas in inhaled, the moisture and heat may be picked up and/or absorbed by the fresh respiratory gas prior to entering the patient. In other words, the heat and moisture exchange filter 1178 may function as an artificial nose. In some embodiments, the heat and moisture exchange filter 1178 may include an impregnated hygroscopic material to enhance moisture retention.

A method for delivering a gas to a patient may include inserting a mouthpiece into a mouth of a patient, the mouthpiece having a generally U-shaped first member forming at least one lateral interocclusal passageway extending posteriorly between an upper dentition and a lower dentition of the patient. After inserting the mouthpiece, the method may include delivering a respiratory gas to the patient through the at least one lateral interocclusal passageway such that the respiratory gas is delivered through a posterior aperture to a space adjacent the patient's posterior oropharynx. In some embodiments, the mouthpiece may include a supplemental gas conduit in fluid communication with the at least one lateral interocclusal passageway, and the method may further include delivering a supplemental gas through the supplemental gas conduit and into the at least one lateral interocclusal passageway, the supplemental gas mixing with the respiratory gas and being delivered to the patient's posterior oropharynx. In some embodiments, the first member may include a sampling port disposed within a posterior portion of the lateral interocclusal passageway, and a sampling conduit fluidly connecting the sampling port to an analyzing apparatus, and the method may further include collecting a sample of respiratory gases at the sampling port, and analyzing the sample for partial pressure of an expired respiratory gas such as carbon dioxide (CO2), oxygen (O2), nitrous oxide (N2O), and/or potent anesthetic gases (e.g., sevoflurane, desflurane, isoflurane, etc.), for example. In some embodiments, the method may further include plotting expired respiratory gas partial pressure as a function of time and/or exhaled volume.

The structure and/or method(s) described above, and in particular the lack of structure disposed within the oral cavity, may reduce or eliminate intra-oral bulk commonly found in prior oral appliances that may displace the tongue posteriorly within the oral cavity which may contribute to or increase airway obstruction. Accordingly, the mouthpiece described herein, alone or when combined with positive airway pressure delivered through the at least one lateral interocclusal passageway to the oropharynx, may relieve or improve airway obstruction by displacing the tongue anteriorly, or permitting the tongue to move anteriorly due to lack of bulk preventing such movement, which may increase the glossopharyngeal space and/or open the oropharynx. Such improvement(s) may be beneficial for use with patients either under or recovering from anesthesia or sedation, as well as sleeping patients, such as when treating sleep apnea, for example. In some embodiments, a mandibular advancement device or feature may be incorporated into the mouthpiece.

By utilizing the lateral interocclusal space, supplemental gas can be delivered posteriorly, closer to the oropharynx without the adverse effects of intra-oral devices or structures such as eliciting a gag reflex, stimulation of salivation, and/or displacing the tongue posteriorly. For example, delivering a respiratory gas such as oxygen near the oropharynx may increase the opportunity for entraining supplemental respiratory gas (e.g., oxygen) independent of whether oral or nasal breathing is taking place. Delivery of respiratory gas and/or positive pressure near the oropharynx may increase pressure in the glossopharyngeal space, which may promote anterior displacement of the tongue and reduce airway obstruction.

Sampling of respiratory gases may be useful in several situations, such as when using capnography to monitor partial pressure of respiratory gas, such as carbon dioxide (CO2) for example. In patients that do not have an endotracheal tube in place, such as awake or sedated patients, it may be difficult to obtain an undiluted sample of expired respiratory gas due to a variety of sampling problems. For example, supplemental gases delivered at or near the sampling site may dilute the sample of expired respiratory gas. In another example, with some known devices or systems, exhaled respiratory gases are sampled at the mouth opening (anteriorly relative to the oropharynx) and/or nasally. Sampling at one location (i.e., at the mouth) while the patient is breathing through another (i.e., the nose), may be problematic and/or introduce inaccuracies. It may be difficult to sample from both without a dilutional effect. Using the mouthpiece described above, exhaled respiratory gases may be sampled near the oropharynx, which may reduce sampling inaccuracies from dead space dilution and entrainment of room air and/or supplemental gas. Sampling near the oropharynx may also increase the chance of respiratory gas sampling independent of whether mouth breathing or nasal breathing is occurring. Additionally, the arrangement of the supplemental gas supply orifice anteriorly of the sampling port allows an exhaling patient to deliver an undiluted sample to the sampling port because exhaled respiratory gas moves anteriorly through the at least one lateral interocclusal passageway and forces supplemental gas within the at least one lateral interocclusal passageway to be expelled anteriorly away from the sampling port during expiration, thereby increasing the accuracy of the sample by preventing dilution of the exhaled respiratory gas at the sampling port by the supplemental gas.

In at least some embodiments, portions or all of the mouthpiece may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the mouthpiece in determining its location. Some examples of radiopaque materials can include, but are not limited to, gold, platinum, palladium, tantalum, tungsten alloy, polymer material loaded with a radiopaque filler, and the like. Additionally, radiopaque bands or markers may also be incorporated into the design of the mouthpiece to achieve the same result.

In some embodiments, a degree of Magnetic Resonance Imaging (MRI) compatibility is imparted into the mouthpiece. For example, the mouthpiece, or portions thereof, may be made of a material that does not substantially distort the image and create substantial artifacts (i.e., gaps in the image). Certain ferromagnetic materials, for example, may not be suitable because they may create artifacts in an MRI image. The mouthpiece, or portions thereof, may also be made from a material that the MRI machine can image successfully. Some metallic materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

The mouthpiece and/or the adapter may be made from or otherwise include a biocompatible polymer or polymeric material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP. In some embodiments, the anterior portion or bite block portion of the mouthpiece may be formed of a stiffer or more rigid material than the posterior portion forming the at least one lateral interocclusal passageway. Various combinations of hard, soft, rigid, or flexible materials may be used as desired.

In some embodiments, an exterior surface of the mouthpiece may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the mouthpiece. In some embodiments, the at least one lateral interocclusal passageway may include a lubricious, hydrophilic, protective, or other similar coating disposed on an inner surface thereof. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof.

Figure 28:
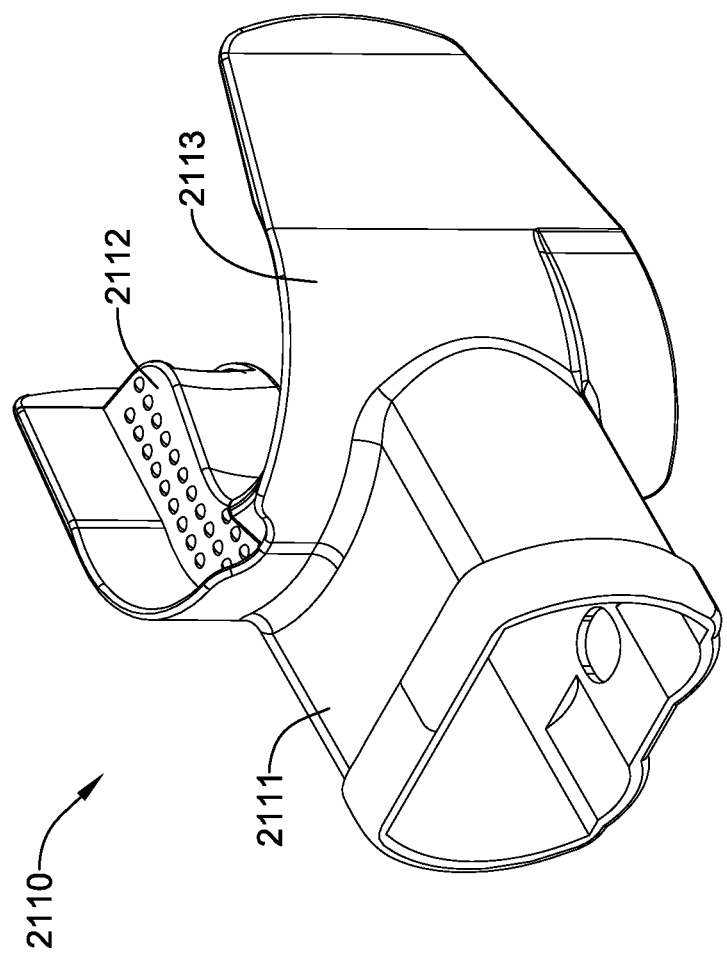
FIG. 28 is a perspective view of an example U-shaped member.

Other embodiments of a medical breathing apparatus are also contemplated which may include subsets and/or varying combinations of features described in detail above. For example, a medical mouthpiece may include a generally U-shaped first member 2110 having a tubular portion 2111 extending anteriorly therefrom and defining a cavity, and the second member 1180 described above, for example. In some embodiments, the U-shaped first member 2110 may include a curved base and a pair of spaced-apart arms extending away from the curved base. In some embodiments, the tubular portion 2111 may extend anteriorly from the curved base. In some embodiments, the pair of spaced-apart arms may extend posteriorly from the curved base. In some embodiments, the first member 2110 (shown illustratively in FIG. 28) may include an upper surface 2112 shaped and configured to receive and/or contact an upper dentition 10 of a patient. In some embodiments, the first member 2110 may include a lower surface shaped and configured to receive and/or contact a lower dentition 20 of a patient.

In some embodiments, the first member 2110 may include a flange 2113 extending superiorly from the upper surface 2112 and/or inferiorly from the lower surface at an outer perimeter or edge of the upper surface 2112 and/or the lower surface. In use, the flange 2113 may be positioned with the upper dentition 10 and lower dentition 20 on a posterior side of the flange 2113 and the lips of the patient on an anterior side of the flange 2113. Accordingly, in some embodiments, the first member 2110 and/or the flange 2113 may be made from a generally soft, flexible material such as those disclosed herein, so as to avoid injury to the lips and/or gums of the patient and/or to improve comfort. In some embodiments, the upper surface 2112 and/or the lower surface may be made from a material that is less flexible and more rigid than the flange 2113. In some embodiments, the upper surface 2112 and/or the lower surface may be made from a material that is more flexible and less rigid than the flange 2113. In some embodiments, the upper surface 2112 and/or the lower surface may be made from the same material as the flange 2113, with substantially similar flexibility characteristics.

In some embodiments, an anterior portion of the generally U-shaped first member 2110 may include a portion of the upper surface 2112 and a portion of the lower surface extending transversely (left and/or right from the medial line) between the pair of arms to form or act as a bite block configured to be positioned between the incisors of the upper dentition 10 and the lower dentition 20. In some embodiments, the anterior portion may form or include the curved base of the first member. The bite block, which may be further supported by the second member 1180 as described above, may prevent a patient from biting down (intentionally or unintentionally/involuntarily) and partially or fully closing off any of the passageways of the mouthpiece 2100 described herein. In some embodiments, the portion of the upper surface 2112 at the anterior portion of the U-shaped first member 2110 may include an angled ramp element along a posterior edge of the upper surface 2112, the ramp element extending superiorly from the upper surface 2112 in a posterior direction. In use, the ramp element may be positioned behind the upper dentition 10 to aid in retaining the mouthpiece 2100 in the patient's mouth. Similarly, in some embodiments, the portion of the lower surface at the anterior portion of the U-shaped first member 2110 may include a raised ridge element along a posterior edge of the lower surface, the raised ridge extending inferiorly from the lower surface. In use, the raised ridge may be positioned behind the lower dentition 20 to aid in retaining the mouthpiece 2100 in the patient's mouth.

In some embodiments, the upper surface 2112 may be spaced apart from the lower surface, for example, by the at least one lateral interocclusal passageway disposed therebetween. In some embodiments, a posterior central orifice may be disposed along a medial line through the first member 2110, and may extend through the anterior portion of the first member 2110 to provide access to the oral cavity 50 and/or the oropharynx 30. In some embodiments, the upper surface 2112 and the lower surface may be angled toward each other in a posterior direction. In other words, the upper surface 2112 and the lower surface may be closer together at a posterior portion of the first member 2110 than at the anterior portion of the first member 2110, similar to the first member 1110 illustrated in FIGS. 13-14, for example. In some embodiments, the upper surface 2112 and the lower surface of the first member 2110 may be angled toward each other at a greater angle or slope than the upper surface 1112 and the lower surface 1114 of the first member 1110. Additionally, the posterior portion of the first member 2110 may be shorter in length than the posterior portion of the first member 1110. The physical differences of the first member 2110 compared to the first member 1110 may provide increased comfort and minimized gag reflex in patients with a smaller oral cavity 50 (e.g., children). In other words, the first member 2110 may not extend as deeply into the oral cavity 50 of a patient as the first member 1110. Alternatively, in some embodiments, a first member (not shown) may be provided that is larger in size than first member 1110 or first member 2110, for use in patients with a larger mouth. In some embodiments, the tubular portion 2111 of the first member 2110 may be substantially identical in size and configuration to the tubular portion 1111 of the first member 1110. Accordingly, the first member 2110 may be configured to receive the same second member 1180 therein as the first member 1110. Additionally, in some embodiments, alterations may be made to the size and shape of the tubular portion to accommodate a second member (not shown) which is sized larger or smaller than the second member 1180. In some embodiments, variances in the arc or curvature of the upper surface 2112 and the lower surface of the first member 2110 compared to the corresponding features of the first member 1110 may also be made to improve comfort and usability in patients having a smaller oral cavity 50. In some embodiments, variances in the arc or curvature of the upper surface and the lower surface of the first member compared to the corresponding features of the first member 1110 may also be made to improve comfort and usability in patients having a larger oral cavity 50.

In some embodiments, the first member 2110 forms at least one lateral interocclusal passageway extending from the anterior portion to a posterior aperture at the posterior portion. In some embodiments, at the anterior portion, the at least one lateral interocclusal passageway may open into the cavity of the tubular portion 2111. In some embodiments, the upper surface 2112 and the lower surface may be spaced apart by the at least one lateral interocclusal passageway. In some embodiments, the at least one lateral interocclusal passageway may include a left lateral interocclusal passageway and a right lateral interocclusal passageway. In other words, in some embodiments, the first member 2110 may form two (i.e., left and right) lateral interocclusal passageways configured to be positioned within the lateral interocclusal space(s) 40 and/or disposed on opposing sides of the oral cavity 50 extending in an anterior-posterior direction or orientation. In some embodiments, the left and right lateral interocclusal passageways may be substantially mirrored about a vertical plane through a central axis extending anteriorly to posteriorly through the first member 2110 (i.e., a superior-inferior plane through the medial line). In some embodiments, the at least one lateral interocclusal passageway may be configured to provide a conduit for respiratory gas exchange (i.e., breathing). In at least some such embodiments, the cross-sectional area (i.e., size and/or shape) of the at least one lateral interocclusal passageway may be generally sufficient to allow adequate ventilation to the patient. For example, the at least one lateral interocclusal passageway, either each individually and/or collectively, may be dimensioned to have a minimum cross-sectional open pathway area in the range of about 15 mm$^2$ to about 170 mm$^2$, for example in the range of about 50 mm$^2$ to about 150 mm$^2$, or for example in the range of about 80 mm$^2$ to about 140 mm$^2$. These ranges are believed to provide an adequate fluid pathway or conduit for respiratory gas exchange exclusively through the at least one lateral interocclusal passageway within the first member 2110 for most patients, but other sizes and/or ranges are contemplated for specific applications, for example, individual patient needs.

In some embodiments, the first member 2110 may include a sampling port defining a sampling orifice formed and/or disposed within a posterior portion of the at least one lateral interocclusal passageway. In at least some embodiments having more than one lateral interocclusal passageway, each lateral interocclusal passageway may include a sampling port and a sampling orifice (i.e., a left lateral interocclusal sampling port and a right lateral interocclusal sampling port) formed therein. In some embodiments, the sampling orifice may face in a posterior direction toward the posterior aperture. In some embodiments, the sampling orifice may face in other directions, such as, but not limited to, angled, laterally, medially, superiorly, inferiorly, anteriorly, combinations thereof, or other desired angles or orientations. In some embodiments, the sampling port and/or the sampling orifice may be recessed (i.e., disposed anteriorly) from the posterior aperture within the at least one lateral interocclusal passageway. In some embodiments, the sampling port and/or the sampling orifice may be generally flush with, or otherwise positioned at or within, the posterior aperture. In some embodiments, the sampling port and/or the sampling orifice may include a covering disposed thereon and/or a valve disposed therein. In some embodiments, the covering and/or valve may be gas permeable to permit respiratory gases to pass therethrough, while being liquid impermeable to prevent liquids such as saliva, oral secretions, or other liquids from entering the sampling port and/or the sampling orifice. In some embodiments, the first member 2110 may be configured to position the posterior aperture and/or the sampling port between an anterior edge of the second molar and the anterior tonsillar pillar 32.

In some embodiments, the sampling port and/or the sampling orifice may be in fluid communication with and/or fluidly connected to an analyzing apparatus. In at least some embodiments, the first member 2110 may include a sampling conduit extending anteriorly from the sampling port and/or the sampling orifice within the lateral interocclusal passageway to the anterior portion and opening into the cavity of the tubular portion 2111. In some embodiments, the sampling conduit may include a discrete tubular member embedded or molded within the first member 2110, a passageway or lumen integrally formed or molded within the first member 2110, and/or a combination thereof.

In some embodiments, the second member 1180 (shown illustratively in FIGS. 15-18) may be slidably received within the cavity of the tubular portion 2111 of the first member 2110. In some embodiments, one or more posterior surfaces of the second member 1180 may be configured to engage and/or abut one or more anterior surfaces of the first member 2110 within the cavity of the tubular portion 2111. In some embodiments, the second member 1180 may include a perimeter ring 1181 defining an outwardly-facing surface configured to be in facing engagement with an inner surface of the tubular portion 2111. In some embodiments, the second member 1180 may be attached, connected, and/or coupled to the first member 2110 using any appropriate means including, but not limited to, adhesive bonding, mechanical fastener(s), welding, snap fit, interference fit, friction fit, or other suitable means. In some embodiments, the second member 1180 may be detachable from the first member 2110. In some embodiments, the second member 1180 and the first member 2110 may form an air and/or fluid tight fit between them. In some embodiments, a gasket or other sealing element may be disposed between the second member 1180 and the first member 2110. It is contemplated that in some embodiments, the first member 2110 and the second member 1180 may be integrally formed as a single piece.

Other aspects related to the first member 2110, including method of use and interaction with elements, structures, or features, such the adapter 1160, for example, may be substantially the same as for the first member 1110 as disclosed above. For example, in at least some embodiments, the mouthpiece 2100 may be used in spontaneously breathing (and in some cases, sedated) patients, where positive pressure respiration/ventilation is not needed, without the adapter 1160. A plug 500 may be inserted into the anterior central orifice 1128 when access to the oral cavity 50 is not needed and to force respiration to occur through the at least one lateral interocclusal passageway.

Figure 30:
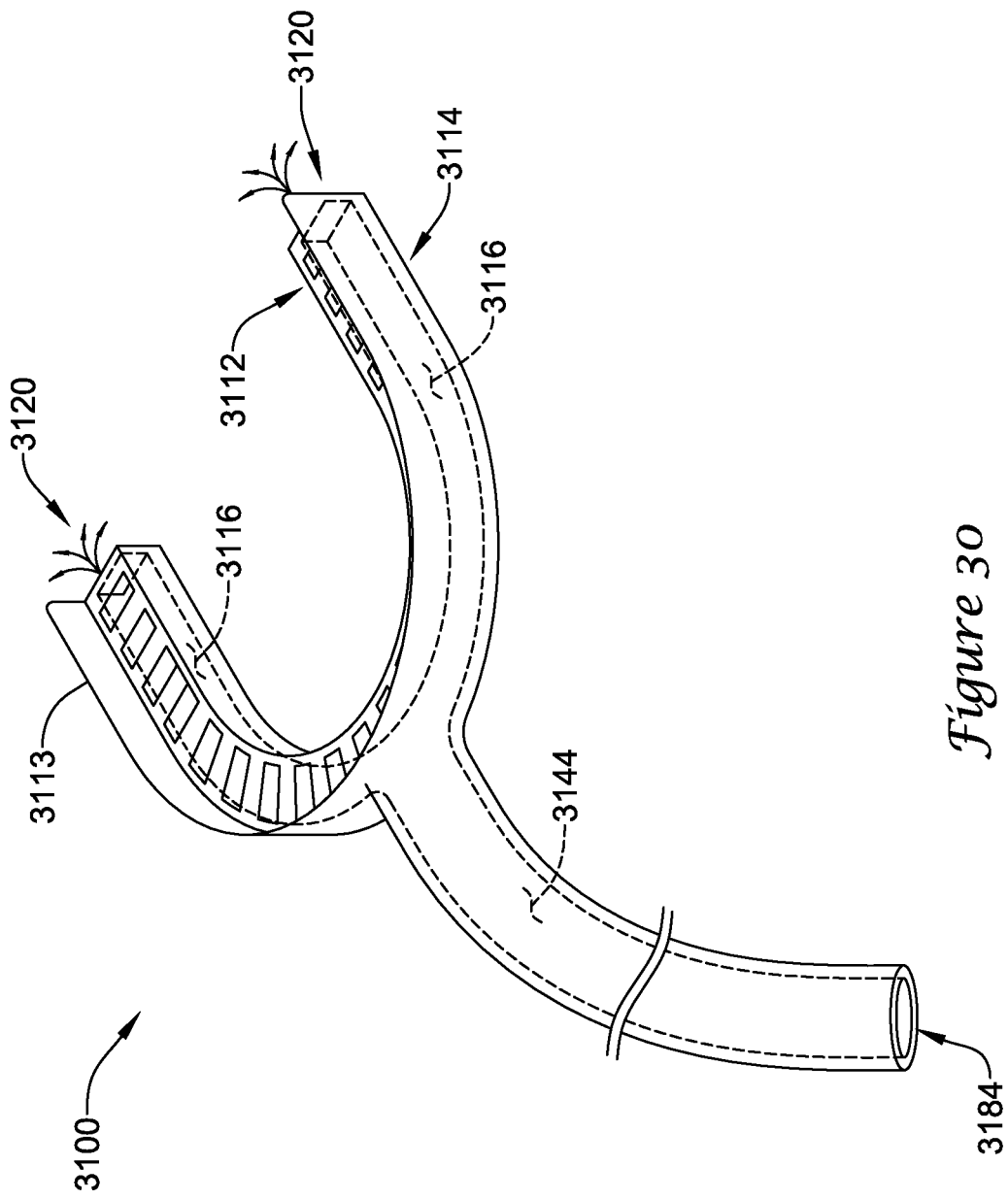
FIG. 30 is a perspective view of an example mouthpiece assembly.

In another embodiment of a medical breathing apparatus, a mouthpiece 3100 may include a generally U-shaped first member having a tubular portion extending anteriorly therefrom and defining a supplemental gas conduit 3144. In some embodiments, the first member (shown illustratively in FIG. 30) may include an upper surface 3112 shaped and configured to receive and/or contact an upper dentition 10 of a patient. In some embodiments, the first member may include a lower surface 3114 shaped and configured to contact a lower dentition 20 of a patient. In some embodiments, the first member may include a flange 3113 extending superiorly from the upper surface 3112 at an outer perimeter or edge of the upper surface 3112. In use, the flange 3113 may be positioned with the upper dentition 10 on a posterior side of the flange 3113 and the lips of the patient on an anterior side of the flange 3113. Accordingly, in some embodiments, the first member and/or the flange 3113 may be made from a generally soft, flexible material such as those disclosed herein, so as to avoid injury to the lips and/or gums of the patient and/or to improve comfort. In some embodiments, the upper surface 3112 and/or the lower surface 3114 may be made from a material that is less flexible and more rigid than the flange 3113. In some embodiments, the upper surface 3112 and/or the lower surface 3114 may be made from a material that is more flexible and less rigid than the flange 3113. In some embodiments, the upper surface 3112 and/or the lower surface 3114 may be made from the same material as the flange 3113, with substantially similar flexibility characteristics.

In some embodiments, the supplemental gas conduit 3144 may include a port 3184 at an anterior end, wherein the port 3184 may be configured to be in fluid communication with a source of supplemental gas (e.g., oxygen). Within the U-shaped first member, the supplemental gas conduit 3144 extends posteriorly as at least one lateral interocclusal passageway 3116 terminating posteriorly at a posterior aperture 3120. For example, in some embodiments, the at least one lateral interocclusal passageway 3116 may include a left lateral interocclusal passageway 3116 and a right lateral interocclusal passageway 3116 each terminating at a separate posterior aperture 3120. Supplemental gas may be supplied through the supplemental gas conduit 3144 and the at least one lateral interocclusal passageway 3116 and delivered through the posterior aperture(s) 3120 to the posterior oropharynx 30 of the patient. The mouthpiece 3100 may be used to delivery supplemental gas (e.g., oxygen) to a patient similar to a nasal cannula. However, the delivery point of the supplemental gas is shifted from the nose to the posterior oropharynx 30.

Compared to some other embodiments described herein, the mouthpiece 3100 may lack the sampling port(s) and a central passageway through the mouthpiece 3100 into the oral cavity 50. Instead, access to the oral cavity 50 would be obtained by simply opening the patient's mouth. In some embodiments, the upper surface 3112 and the lower surface 3114 may not be angled toward each other at a posterior portion, but may instead be generally parallel to each other. However, in some embodiments, the upper surface 3112 and the lower surface 3114 may indeed be angled toward each other at a posterior portion. The at least one lateral interocclusal passageway 3116, lacking the sampling port(s) and the sampling conduit(s) of some other embodiments, may have a reduced cross-sectional area compared to those embodiments. In general, the mouthpiece 3100 may be used in spontaneously breathing patients who do not require positive pressure breathing support (i.e., a ventilator), and/or where respiratory gas analyzing apparatus is unavailable or unnecessary.

Figure 32:
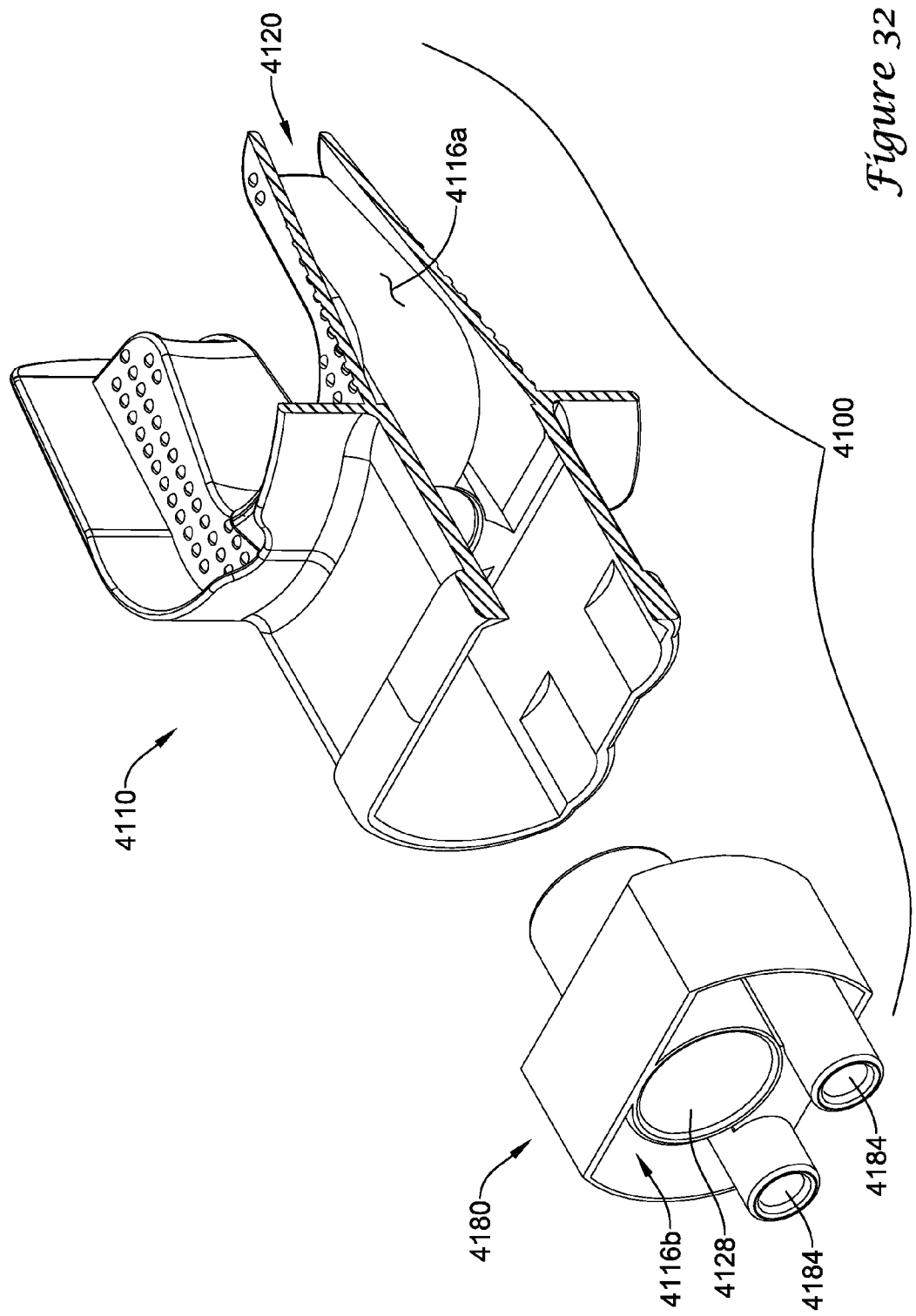
FIG. 32 is an exploded perspective view of an example mouthpiece assembly.

FIG. 32, shown in partial cross-section, illustrates another embodiment of a medical mouthpiece 4100. Similar to the mouthpiece 1100 above, in some embodiments, the mouthpiece 4100 may include a generally U-shaped first member 4110 having a tubular portion extending anteriorly therefrom and defining a first cavity, and a second member 4180. In some embodiments, the U-shaped first member 4110 may include a curved base and a pair of spaced-apart arms extending away from the curved base. In some embodiments, the tubular portion may extend anteriorly from the curved base. In some embodiments, the pair of spaced-apart arms may extend posteriorly from the curved base. In some embodiments, the first member 4110 may include an upper surface shaped and configured to receive and/or contact an upper dentition 10 of a patient. In some embodiments, the first member 4110 may include a lower surface shaped and configured to receive and/or contact a lower dentition 20 of a patient.

In some embodiments, the first member 4110 may include a flange extending superiorly from the upper surface and/or inferiorly from the lower surface at an outer perimeter or edge of the upper surface and/or the lower surface. In use, the flange may be positioned with the upper dentition 10 and lower dentition 20 on a posterior side of the flange and the lips of the patient on an anterior side of the flange. Accordingly, in some embodiments, the first member 4110 and/or the flange may be made from a generally soft, flexible material such as those disclosed herein, so as to avoid injury to the lips and/or gums of the patient and/or to improve comfort. In some embodiments, the upper surface and/or the lower surface may be made from a material that is less flexible and more rigid than the flange. In some embodiments, the upper surface and/or the lower surface may be made from a material that is more flexible and less rigid than the flange. In some embodiments, the upper surface and/or the lower surface may be made from the same material as the flange, with substantially similar flexibility characteristics.

In some embodiments, an anterior portion of the generally U-shaped first member 4110 may include a portion of the upper surface and a portion of the lower surface extending transversely (left and/or right from the medial line) between the pair of spaced-apart arms to form or act as a bite block configured to be positioned between the incisors of the upper dentition 10 and the lower dentition 20. The bite block, which may be further supported by the second member 4180 similar to the bite block described above with respect to the first member 1110 and the second member 1180, may prevent a patient from biting down (intentionally or unintentionally/involuntarily) and partially or fully closing off any of the passageways of the mouthpiece 4100 described herein. In some embodiments, the portion of the upper surface at the anterior portion of the U-shaped first member 4110 may include an angled ramp element along a posterior edge of the upper surface, the ramp element extending superiorly from the upper surface in a posterior direction. In use, the ramp element may be positioned behind the upper dentition 10 to aid in retaining the mouthpiece 4100 in the patient's mouth. Similarly, in some embodiments, the portion of the lower surface at the anterior portion of the U-shaped first member 4110 may include a raised ridge element along a posterior edge of the lower surface, the raised ridge extending inferiorly from the lower surface. In use, the raised ridge may be positioned behind the lower dentition 20 to aid in retaining the mouthpiece 4100 in the patient's mouth.

In some embodiments, the upper surface may be spaced apart from the lower surface, for example, by at least one lateral interocclusal passageway 4116A disposed therebetween. In some embodiments, a posterior central orifice may be disposed along a medial line through the first member 4110, and may extend through the anterior portion of the first member 4110 to provide access to the oral cavity 50 and/or the oropharynx 30. In some embodiments, the upper surface and the lower surface may be angled toward each other in a posterior direction. In other words, the upper surface and the lower surface may be closer together at a posterior portion of the first member 4110 than at the anterior portion of the first member 4110.

In some embodiments, the first member 4110 forms at least one lateral interocclusal passageway 4116A extending from the anterior portion to a posterior aperture 4120 at the posterior portion. In some embodiments, at the anterior portion, the at least one lateral interocclusal passageway 4116A may open into the cavity of the tubular portion. In some embodiments, the upper surface and the lower surface may be spaced apart by the at least one lateral interocclusal passageway 4116A. In some embodiments, the at least one lateral interocclusal passageway 4116A may include a left interocclusal passageway 4116A and a right interocclusal passageway 4116A. In other words, in some embodiments, the first member 4110 may form two (i.e., left and right) lateral interocclusal passageways 4116A configured to be positioned within the lateral interocclusal space(s) 40 and/or disposed on opposing sides of the oral cavity 50 extending in an anterior-posterior direction or orientation. In some embodiments, the left and right lateral interocclusal passageways 4116A may be substantially mirrored about a vertical plane through a central axis extending anteriorly to posteriorly through the first member 4110 (i.e., a superior-inferior plane through the medial line). In some embodiments, the at least one lateral interocclusal passageway 4116A may be configured to provide a conduit for respiratory gas exchange (i.e., breathing). In at least some such embodiments, the cross-sectional area (i.e., size and/or shape) of the at least one lateral interocclusal passageway 4116A may be generally sufficient to allow adequate ventilation to the patient. For example, the at least one lateral interocclusal passageway 4116A, either each individually and/or collectively, may be dimensioned to have a minimum cross-sectional open pathway area in the range of about 15 mm$^2$ to about 170 mm$^2$, for example in the range of about 50 mm$^2$ to about 150 mm$^2$, or for example in the range of about 80 mm$^2$ to about 140 mm$^2$. These ranges are believed to provide an adequate fluid pathway or conduit for respiratory gas exchange exclusively through the at least one lateral interocclusal passageway 4116A within the first member 4110 for most patients, but other sizes and/or ranges are contemplated for specific applications, for example, individual patient needs.

In some embodiments, the second member 4180 may be slidably received within the cavity of the tubular portion of the first member 4110. In some embodiments, one or more posterior surfaces of the second member 4180 may be configured to engage and/or abut one or more anterior surfaces of the first member 4110 within the cavity of the tubular portion. In some embodiments, the second member 4180 may include a perimeter ring defining an outwardly-facing surface configured to be in facing engagement with an inner surface of the tubular portion. In some embodiments, the second member 4180 may be attached, connected, and/or coupled to the first member 4110 using any appropriate means including, but not limited to, adhesive bonding, mechanical fastener(s), welding, snap fit, interference fit, friction fit, or other suitable means. In some embodiments, the second member 4180 may be detachable from the first member 4110. In some embodiments, the second member 4180 and the first member 4110 may form an air and/or fluid tight fit between them. In some embodiments, a gasket or other sealing element may be disposed between the second member 4180 and the first member 4110. It is contemplated that in some embodiments, the first member 4110 and the second member 4180 may be integrally formed as a single piece.

In some embodiments, the second member 4180 may include an anterior central orifice 4128 disposed along a medial line through the second member 4180. In some embodiments, the anterior central orifice 4128 may extend through the perimeter ring of the second member 4180 anteriorly to posteriorly, and in some embodiments, a wall of the anterior central orifice 4128 may further extend posteriorly from the perimeter ring, as seen in FIG. 32. In some embodiments, the wall of the anterior central orifice 4128 extending posteriorly from the perimeter ring may engage with and/or cooperate with the posterior central orifice of the first member 4110, thereby forming a central passageway through the mouthpiece 4100 to provide access to the oral cavity 50 and/or the oropharynx 30. In some embodiments, the wall of the anterior central orifice 4128 may be slidably received within the posterior central orifice. In some embodiments, the wall of the anterior central orifice 4128 may abut an anterior edge of the posterior central orifice. In at least some embodiments, with the mouthpiece 4100 positioned within the mouth of a patient, the anterior central orifice 4128 may be positioned exterior to the mouth of the patient. As such, a medical instrument 800, such as a suction device, an endoscope, an endotracheal tube, etc., for example, may be introduced into the oral cavity 50 through the central passageway as needed or desired.

In at least some embodiments, the second member 4180 may be formed from and/or may include a relatively rigid and/or hard material, such as those listed herein, selected to resist compression, collapse, and/or crushing under pressure. This may permit the second member 4180 and/or the mouthpiece 4100 to resist the compression exerted by a human jaw/bite, which may be useful when a medical instrument 800 is disposed within the posterior central orifice, the anterior central orifice 4128, and/or the central passageway.

In some embodiments, the second member 4180 may include one or more anterior apertures. In some embodiments, at least a portion of the one or more anterior apertures may be formed by the perimeter ring. In some embodiments, the second member 4180 may include one or more lateral interocclusal passageways 4116B disposed inside of and passing through the perimeter ring anteriorly to posteriorly from the one or more anterior apertures. When the second member 4180 is positioned within the cavity of the tubular portion such that the one or more posterior surfaces of the second member 4180 are in engagement with and/or abutting the one or more anterior surfaces of the first member 4110, the one or more lateral interocclusal passageways 4116B of the second member 4180 may be in fluid communication with the at least one lateral interocclusal passageway 4116A of the first member 4110, with a continuous path formed from the anterior apertures to the posterior aperture(s) 4120.

In some embodiments, the second member 4180 may include one or more ports 4184 extending anteriorly of the perimeter ring. Each port 4184 may be fluidly connected to a supplemental gas conduit extending anteriorly to posteriorly through the second member 4180 inside of the perimeter ring. Each supplemental gas conduit terminates posteriorly at a supply orifice. In some embodiments, the supply orifice may be configured to be in fluid communication with the at least one lateral interocclusal passageway 4116A of the first member 4110 when the second member 4180 is disposed within the cavity of the tubular portion. In embodiments having more than one lateral interocclusal passageway 4116A, there may be a distinct supply orifice in fluid communication with each lateral interocclusal passageway 4116A (i.e., a left lateral interocclusal supply orifice and a right lateral interocclusal supply orifice). In some embodiments, the one or more ports 4184, the supplemental gas conduit, and the supply orifice may be in fluid communication with a source of supplemental gas 400, for example, oxygen, nitrous oxide, an aerosolized pharmaceutical, or other suitable gas. In some embodiments, the one or more ports 4184 may be configured to receive, accept, connect to, or otherwise coupled with a means for supplying a supplemental gas from the source of supplemental gas 400 to the mouthpiece 4100, such as a nasal cannula 402 or a section of tubular hose, for example. In some embodiments, the second member 4180 may include two ports 4184, wherein the two ports 4184 are each configured to receive one of two prongs of a nasal cannula 402. In other words, the source of supplemental gas 400 may be operatively connected to the one or more ports 4184 and/or to the supply orifice, similar to what is shown in FIG. 37. In some embodiments, the supply orifice may be configured to deliver a supplemental gas into the at least one lateral interocclusal passageway 4116A. As the supplemental gas is delivered to the supply orifice, the supplemental gas mixes with the air or gas being delivered through the at least one lateral interocclusal passageway 4116A to a space adjacent the patient's oropharynx 30. In some embodiments, the supplemental gas may be delivered at a flow rate of about 0.1 liter per minute to about 15 liters per minute.

In contrast to some embodiments described above, the mouthpiece 4100 may lack or not include the sampling port(s) and sampling conduit(s) used for monitoring respiratory gases, as illustrated in FIG. 32. Similarly, the second member 4180 may lack or not include the manifold 1190. In some cases, the mouthpiece 4100 may be useful where there is no respiratory gas analyzing apparatus available or necessary.

Other aspects related to the first member 4110, including method of use and interaction with elements, structures, or features, such the adapter 1160, for example, may be substantially the same as for the first member 1110 as disclosed above. Similar to the mouthpiece 1100 and the mouthpiece 2100 above, the mouthpiece 4100 may be used in spontaneously breathing patients, where positive pressure respiration/ventilation is not needed, without the adapter 1160.

Figure 33:
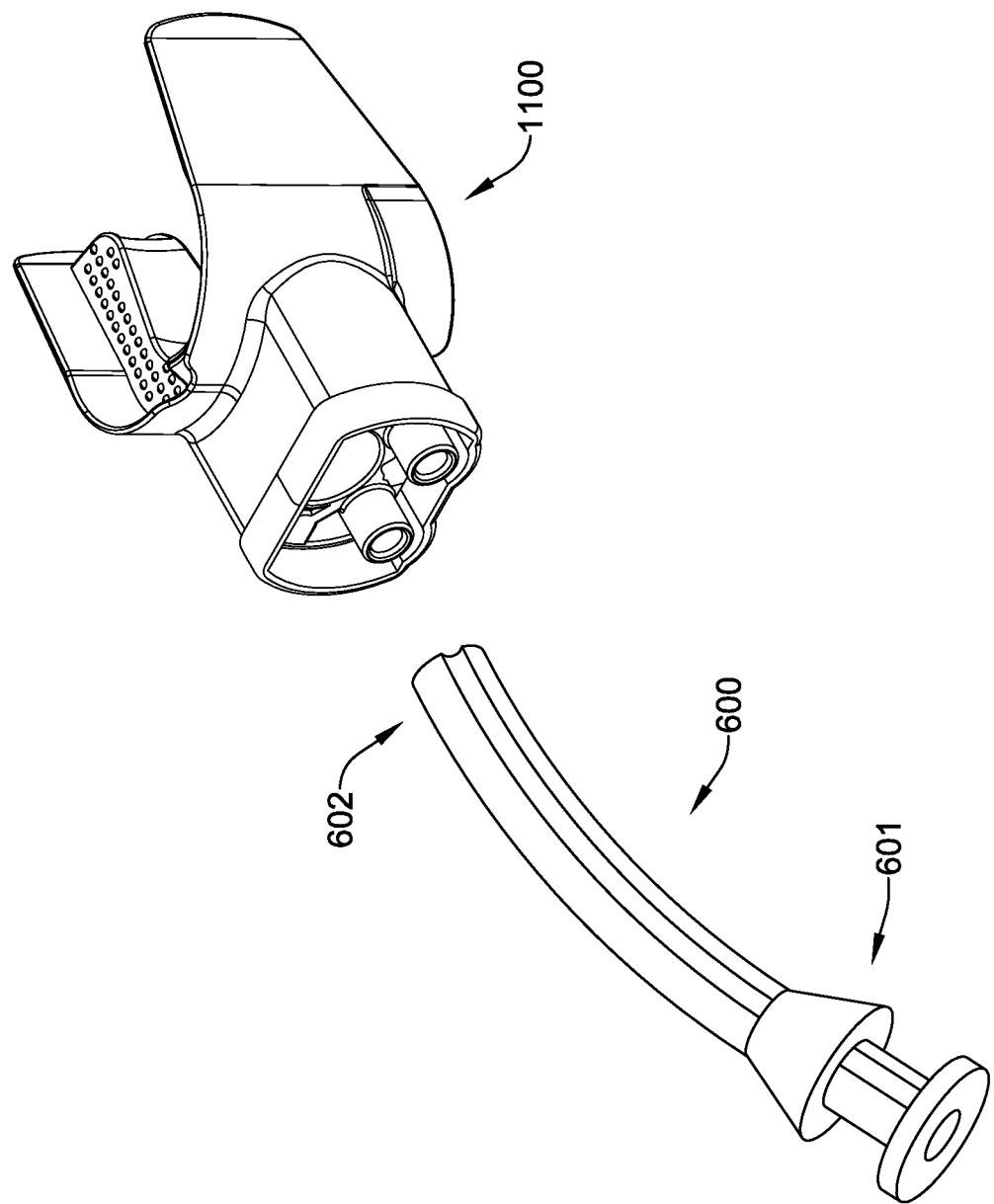
FIG. 33 is a side view of an example mouthpiece assembly and secondary medical device.

FIG. 33 illustrates an example pharyngeal channel 600 that may be used with the mouthpiece 1100. In some embodiments, the pharyngeal channel 600 may include a lumen extending longitudinally therethrough as shown, but this feature is not necessarily required. Alternatively, or additionally, in some embodiments, the pharyngeal channel 600 may include one or more side channels configured to permit respiratory gas passage past the oropharynx 30 unobstructed by the tongue 52. In some embodiments, the pharyngeal channel 600 may include an adjustable locking element 601 disposed at a first end. An opposing second end 602 may be configured for insertion into and/or through the central passageway of the mouthpiece 1100. In some embodiments, the pharyngeal channel 600 may include depth markings on an outer surface thereof, and a guide determining the correct depth based on patient size and/or whether or not the pharyngeal channel 600 is passed through the central passageway with the adapter 1160 engaged to the mouthpiece 1100. For example, in some embodiments, the presence of the adapter 1160 may result in a longer central passageway, which may affect the depth to which the pharyngeal channel 600 is inserted. In some embodiments, the adjustable locking element 601 may be slidable on and/or rotatable about an outer surface of the pharyngeal channel 600 to adjust insertion depth of the pharyngeal channel 600 for proper positioning in each individual patient. In some embodiments, the pharyngeal channel 600 may be positioned such that the second end 602 of the pharyngeal channel 600 is disposed posteriorly of the tongue 52, thereby physically displacing the tongue 52 anteriorly from the posterior wall of the oropharynx 30 to break or prevent airway obstruction at this location. In some embodiments, the pharyngeal channel 600 may be appropriate for use in patients having a blunted or eliminated gag reflex, such as a patient in a state of sedation, and/or an anesthetized or unconscious patient.

In some embodiments, one or more additional features of a medical mouthpiece may be provided. For ease of understanding, mouthpiece 1100 will be referred to in the following discussion, but it is to be understood that any mouthpiece (and the corresponding elements thereof) described herein may include one or more of the following described features, shown illustratively in FIGS. 34-36, and may include various combinations thereof.

Figure 34:
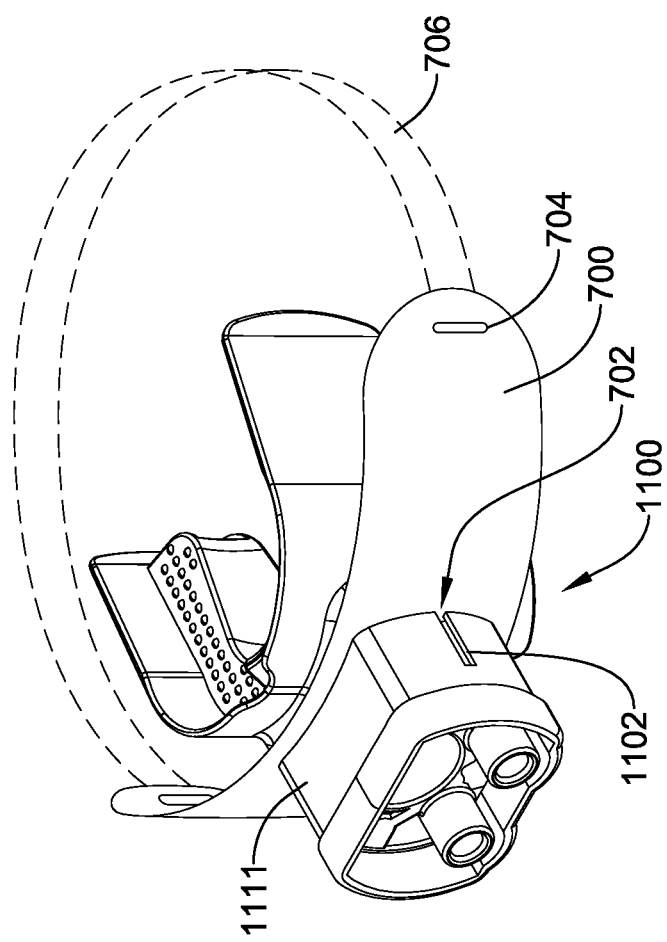
FIG. 34 is a perspective view of an example mouthpiece assembly.

In some embodiments, as shown in FIG. 34 for example, a mouthpiece 1100 may include a cheek flap 700 configured to rest and/or seal against the cheeks of the patient. In some embodiments, the cheek flap 700 may be slidably disposed about the tubular portion 1111 of the first member 1110. In some embodiments, one or more retaining slots 1102 (e.g., T-slot) may be formed in an outer surface of the wall of the tubular portion 1111. The cheek flap 700 may have one or more corresponding protrusions configured to slidably engage the one or more retaining slots 1102. The cheek flap 700 may include a strap 706 coupled to the cheek flap 700, for example, using slots 704. In some embodiments, the strap 706 may be integrally formed with the cheek flap 700. In some embodiments, the strap 706 may be elastic and/or adjustable in length to fit about/behind a patient's head. In use, the cheek flap 700 and the strap 706 cooperate to secure the cheek flap 700 against the patient's mouth and cheeks, thereby retaining the mouthpiece 1100 within the mouth of the patient and/or creating a seal between an inner mucosal surface of the cheeks and/or lips and an outer surface of the flange 1113. The seal may be beneficial in ensuring that respiratory gas delivered under positive pressure through the at least one lateral interocclusal passageway is directed or transmitted to a patient's airway, and/or preventing respiratory gas delivered under positive pressure through the at least one lateral interocclusal passageway from escaping around the mouthpiece 1100.

Figure 35:
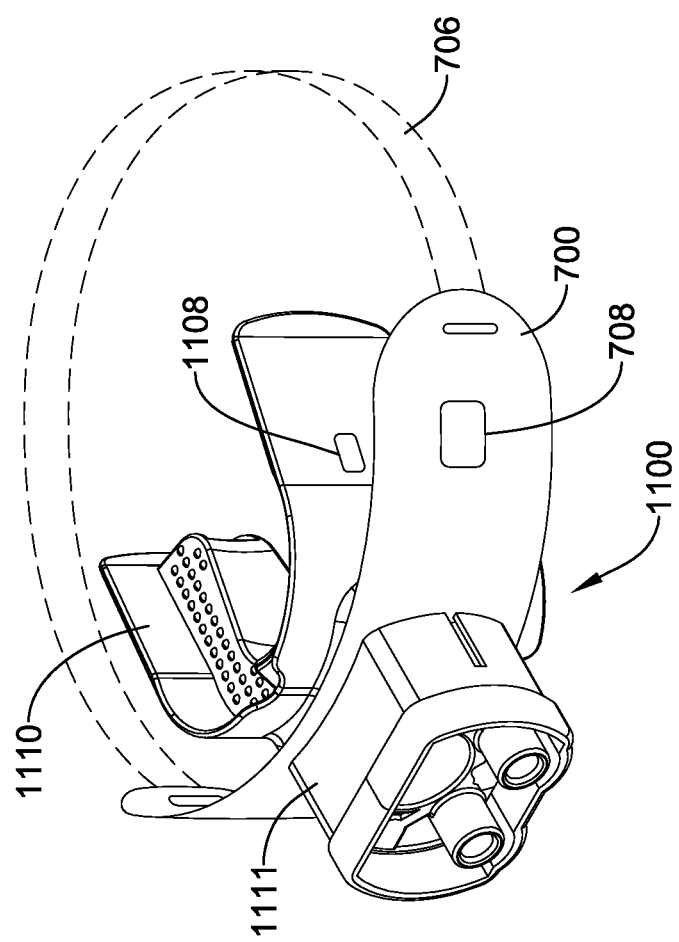
FIG. 35 is a perspective view of an example mouthpiece assembly.

In at least some embodiments, as shown in FIG. 35 for example, a mouthpiece 1100 may include an light emitting diode (LED) 1108 embedded in or mounted on the first member 1110, facing in an outward direction. In at least some embodiments, a strap 706 may include an photodiode 708 embedded therein or mounted thereon facing toward the first member 1110 and/or the light emitting diode (LED) 1108. In some embodiments, the light emitting diode (LED) 1108 and the photodiode 708 may be used for pulse oximetry. Pulse oximetry is a non-invasive method of measuring oxygen saturation of a patient's blood. Light of two wavelengths emitted by the light emitting diode (LED) 1108 may be passed through a thin part of a patient's body, such as a finger, an earlobe, or in the case of the present disclosure, a cheek, to the photodiode 708. The changing absorbance at each of the wavelengths is measured, allowing determination of the absorbances due to the pulsing arterial blood alone, excluding venous blood, skin, bone, muscle, and fat. The measured oxygen saturation may be used to determine and/or adjust the amount of supplemental gas (e.g., oxygen) that is being supplied to the patient. For example, if the measured oxygen saturation is below a desired level, additional oxygen may be provided to the patient through the supply orifice(s) and supplemental gas conduit(s) of the mouthpiece 1100. Alternatively, if the measured oxygen saturation is too high, less oxygen may be supplied to the patient through the supply orifice(s) and supplemental gas conduit(s) of the mouthpiece 1100, or the supplemental gas may be discontinued altogether. In some embodiments, the light emitting diode (LED) 1108 and the photodiode 708 may be self-contained. In other words, each of the light emitting diode (LED) 1108 and the photodiode 708 may include a power source and/or a means to supply data. Although not explicitly shown, in some embodiments, the light emitting diode (LED) 1108 and/or the photodiode 708 may include a wired connection to an external power source and/or a data processor, storage, or monitoring unit. Similarly, although not explicitly shown, in some embodiments, the light emitting diode (LED) 1108 and/or the photodiode 708 may include a wireless connection to an external power source and/or a data processor, storage, or monitoring unit.

Figure 36:
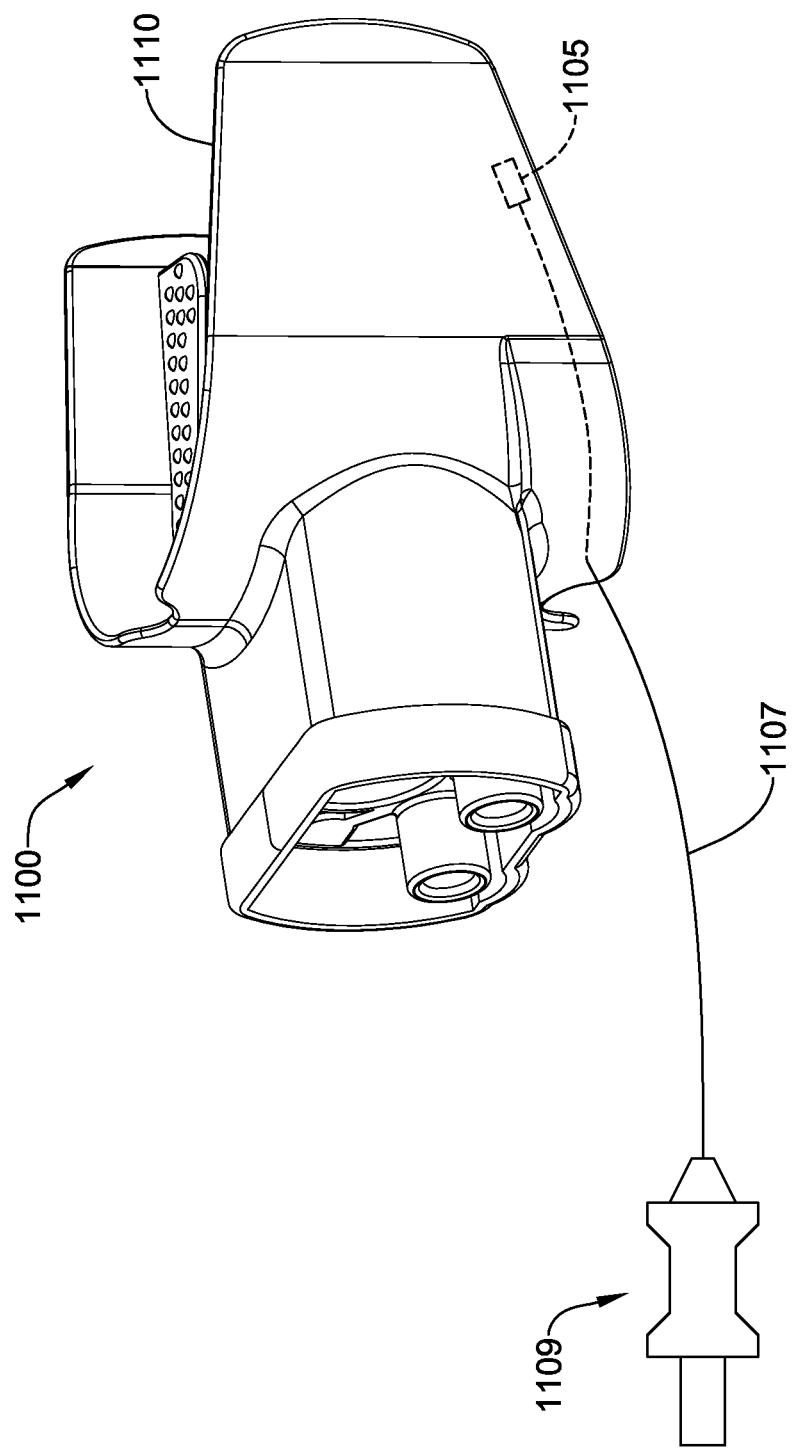
FIG. 36 is a perspective view of an example mouthpiece assembly.

In some embodiments, as shown in FIG. 36 for example, a mouthpiece 1100 may include a first member 1110 having a temperature sensor 1105 embedded therein or mounted thereon. In some embodiments, the temperature sensor 1105 may be self-contained. In other words, each of the temperature sensor 1105 may include a power source and/or a means to supply data. In some embodiments, the temperature sensor 1105 may include a wire or wires 1107 extending away from the first member 1110 to a plug 1109 configured to connect to an external power source and/or a data processor, storage, or monitoring unit. Similarly, although not explicitly shown, in some embodiments, the temperature sensor 1105 may include a wireless connection to an external power source and/or a data processor, storage, or monitoring unit.

FIG. 37 illustrates an example mouthpiece 1100 disposed within a patient's mouth anatomy, similar to FIG. 9 above. Additionally, FIG. 37 illustrates various connections to additional elements, devices, or features. For example, in some embodiments, an adapter 1160 may be configured to couple with and/or connect to the mouthpiece 1100. In some embodiments, a pressure device 200 may be configured to fluidly connect to the adapter 1160, for example, to the respiratory orifice 1174. In some embodiments, the central orifice 1172 of the adapter 1160 and/or the anterior central orifice 1128 of the mouthpiece 1100 may be configured to receive a medical instrument 800 therethrough. In some embodiments, a source of supplemental gas 400 may be configured to fluidly connect to the second port(s) 1184 of the mouthpiece 1100. In some embodiments, the source of supplemental gas 400 may be configured to fluidly connect to the second ports 1184 with or using a nasal cannula 402. In some embodiments, an analyzing apparatus 300 may be configured to fluidly connect to a first port 1182 of the mouthpiece 1100.

In some embodiments, certain features of the above described embodiment(s) may be defined, described, or characterized according to one or more of the following aspects:

1. A medical mouthpiece, comprising:
a generally U-shaped first member having a tubular portion extending anteriorly therefrom, the first member including an upper surface configured to contact an upper dentition of a patient spaced apart from a lower surface configured to contact a lower dentition of the patient;
wherein the first member includes a posterior central orifice extending anteriorly to posteriorly through the first member along a medial line;
wherein the first member forms at least one lateral interocclusal passageway extending anteriorly to posteriorly through the first member between the upper surface and the lower surface; and
a second member slidably received within the tubular portion, the second member including a perimeter ring defining an outwardly-facing surface configured to be in facing engagement with an inner surface of the tubular portion;
wherein the second member includes an anterior central orifice extending anteriorly to posteriorly through the second member along the medial line, the anterior central orifice cooperating with the posterior central orifice to form a central passageway extending through the mouthpiece;
wherein the second member includes one or more anterior apertures and at least one lateral interocclusal passageway passing through the perimeter ring anteriorly to posteriorly from the one or more anterior apertures.

2. The medical mouthpiece of aspect 1, wherein the second member includes a supplemental gas conduit providing fluid communication between a source of supplemental gas and a supply orifice in fluid communication with the at least one lateral interocclusal passageway of the first member.

3. The medical mouthpiece of aspect 2, further comprising:
a sampling port formed within a posterior portion of the at least one lateral interocclusal passageway of the first member; and
a sampling conduit providing fluid communication between the sampling port and an analyzing apparatus configured to analyze respiratory gases.

4. The medical mouthpiece of aspect 3, wherein the supply orifice is disposed anteriorly of the sampling port.

5. The medical mouthpiece of any of aspects 3-4, wherein the analyzing apparatus is configured to monitor partial pressure of carbon dioxide ($CO_2$), oxygen ($O_2$), nitrous oxide ($N_2O$), or anesthetic gas in exhaled respiratory gas.

6. The medical mouthpiece of any of aspects 3-5, further including a manifold coupled to the second member in fluid communication with the sampling conduit, the manifold including a first port configured to fluidly connect to the analyzing apparatus.

7. The medical mouthpiece of aspect 6, wherein the manifold extends through a manifold aperture disposed in a wall of the tubular portion of the first member.

8. The medical mouthpiece of any of aspects 1-7, wherein when the medical mouthpiece is positioned in a mouth of the patient, the central passageway permits access to an oral cavity of the patient for the introduction of a medical instrument therein.

9. The medical mouthpiece of any of aspects 1-8, wherein the at least one lateral interocclusal passageway of the first member includes a left lateral interocclusal passageway and a right lateral interocclusal passageway, the left and right lateral interocclusal passageways configured to be disposed on opposing sides of an oral cavity of the patient.

10. The medical mouthpiece of any of aspects 1-9, wherein when the medical mouthpiece is positioned in a mouth of the patient, the one or more anterior apertures is positioned exterior to the mouth of the patient.

11. The medical mouthpiece of any of aspects 1-10, wherein the one or more anterior apertures is configured to fluidly connect to respiratory equipment.

12. The medical mouthpiece of any of aspects 1-11, wherein the at least one lateral interocclusal passageway of the first member extends along an axis defined by a line between the upper dentition and the lower dentition, the at least one lateral interocclusal passageway of the first member being configured to provide a conduit for respiratory gas exchange.

13. The medical mouthpiece of any of aspects 2-7, wherein the supply orifice is configured to deliver supplemental gas into the at least one lateral interocclusal passageway of the first member for inspiration.

14. The medical mouthpiece of aspect 13, wherein the supplemental gas is delivered at a flow rate of about 0.1 liters per minute to about 15 liters per minute.

15. The medical mouthpiece of any of aspects 1-14, wherein the at least one lateral interocclusal passageway of the first member is fluidly connected to a ventilator or pressure device configured to deliver continuous or intermittent positive pressure thereto.

16. A medical breathing apparatus, comprising:

a generally U-shaped first member forming an upper surface spaced apart from a lower surface with left and right lateral interocclusal passageways formed therebetween, the left and right lateral interocclusal passageways extending from an anterior portion of the first member through a posterior portion of the first member, and a posterior central orifice extending through the anterior portion from a first cavity defined by a tubular portion extending anteriorly from the anterior portion of the first member;

wherein the first member is shaped and configured to contact an upper dentition of a patient with the upper surface or a lower dentition of a patient with the lower surface;

a second member attached to the anterior portion, the second member including an anterior central orifice extending through the second member and in communication with the posterior central orifice to form a central passageway extending through the mouthpiece;

wherein the second member includes one or more anterior apertures in fluid communication with the left and right lateral interocclusal passageways; and an adapter slidably receivable within the first cavity of the tubular portion of the first member, wherein the adapter includes a central orifice configured to engage the second member as an extension of the central passageway, and a respiratory orifice configured to deliver respiratory gas to the left and right lateral interocclusal passageways.

17. The medical breathing apparatus of aspect 16, wherein the second member includes a first port and one or more second ports formed therein;

the first port being fluidly connected to a sampling port for sampling respiratory gases, the sampling port being disposed within one of the left and right interocclusal passageways proximate the posterior portion;

the one or more second ports being fluidly connected to the left and right lateral interocclusal passageways for delivery of a supplemental gas into the left and right lateral interocclusal passageways.

18. The medical breathing apparatus of aspect 17, wherein the first port is fluidly connected to an analyzing apparatus configured to collect and analyze respiratory gas.

19. The medical breathing apparatus of any of aspects 17-18, wherein the one or more second ports is fluidly connected to a source of supplemental gas for inspiration.

20. The medical breathing apparatus of any of aspects 16-19, wherein the upper surface and the lower surface angle toward each other in a posterior direction.

21. The medical breathing apparatus of any of aspects 16-20, wherein the adapter is removable from the tubular portion of the first member.

22. The medical breathing apparatus of any of aspects 16-21, wherein the respiratory orifice is configured to connect to respiratory equipment selected from: a ventilator, an anesthesia circuit, a CPAP device, a BiPAP device, a rescue bag valve device, or combinations thereof.

23. The medical breathing apparatus of any of aspects 16-22, further including a plug configured to be removably inserted into the central passageway or the central orifice.

24. A method for delivering a respiratory gas to a patient, the method comprising:

inserting a mouthpiece according to aspect 1 into a mouth of the patient; and delivering the respiratory gas to the patient through the at least one lateral interocclusal passageway of the first member such that the respiratory gas is delivered through a posterior aperture to a space adjacent a posterior oropharynx of the patient.

25. The method of aspect 24, wherein the second member includes a supplemental gas conduit in fluid communication with the at least one lateral interocclusal passageway of the first member, and the method further includes: delivering a supplemental gas through the supplemental gas conduit and into the at least one lateral interocclusal passageway of the first member, the supplemental gas mixing with the respiratory gas and being delivered to the posterior oropharynx.

26. The method of aspect 24 or 25, wherein the first member includes a sampling port disposed within a posterior portion of the at least one lateral interocclusal passageway of the first member, and a sampling conduit fluidly connecting the sampling port to an analyzing apparatus, and the method further includes:

collecting a sample of respiratory gas at the sampling port; and analyzing the sample for partial pressure of carbon dioxide ($CO_2$), oxygen ($O_2$), nitrous oxide ($N_2O$), or anesthetic gas.

27. The method of aspect 26, further including: plotting the partial pressure as a function of time or exhaled respiratory gas volume.

28. The medical mouthpiece of any of aspects 3-7 or the medical breathing apparatus of any of aspects 17-19, wherein the sampling port includes a covering disposed thereon, the covering being impermeable to liquid and permeable to gas.

29. The medical breathing apparatus of any of aspects 16-23, wherein the left and right lateral interocclusal passageways are configured to provide a conduit for respiratory gas exchange.

30. The medical breathing apparatus of any of aspects 16-23, wherein the left and right lateral interocclusal passageways are configured to provide a conduit for supplemental gas delivery.

31. The medical breathing apparatus of any of aspects 16-23, wherein the left and right lateral interocclusal passageways are configured to provide a conduit for delivery of continuous pressure.

32. The medical breathing apparatus of any of aspects 16-23, wherein the left and right lateral interocclusal passageways are configured to provide a conduit for delivery of intermittent pressure.

33. The medical breathing apparatus of any of aspects 16-23, wherein the left and right lateral interocclusal passageways are each configured to provide a fluid passageway extending from the one or more anterior apertures to a posterior aperture.

34. The medical mouthpiece of any of aspects 3-7 or the medical breathing apparatus of any of aspects 17-19, wherein the sampling port has a sampling orifice.

35. The medical mouthpiece or the medical breathing apparatus of aspect 34, wherein the sampling orifice is facing in a posterior direction.

36. The medical mouthpiece or the medical breathing apparatus of aspect 34, wherein the sampling orifice is facing in a direction that is other than a posterior direction.

37. A method for sampling respiratory gases of a patient, the method comprising:
inserting a mouthpiece into a mouth of the patient, the mouthpiece having a generally U-shaped member forming a lateral interocclusal passageway extending posteriorly between an upper dentition and a lower dentition of the patient;
collecting a sample of respiratory gases through at least a portion of the interocclusal passageway; and
analyzing the sample.

38. The method of aspect 37, wherein the analyzing step includes analyzing for partial pressure of carbon dioxide (CO2), oxygen (O2), nitrous oxide (N2O), or anesthetic gas.

39. The method of aspect 37 or 38, wherein the mouthpiece includes a supplemental gas conduit in fluid communication with the lateral interocclusal passageway, and the method further includes: delivering a supplemental gas through the supplemental gas conduit and into the lateral interocclusal passageway.

40. The method of any of aspects 37-39, wherein the mouthpiece includes a sampling port disposed within a posterior portion of the lateral interocclusal passageway, and a sampling conduit fluidly connecting the sampling port to an analyzing apparatus, and the method further includes: collecting a sample of respiratory gas at the sampling port.

41. A method of delivering a supplemental gas to a patient, comprising: inserting a mouthpiece into a mouth of the patient, the mouthpiece having a generally U-shaped first member forming at least one lateral interocclusal passageway extending posteriorly between an upper dentition and a lower dentition of the patient; and delivering the supplemental gas into the at least one lateral interocclusal passageway such that the supplemental gas is drawn or discharged through a posterior aperture adjacent a posterior oropharynx of the patient.

42. The method of aspect 41, wherein the mouthpiece includes a supplemental gas conduit extending from the U-shaped first member to a source of supplemental gas.

43. The mouthpiece of any of aspects 1-15, further comprising a cheek flap having a retaining strap coupled thereto.

44. The mouthpiece of aspect 43, wherein the cheek flap is slidably disposed about the tubular portion of the first member.

45. The mouthpiece of any of aspects 43-44, wherein the first member includes a light emitting diode and the cheek flap includes a photodiode facing toward the light emitting diode.

46. The mouthpiece of any of aspects 1-15 or 43-45, or the medical breathing apparatus of any of aspects 16-23 or 29-33, wherein the first member is configured to avoid delivering a respiratory gas directly onto a tongue of the patient.

47. The mouthpiece of any of aspects 1-15 or 43-45, or the medical breathing apparatus of any of aspects 16-23 or 29-33, wherein the first member is configured to avoid delivering a respiratory gas directly onto a cheek of the patient.

48. The mouthpiece of any of aspects 1-15 or 43-45, or the medical breathing apparatus of any of aspects 16-23 or 29-33, wherein the first member is configured to deliver a respiratory gas to an oropharynx of the patient without eliciting a gag reflex.

49. The mouthpiece of any of aspects 1-15 or 43-45, or the medical breathing apparatus of any of aspects 16-23 or 29-33, wherein the first member is configured to deliver a respiratory gas to an oropharynx of the patient without stimulating salivation.

50. The method of any of aspects 24-27, wherein the first member includes a light emitting diode and the mouthpiece includes a cheek flap having a photodiode facing toward the light emitting diode, the method further comprising:
emitting two wavelengths of light from the light emitting diode toward a cheek of the patient; and
receiving the two wavelengths of light outside the mouth of the patient with the photodiode.

51. The method of aspect 50, further comprising: analyzing the two wavelengths of light received to determine oxygen saturation in blood of the patient.

52. The mouthpiece of any of aspects 1-15 or 43-45, or the medical breathing apparatus of any of aspects 16-23 or 29-33, wherein the first member includes a temperature sensor.

53. A method of delivering continuous or intermittent positive pressure to a patient for the purpose of assisting ventilation or relieving airway obstruction, comprising:
inserting a mouthpiece into a mouth of the patient;
engaging an adapter to the mouthpiece;
connecting respiratory equipment configured to delivery continuous or intermittent positive pressure to a respiratory orifice of the adaptor; and
delivering a respiratory gas under continuous or intermittent positive pressure to the patient through the mouthpiece.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:
1. A medical mouthpiece, comprising:
a generally U-shaped first member having a tubular portion extending anteriorly therefrom, the first member including an upper surface configured to contact an upper dentition of a patient spaced apart from a lower surface configured to contact a lower dentition of the patient;
wherein the first member includes a posterior central orifice extending anteriorly to posteriorly through the first member along a medial line;

wherein the first member forms at least one lateral interocclusal passageway extending anteriorly to posteriorly through the first member between the upper surface and the lower surface, the at least one lateral interocclusal passageway being configured to be positioned within a lateral interocclusal space of the patient; and a second member slidably received within the tubular portion, the second member including a perimeter ring defining an outwardly-facing surface configured to be in facing engagement with an inner surface of the tubular portion;

wherein the second member includes an anterior central orifice extending anteriorly to posteriorly through the second member along the medial line, the anterior central orifice cooperating with the posterior central orifice to form a central passageway extending through the mouthpiece;

wherein the second member includes one or more anterior apertures and at least one lateral passageway passing through the perimeter ring anteriorly to posteriorly from the one or more anterior apertures, the at least one lateral passageway of the second member being in fluid communication with the at least one lateral interocclusal passageway of the first member.

2. The medical mouthpiece of claim 1, wherein the second member includes a supplemental gas conduit providing fluid communication between a source of supplemental gas and a supply orifice in fluid communication with the at least one lateral interocclusal passageway of the first member.

3. The medical mouthpiece of claim 2, further comprising:
a sampling port formed within a posterior portion of the at least one lateral interocclusal passageway of the first member; and
a sampling conduit providing fluid communication between the sampling port and an analyzing apparatus configured to analyze respiratory gas.

4. The medical mouthpiece of claim 3, wherein the supply orifice is disposed anteriorly of the sampling port.

5. The medical mouthpiece of claim 3, further including a manifold coupled to the second member in fluid communication with the sampling conduit, the manifold including a first port configured to fluidly connect to the analyzing apparatus.

6. The medical mouthpiece of claim 3, wherein the sampling port includes a covering disposed thereon, the covering being impermeable to liquid and permeable to gas.

7. The medical mouthpiece of claim 1, wherein the at least one lateral interocclusal passageway of the first member includes a left lateral interocclusal passageway and a right lateral interocclusal passageway, the left and right lateral interocclusal passageways configured to be disposed on opposing sides of an oral cavity of the patient.

8. The medical mouthpiece of claim 1, wherein when the medical mouthpiece is positioned in a mouth of the patient, the one or more anterior apertures is positioned exterior to the mouth of the patient.

9. The medical mouthpiece of claim 1, further comprising a cheek flap having a retaining strap coupled thereto.

10. The medical mouthpiece of claim 9, wherein the cheek flap is slidably disposed about the tubular portion of the first member.

11. The medical mouthpiece of claim 9, wherein the first member includes a light emitting diode and the cheek flap includes a photodiode facing toward the light emitting diode.

12. The medical mouthpiece of claim 1, wherein the first member includes a temperature sensor.

13. A method for delivering a respiratory gas to a patient, the method comprising:
inserting a mouthpiece according to claim 1 into a mouth of the patient; and
delivering the respiratory gas to the patient through the at least one lateral interocclusal passageway of the first member such that the respiratory gas is delivered through a posterior aperture to a space adjacent a posterior oropharynx of the patient.

14. The method of claim 13, wherein the second member includes a supplemental gas conduit in fluid communication with the at least one lateral interocclusal passageway of the first member, and the method further includes:
delivering a supplemental gas through the supplemental gas conduit and into the at least one lateral interocclusal passageway of the first member, the supplemental gas mixing with the respiratory gas and being delivered to the posterior oropharynx.

15. The method of claim 13, wherein the first member includes a sampling port disposed within a posterior portion of the at least one lateral interocclusal passageway of the first member, and a sampling conduit fluidly connecting the sampling port to an analyzing apparatus, and the method further includes:
collecting a sample of respiratory gas at the sampling port; and
analyzing the sample for partial pressure of carbon dioxide ($CO2$), oxygen ($O2$), nitrous oxide ($N2O$), or anesthetic gas.

16. The method of claim 15, further including:
plotting the partial pressure of carbon dioxide ($CO2$), oxygen ($O2$), nitrous oxide ($N2O$), or anesthetic gas as a function of time or exhaled respiratory gas volume.

* * * * *